United States Patent
Kolczewski et al.

(10) Patent No.: US 8,080,541 B2
(45) Date of Patent: Dec. 20, 2011

(54) CARBOCYCLIC GLYT-1 RECEPTOR ANTAGONISTS

(75) Inventors: Sabine Kolczewski, Loerrach (DE); Emmanuel Pinard, Linsdorf (FR)

(73) Assignee: Hoffman-La Roche Inc., Nutley, NY (US)

( * ) Notice: Subject to any disclaimer, the term of this patent is extended or adjusted under 35 U.S.C. 154(b) by 0 days.

(21) Appl. No.: 12/859,305

(22) Filed: Aug. 19, 2010

(65) Prior Publication Data
US 2011/0053904 A1 Mar. 3, 2011

(30) Foreign Application Priority Data
Aug. 27, 2009 (EP) .................... 09168859

(51) Int. Cl.
| | |
|---|---|
| A61K 31/166 | (2006.01) |
| A61K 31/40 | (2006.01) |
| A61K 31/5375 | (2006.01) |
| A61K 31/397 | (2006.01) |
| A61K 31/451 | (2006.01) |
| A61K 31/351 | (2006.01) |
| A61K 31/382 | (2006.01) |
| C07D 207/04 | (2006.01) |
| C07D 295/155 | (2006.01) |
| C07D 205/04 | (2006.01) |
| C07D 211/06 | (2006.01) |
| C07D 207/12 | (2006.01) |
| C07D 309/14 | (2006.01) |
| C07D 335/02 | (2006.01) |
| C07D 487/10 | (2006.01) |
| C07D 211/74 | (2006.01) |
| C07D 211/62 | (2006.01) |
| C07C 235/58 | (2006.01) |
| A61P 25/28 | (2006.01) |
| A61P 25/18 | (2006.01) |
| A61P 29/00 | (2006.01) |
| A61P 25/00 | (2006.01) |

(52) U.S. Cl. ........... 514/210.01; 514/210.18; 514/239.5; 514/327; 514/330; 514/331; 514/424; 514/429; 514/432; 514/459; 514/622; 544/159; 546/221; 546/225; 546/234; 548/578; 548/950; 548/541; 548/953; 564/177; 549/424; 549/28

(58) Field of Classification Search .................... None
See application file for complete search history.

(56) References Cited

U.S. PATENT DOCUMENTS
4,215,114 A 7/1980 Szmuszkovic

FOREIGN PATENT DOCUMENTS
DE 2749984 5/1978

OTHER PUBLICATIONS

Cherney et al., caplus an 2004:701975.*
Lewis D.A. & Lieberman J. A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell, vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L. J. Neural Trans. vol. 105, pp. 525-535 (1998).
Yang et al., Bioorganic & Medicinal Chemistry (2000) vol. 8, No. 2 pp. 321-327.

* cited by examiner

*Primary Examiner* — Sun Jae Loewe
(74) *Attorney, Agent, or Firm* — George W. Johnston; Patricia S. Rocha-Tramaloni; Kimberly J. Prior

(57) ABSTRACT

The present invention relates to the use of a compound of formula I

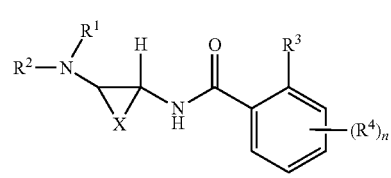

wherein $R^1$, $R^2$, $R^3$, $R^4$, X and n are as defined herein or to a pharmaceutically acceptable acid addition salt, to a racemic mixture, or to its corresponding enantiomers and/or optical isomers for the treatment of psychoses, pain, dysfunction in memory and learning, attention deficit, schizophrenia, dementia disorders or Alzheimer's disease.

6 Claims, No Drawings

CARBOCYCLIC GLYT-1 RECEPTOR ANTAGONISTS

PRIORITY TO RELATED APPLICATION(S)

This application claims the benefit of European Patent Application No. 09168859.8, filed Aug. 27, 2009, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 2000, 28:325-33). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 2001, 5(4): 507-518; Nakazato A and Okuyama S, et al., 2000, *Exp. Opin. Ther. Patents*, 10(1): 75-98). This pharmacological approach poorly address negative and cognitive symptoms which are the best predictors of functional outcome (Sharma T., *Br. J. Psychiatry*, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, *Biol. Psychiatry*, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, *Cell*, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, *The organization of behavior*, Wiley, NY; Bliss TV and Collingridge G L, 1993, *Nature*, 361: 31-39). Transgenic mice overexpressing the NMDA NR2B subunit exhibit enhanced synaptic plasticity and superior ability in learning and memory (Tang J P et al., 1999, *Nature:* 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, *Mol. Mem. Biol.*, 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, *Proc. Natl. Acad. Sci. USA*, 95: 15730-15734; Chen L et al., 2003, *J. Neurophysiol.*, 89 (2): 691-703).

Glycine transporters inhibitors are suitable for the treatment of neuroligical and neuropsychiatric disorders. The majority of diseases states implicated are psychoses, schizophrenia (Armer R E and Miller D J, 2001, *Exp. Opin. Ther. Patents*, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, *Prog. Neurobiol.*, 67: 173-202), autistic disorders (Carlsson M L, 1998, *J. Neural Transm.* 105: 525-535), cognitive disorders such as dementias, including age related dementia and senile dementia of the Alzheimer type, memory disorders in a mammal, including a human, attention deficit disorders and pain (Armer R E and Miller D J, 2001, *Exp. Opin. Ther. Patents*, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides methods for the treatment of psychoses, pain, dysfunction in memory and learning, attention deficit, schizophrenia, dementia disorders or Alzheimer's disease which comprises administering a compound of formula I

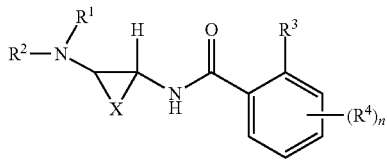

I wherein
R¹ and R² are each independently hydrogen, lower alkyl, —(CH₂)ₒ-cycloalkyl wherein o is 0 or 1, or are benzyl or heterocycloalkyl;
or R¹ and R² together with the N-atom to which they are attached form a ring containing —(CH₂)₃—, —(CH₂)₄—, —(CH₂)₅—, —(CH₂)₂—O—(CH₂)₂—, —(CH₂)₂—S—(CH₂)₂—, —(CH₂)₂—NR—(CH₂)₂—, —(CH₂)₂—C(O)—(CH₂)₂—, —(CH₂)₂—CF₂—(CH₂)₂—, —CH₂—CHR—(CH₂)₂, —CHR—(CH₂)₃, —CHR—(CH₂)₂—CHR—, or is the ring 2,6-diaza-spiro[3.3]heptane-2-carboxylic acid tert-butyl ester and R is hydroxy, halogen, cycloalkyl, or C(O)O-lower alkyl;
X is —(CH₂)₄—, —(CH₂)₃—, —(CH₂)₂— or —CH₂—;
R³ is S-lower alkyl, CF₃, OCHF₂, lower alkoxy, lower alkyl, phenyl, cycloalkyl or halogen;
R⁴ is CF₃, lower alkoxy, lower alkyl, or halogen and n is 1 or 2;
or a pharmaceutically acceptable acid addition salt, racemic mixture, or corresponding enantiomers and/or optical isomers thereof.

Furthermore, the present invention provides new compounds of formulas IA and IB, which are encompassed by formula I, for example the following compounds:
Compounds of formula IA:

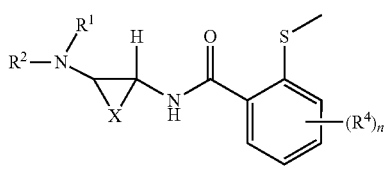

IA wherein
R¹ and R² are each independently hydrogen, lower alkyl, —(CH₂)ₒ-cycloalkyl wherein o is 0 or 1, or are benzyl or heterocycloalkyl;
or R¹ and R² together with the N-atom to which they are attached form a ring containing —(CH₂)₃—, —(CH₂)₄—, —(CH₂)₅—, —(CH₂)₂—O—(CH₂)₂—, —(CH₂)₂—S—(CH₂)₂—, —(CH₂)₂—NR—(CH₂)₂—, —(CH₂)₂—C(O)—(CH₂)₂—, —(CH₂)₂—CF₂—(CH₂)₂—, —CH₂—CHR—(CH₂)₂, —CHR—(CH₂)₃, —CHR—(CH₂)₂—CHR—, or is the ring 2,6-diaza-spirp[3.3]heptane-2-carboxylic acid tert-butyl ester and R is hydroxy, halogen, cycloalkyl, or C(O)O-lower alkyl;
X is —(CH₂)₄—, —(CH₂)₃—, —(CH₂)₂— or —CH₂—;
R⁴ is CF₃, lower alkoxy, lower alkyl, or halogen and n is 1 or 2;
or a pharmaceutically acceptable acid addition salt, a racemic mixture, or its corresponding enantiomers and/or optical isomers thereof.

Compounds of formula IA-1:

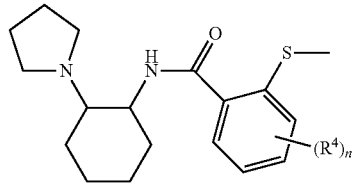

IA-1 wherein
R⁴ is CF₃, lower alkoxy, lower alkyl, or halogen and n is 1 or 2;
or a pharmaceutically acceptable acid addition salt, a racemic mixture, or its corresponding enantiomers and/or optical isomers thereof.

Examples for compounds of formula IA-1 are
cis-2-methoxy-6-methylsulfanyl-N-2-pyrrolidin-1-yl-cyclohexyl)-4-trifluoromethyl-benzamide;
cis-2-methylsulfanyl-N-(2-pyrrolidin-1-yl-cyclohexyl)-4-trifluoromethyl-benzamide;
(−)-cis-2-methoxy-6-methylsulfanyl-N-(2-pyrrolidin-1-yl-cyclohexyl)-4-trifluoromethyl-benzamide;
(+)-cis-2-methoxy-6-methylsulfanyl-N-(2-pyrrolidin-1-yl-cyclohexyl)-4-trifluoromethyl-benzamide;
(−)-cis-2-methylsulfanyl-N-(2-pyrrolidin-1-yl-cyclohexyl)-4-trifluoromethyl-benzamide;
2-methylsulfanyl-N-((cis-2-pyrrolidin-1-yl-cyclohexyl)-4,6-bis-trifluoromethyl-benzamide; and
(+)-2-methylsulfanyl-N-((cis)-2-pyrrolidin-1-yl-cyclohexyl)-4,6-bis-trifluoromethyl-benzamide.

Compounds of formula IA-2:

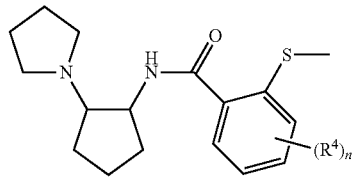

IA-2 wherein
R⁴ is CF₃, lower alkoxy, lower alkyl, or halogen and n is 1 or 2;
or a pharmaceutically acceptable acid addition salt, a racemic mixture, or its corresponding enantiomers and/or optical isomers thereof, for example the following compounds:
2-Methoxy-6-methylsulfanyl-N-((1RS,2SR)-2-pyrrolidin-1-yl-cyclopentyl)-4-trifluoromethyl-benzamide;
(−)-2-methoxy-6-methylsulfanyl-N-(2-pyrrolidin-1-yl-cyclopentyl)-4-trifluoromethyl-benzamide;
(+)-2-methoxy-6-methylsulfanyl-N-(2-pyrrolidin-1-yl-cyclopentyl)-4-trifluoromethyl-benzamide;
(+)-2-methylsulfanyl-N-(2-pyrrolidin-1-yl-cyclopentyl)-4-trifluoromethyl-benzamide;
(−)-2-methylsulfanyl-N-(2-pyrrolidin-1-yl-cyclopentyl)-4-trifluoromethyl-benzamide;
cis-2-methylsulfanyl-N-(2-pyrrolidin-1-yl-cyclopentyl)-4,6-bis-trifluoromethyl-benzamide;
(+)-cis-2-methylsulfanyl-N-(2-pyrrolidin-1-yl-cyclopentyl)-4,6-bis-trifluoromethyl-benzamide; and (−)-cis-2-methylsulfanyl-N-(2-pyrrolidin-1-yl-cyclopentyl)-4,6-bis-trifluoromethyl-benzamide.

Compounds of formula IA-3:

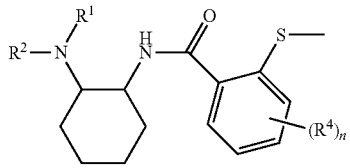

wherein $R^1$ and $R^2$ are each independently hydrogen, lower alkyl, —$(CH_2)_o$-cycloalkyl wherein o is 0 or 1, or are benzyl or heterocycloalkyl;

$R^4$ is $CF_3$, lower alkoxy, lower alkyl, or halogen and n is 1 or 2;

or a pharmaceutically acceptable acid addition salt, a racemic mixture, or its corresponding enantiomers and/or optical isomers thereof, for example the following compounds:

cis-N-(2-cyclobutylamino-cyclohexyl)-2-methoxy-6-methylsulfanyl-4-trifluoromethyl-benzamide;

N-((1RS,2SR)-2-cyclopentylamino-cyclohexyl)-2-methoxy-6-methylsulfanyl-4-trifluoromethyl-benzamide; and (+)-N-(2-cyclopentylamino-cyclohexyl)-2-methoxy-6-methylsulfanyl-4-trifluoromethyl-benzamide.

Compounds of formula IA-4:

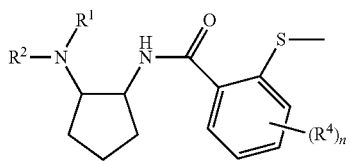

wherein $R^1$ and $R^2$ are each independently hydrogen, lower alkyl, —$(CH_2)_o$-cycloalkyl wherein o is 0 or 1, or are benzyl or heterocycloalkyl;

$R^4$ is $CF_3$, lower alkoxy, lower alkyl, or halogen and n is 1 or 2;

or a pharmaceutically acceptable acid addition salt, a racemic mixture, or its corresponding enantiomers and/or optical isomers thereof, for example the following compounds:

N-((1RS,2SR)-2-cyclobutylamino-cyclopentyl)-2-methoxy-6-methylsulfanyl-4-trifluoromethyl-benzamide;

(−)-cis-N+2-cyclobutylamino-cyclopentyl)-2-methoxy-6-methylsulfanyl-4-trifluoromethyl-benzamide;

N-((1RS,2SR)-2-cyclopentylamino-cyclopentyl)-2-methoxy-6-methylsulfanyl-4-trifluoromethyl-benzamide;

(−)-N-(2-cyclopentylamino-cyclopentyl)-2-methoxy-6-methylsulfanyl-4-trifluoromethyl-benzamide; and N-((cis)-2-cyclopentylamino-cyclopentyl)-2-methylsulfanyl-4,6-bis-trifluoromethyl-benzamide.

Compounds of formula IB:

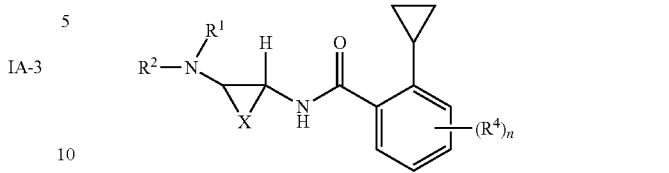

wherein $R^1$ and $R^2$ are each independently hydrogen, lower alkyl, —$(CH_2)_o$-cycloalkyl wherein o is 0 or 1, or are benzyl or heterocycloalkyl;

or $R^1$ and $R^2$ together with the N-atom to which they attached form a ring containing —$(CH_2)_3$—, —$(CH_2)_4$—, —$(CH_2)_5$—, —$(CH_2)_2$—O—$(CH_2)_2$—, —$(CH_2)_2$—S—$(CH_2)_2$—, —$(CH_2)_2$—NR—$(CH_2)_2$—, —$(CH_2)_2$—C(O)—$(CH_2)_2$—, —$(CH_2)_2$—$CF_2$—$(CH_2)_2$—, —$CH_2$—CHR—$(CH_2)_2$, —CHR—$(CH_2)_3$, CHR—$(CH_2)_2$—CHR—, or is the ring 2,6-diaza-spirp[3.3]heptane-2-carboxylic acid tert-butyl ester and R is hydroxy, halogen, cycloalkyl, or C(O)O-lower alkyl;

X is —$(CH_2)_4$—, —$(CH_2)_3$—, —$(CH_2)_2$— or —$CH_2$—;

$R^4$ is $CF_3$, lower alkoxy, lower alkyl, or halogen and n is 1 or 2;

or a pharmaceutically acceptable acid addition salt, a racemic mixture, or its corresponding enantiomers and/or optical isomers thereof.

Compounds of formula IB-1:

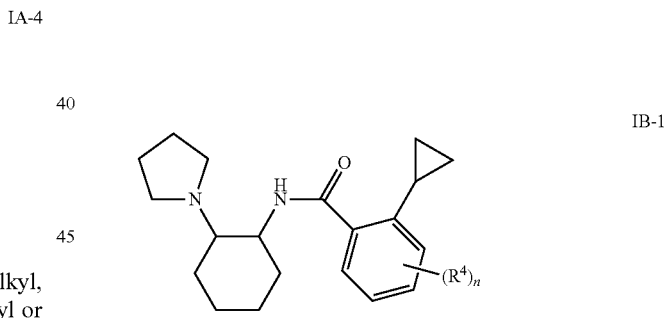

wherein $R^4$ is $CF_3$, lower alkoxy, lower alkyl, or halogen and n is 1 or 2;

or a pharmaceutically acceptable acid addition salt, a racemic mixture, or its corresponding enantiomers and/or optical isomers thereof.

Examples for Compounds of formula IB-1 are cis-2-cyclopropyl-N-(2-pyrrolidin-1-yl-cyclohexyl)-4-trifluoromethyl-benzamide;

(−)-cis-2-cyclopropyl-N-(2-pyrrolidin-1-yl-cyclohexyl)-4-trifluoromethyl-benzamide;

(+)-cis-2-cyclopropyl-N-(2-pyrrolidin-1-yl-cyclohexyl)-4-trifluoromethyl-benzamide; and 2-Cyclopropyl-N-((cis)-2-pyrrolidin-1-yl-cyclohexyl)-4,6-bis-trifluoromethyl-benzamide.

Compounds of formula IB-2:

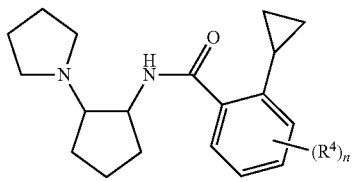

wherein
R⁴ is CF₃, lower alkoxy, lower alkyl, or halogen and
n is 1 or 2;
or a pharmaceutically acceptable acid addition salt, a racemic mixture, or its corresponding enantiomers and/or optical isomers thereof, for example the following compounds:
2-cyclopropyl-cis-N-(2-pyrrolidin-1-yl-cyclopentyl)-4-trifluoromethyl-benzamide;
(−)-2-cyclopropyl-N-cis-(-2-pyrrolidin-1-yl-cyclopentyl)-4-trifluoromethyl-benzamide; and
(+)-2-cyclopropyl-N-cis-(-2-pyrrolidin-1-yl-cyclopentyl)-4-trifluoromethyl-benzamide;
cis-2-cyclopropyl-6-ethyl-N-(2-pyrrolidin-1-yl-cyclopentyl)-benzamide;
(−)-cis-2-cyclopropyl-6-ethyl-N-(2-pyrrolidin-1-yl-cyclopentyl)-benzamide;
(+)-cis-2-cyclopropyl-6-ethyl-N-(2-pyrrolidin-1-yl-cyclopentyl)-benzamide;
2-cyclopropyl-N-((cis)-2-pyrrolidin-1-yl-cyclopentyl)-4,6-bis-trifluoromethyl-benzamide;
2-cyclopropyl-6-methoxy-N-((cis)-2-pyrrolidin-1-yl-cyclopentyl)-4 trifluoromethyl-benzamide;
(−)-2-cyclopropyl-N-((1R,2S or 1S,2R)-2-pyrrolidin-1-yl-cyclopentyl)-4,6-bis-trifluoromethyl-benzamide; and
(+)-2-cyclopropyl-N-((1R,2S or 1S,2R)-2-pyrrolidin-1-yl-cyclopentyl)-4,6-bis-trifluoromethyl-benzamide.

Compounds of formula IB-3:

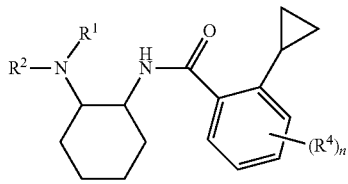

wherein
R¹ and R² are each independently hydrogen, lower alkyl, —CH₂)ₒ-cycloalkyl wherein o is 0 or 1, or are benzyl or heterocycloalkyl;
R⁴ is CF₃, lower alkoxy, lower alkyl, or halogen and
n is 1 or 2;
or a pharmaceutically acceptable acid addition salt, a racemic mixture, or its corresponding enantiomers and/or optical isomers thereof, for example the following compounds:
cis-N-(2-cyclopentylamino-cyclohexyl)-2-cyclopropyl-4-trifluoromethyl-benzamide;
(−)-N-cis-(2-cyclopentylamino-cyclohexyl)-2-cyclopropyl-4-trifluoromethyl-benzamide; and
(+)-N-cis-(2-cyclopentylamino-cyclohexyl)-2-cyclopropyl-4-trifluoromethyl-benzamide.

Compounds of formula IB-4:

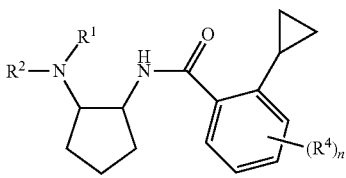

wherein
R¹ and R² are each independently hydrogen, lower alkyl, —CH₂)ₒ-cycloalkyl wherein o is 0 or 1, or are benzyl or heterocycloalkyl;
R⁴ is CF₃, lower alkoxy, lower alkyl, or halogen and
n is 1 or 2;
or a pharmaceutically acceptable acid addition salt, a racemic mixture, or its corresponding enantiomers and/or optical isomers thereof, for example the following compounds:
N-((1SR,2RS)-2-cyclopentylamino-cyclopentyl)-2-cyclopropyl-4-trifluoromethyl-benzamide;
(+)-cis-N-2-cyclopentylamino-cyclopentyl)-2-cyclopropyl-4-trifluoromethyl-benzamide; or
(−)-cis-N-2-cyclopentylamino-cyclopentyl)-2-cyclopropyl-4-trifluoromethyl-benzamide.

Further new compounds of formula I

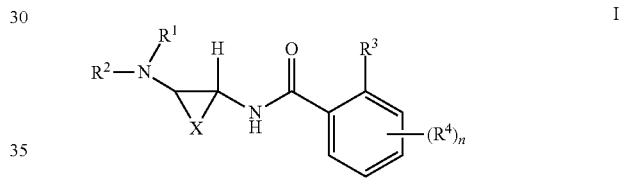

are
cis-2-ethyl-N-(2-pyrrolidin-1-yl-cyclohexyl)-4-trifluoromethyl-benzamide;
N-((1RS,2SR)-2-Cyclopentylamino-cyclohexyl)-2-methoxy-4,6-bis-trifluoromethyl-benzamide;
cis-2-methoxy-N-[2-(2-methyl-pyrrolidin-1-yl)-cyclohexyl]-4,6-bis-trifluoromethyl-benzamide (mixture of 2 diastereomers);
2-methyl-N-((cis-2-pyrrolidin-1-yl-cyclohexyl)-4,6-bis-trifluoromethyl-benzamide;
(−)-N-(2-pyrrolidin-1-yl-cyclopentyl)-2,4-bis-trifluoromethyl-benzamide;
cis-2-ethyl-N-(2-pyrrolidin-1-yl-cyclopentyl)-4-trifluoromethyl-benzamide;
cis-N-(2-cyclopentylamino-cyclopentyl)-2-ethyl-4-trifluoromethyl-benzamide;
(+)-N-(2-cyclopentylamino-cyclopentyl)-2-ethyl-4-trifluoromethyl-benzamide;
cis-2-ethyl-6-methyl-N-(2-pyrrolidin-1-yl-cyclopentyl)-benzamide;
2-bromo-6-methoxy-N-cis-(2-pyrrolidin-1-yl-cyclopentyl)-4-trifluoromethyl-benzamide;
cis-2-methyl-N-(2-pyrrolidin-1-yl-cyclopentyl)-4,6-bis-trifluoromethyl-benzamide;
cis-2-fluoro-N-(2-pyrrolidin-1-yl-cyclopentyl)-4,6-bis-trifluoromethyl-benzamide;
cis-2,6-dichloro-N-(2-pyrrolidin-1-yl-cyclopentyl)-4-trifluoromethyl-benzamide;
(−)-2-bromo-6-methoxy-N-cis-(2-pyrrolidin-1-yl-cyclopentyl)-4-trifluoromethyl-benzamide;

(+)-2-bromo-6-methoxy-N-cis-(2-pyrrolidin-1-yl-cyclopentyl)-4-trifluoromethyl-benzamide;
(+)-2,6-dichloro-N-cis-(2-pyrrolidin-1-yl-cyclopentyl)-4-trifluoromethyl-benzamide;
(−)-2,6-dichloro-N-cis-(2-pyrrolidin-1-yl-cyclopentyl)-4-trifluoromethyl-benzamide;
2,6-dimethyl-N-((cis)-2-pyrrolidin-1-yl-cyclopentyl)-4-trifluoromethyl-benzamide;
2-difluoromethoxy-6-methoxy-N-((cis)-2-pyrrolidin-1-yl-cyclopentyl)-4-trifluoromethyl-benzamide;
2-ethyl-N-((cis)-2-pyrrolidin-1-yl-cyclopentyl)-4,6-bis-trifluoromethyl-benzamide;
2-ethyl-6-methoxy-N-((cis)-2-pyrrolidin-1-yl-cyclopentyl)-4-trifluoromethyl-benzamide;
(+)-2-ethyl-N-(2-pyrrolidin-1-yl-cyclopentyl)-4,6-bis-trifluoromethyl-benzamide; and
(−)-2-ethyl-N-(2-pyrrolidin-1-yl-cyclopentyl)-4,6-bis-trifluoromethyl-benzamide.

The following compounds of formula I are preferred and can be used for the treatment of psychoses, pain, dysfunction in memory and learning, attention deficit, schizophrenia, dementia disorders or Alzheimer's disease:
cis-2-methoxy-6-methylsulfanyl-N-2-pyrrolidin-1-yl-cyclohexyl)-4-trifluoromethyl-benzamide;
cis-2-methylsulfanyl-N-(2-pyrrolidin-1-yl-cyclohexyl)-4-trifluoromethyl-benzamide;
(−)-cis-2-methoxy-6-methylsulfanyl-N-(2-pyrrolidin-1-yl-cyclohexyl)-4-trifluoromethyl-benzamide;
(+)-cis-2-methoxy-6-methylsulfanyl-N-(2-pyrrolidin-1-yl-cyclohexyl)-4-trifluoromethyl-benzamide;
(−)-cis-2-methylsulfanyl-N-(2-pyrrolidin-1-yl-cyclohexyl)-4-trifluoromethyl-benzamide;
2-methylsulfanyl-N-((cis-2-pyrrolidin-1-yl-cyclohexyl)-4,6-bis-trifluoromethyl-benzamide;
2-Methoxy-6-methylsulfanyl-N-((1RS,2RS)-2-pyrrolidin-1-yl-cyclopentyl)-4-trifluoromethyl-benzamide;
(−)-2-methoxy-6-methylsulfanyl-N-(2-pyrrolidin-1-yl-cyclopentyl)-4-trifluoromethyl-benzamide;
(+)-2-methoxy-6-methylsulfanyl-N-(2-pyrrolidin-1-yl-cyclopentyl)-4-trifluoromethyl-benzamide;
(+)-2-methylsulfanyl-N-(2-pyrrolidin-1-yl-cyclopentyl)-4-trifluoromethyl-benzamide;
(−)-2-methylsulfanyl-N-(2-pyrrolidin-1-yl-cyclopentyl)-4-trifluoromethyl-benzamide;
cis-2-methylsulfanyl-N-(2-pyrrolidin-1-yl-cyclopentyl)-4,6-bis-trifluoromethyl-benzamide;
(+)-cis-2-methylsulfanyl-N-(2-pyrrolidin-1-yl-cyclopentyl)-4,6-bis-trifluoromethyl-benzamide;
(−)-cis-2-methylsulfanyl-N-(2-pyrrolidin-1-yl-cyclopentyl)-4,6-bis-trifluoromethyl-benzamide;
cis-N-(2-cyclobutylamino-cyclohexyl)-2-methoxy-6-methylsulfanyl-4-trifluoromethyl-benzamide;
N-((1RS,2SR)-2-cyclopentylamino-cyclohexyl)-2-methoxy-6-methylsulfanyl-4-trifluoromethyl-benzamide;
(+)-N-(2-cyclopentylamino-cyclohexyl)-2-methoxy-6-methylsulfanyl-4-trifluoromethyl-benzamide;
N-((1RS,2SR)-2-cyclobutylamino-cyclopentyl)-2-methoxy-6-methylsulfanyl-4-trifluoromethyl-benzamide;
(−)-cis-N-(-2-cyclobutylamino-cyclopentyl)-2-methoxy-6-methylsulfanyl-4-trifluoromethyl-benzamide;
N-((1RS,2SR)-2-cyclopentylamino-cyclopentyl)-2-methoxy-6-methylsulfanyl-4-trifluoromethyl-benzamide;
(−)-N-(2-cyclopentylamino-cyclopentyl)-2-methoxy-6-methylsulfanyl-4-trifluoromethyl-benzamide;
cis-2-cyclopropyl-N-(2-pyrrolidin-1-yl-cyclohexyl)-4-trifluoromethyl-benzamide;
(−)-cis-2-cyclopropyl-N-(2-pyrrolidin-1-yl-cyclohexyl)-4-trifluoromethyl-benzamide;
(+)-cis-2-cyclopropyl-N-(2-pyrrolidin-1-yl-cyclohexyl)-4-trifluoromethyl-benzamide;
2-cyclopropyl-cis-N-(2-pyrrolidin-1-yl-cyclopentyl)-4-trifluoromethyl-benzamide;
(−)-2-cyclopropyl-N-cis-(-2-pyrrolidin-1-yl-cyclopentyl)-4-trifluoromethyl-benzamide; and
(+)-2-cyclopropyl-N-cis-(-2-pyrrolidin-1-yl-cyclopentyl)-4-trifluoromethyl-benzamide;
cis-2-cyclopropyl-6-ethyl-N-(2-pyrrolidin-1-yl-cyclopentyl)-benzamide;
(−)-cis-2-cyclopropyl-6-ethyl-N-(2-pyrrolidin-1-yl-cyclopentyl)-benzamide;
(+)-cis-2-cyclopropyl-6-ethyl-N-(2-pyrrolidin-1-yl-cyclopentyl)-benzamide;
cis-N-(2-cyclopentylamino-cyclohexyl)-2-cyclopropyl-4-trifluoromethyl-benzamide;
(−)-N-cis-(2-cyclopentylamino-cyclohexyl)-2-cyclopropyl-4-trifluoromethyl-benzamide;
(+)-N-cis-(2-cyclopentylamino-cyclohexyl)-2-cyclopropyl-4-trifluoromethyl-benzamide;
N-((1SR,2RS)-2-cyclopentylamino-cyclopentyl)-2-cyclopropyl-4-trifluoromethyl-benzamide;
(+)-cis-N-2-cyclopentylamino-cyclopentyl)-2-cyclopropyl-4-trifluoromethyl-benzamide;
(−)-cis-N-2-cyclopentylamino-cyclopentyl)-2-cyclopropyl-4-trifluoromethyl-benzamide;
cis-2-ethyl-N-(2-pyrrolidin-1-yl-cyclohexyl)-4-trifluoromethyl-benzamide;
N-((1RS,2SR)-2-Cyclopentylamino-cyclohexyl)-2-methoxy-4,6-bis-trifluoromethyl-benzamide;
cis-2-methoxy-N-[2-(2-methyl-pyrrolidin-1-yl)-cyclohexyl]-4,6-bis-trifluoromethyl-benzamide (mixture of 2 diastereomers);
2-methyl-N-((cis-2-pyrrolidin-1-yl-cyclohexyl)-4,6-bis-trifluoromethyl-benzamide;
(−)-N-(2-pyrrolidin-1-yl-cyclopentyl)-2,4-bis-trifluoromethyl-benzamide;
cis-2-ethyl-N-(2-pyrrolidin-1-yl-cyclopentyl)-4-trifluoromethyl-benzamide;
cis-N-(2-cyclopentylamino-cyclopentyl)-2-ethyl-4-trifluoromethyl-benzamide;
(+)-N-(2-cyclopentylamino-cyclopentyl)-2-ethyl-4-trifluoromethyl-benzamide;
cis-2-ethyl-6-methyl-N-(2-pyrrolidin-1-yl-cyclopentyl)-benzamide;
2-bromo-6-methoxy-N-cis-(2-pyrrolidin-1-yl-cyclopentyl)-4-trifluoromethyl-benzamide;
cis-2-methyl-N-(2-pyrrolidin-1-yl-cyclopentyl)-4,6-bis-trifluoromethyl-benzamide;
cis-2-fluoro-N-(2-pyrrolidin-1-yl-cyclopentyl)-4,6-bis-trifluoromethyl-benzamide;
cis-2,6-dichloro-N-(2-pyrrolidin-1-yl-cyclopentyl)-4-trifluoromethyl-benzamide;
(−)-2-bromo-6-methoxy-N-cis-(2-pyrrolidin-1-yl-cyclopentyl)-4-trifluoromethyl-benzamide;
(+)-2-bromo-6-methoxy-N-cis-(2-pyrrolidin-1-yl-cyclopentyl)-4-trifluoromethyl-benzamide;
(−)-cis-2-fluoro-N-(2-pyrrolidin-1-yl-cyclopentyl)-4,6-bis-trifluoromethyl-benzamide;
(+)-2-methylsulfanyl-N-((cis)-2-pyrrolidin-1-yl-cyclohexyl)-4,6-bis-trifluoromethyl-benzamide;
(+)-2,6-dichloro-N-cis-(2-pyrrolidin-1-yl-cyclopentyl)-4-trifluoromethyl-benzamide;
(−)-2,6-dichloro-N-cis-(2-pyrrolidin-1-yl-cyclopentyl)-4-trifluoromethyl-benzamide;

2-cyclopropyl-N-((cis)-2-pyrrolidin-1-yl-cyclopentyl)-4,6-bis-trifluoromethyl-benzamide;
2-cyclopropyl-6-methoxy-N-((cis)-2-pyrrolidin-1-yl-cyclopentyl)-4 trifluoromethyl-benzamide;
2,6-dimethyl-N-((cis)-2-pyrrolidin-1-yl-cyclopentyl)-4-trifluoromethyl-benzamide;
2-difluoromethoxy-6-methoxy-N-((cis)-2-pyrrolidin-1-yl-cyclopentyl)-4-trifluoromethyl-benzamide;
N-((cis)-2-cyclopentylamino-cyclopentyl)-2-methylsulfanyl-4,6-bis-trifluoromethyl-benzamide;
2-cyclopropyl-N-((cis)-2-pyrrolidin-1-yl-cyclohexyl)-4,6-bis-trifluoromethyl-benzamide;
2-ethyl-N-((cis)-2-pyrrolidin-1-yl-cyclopentyl)-4,6-bis-trifluoromethyl-benzamide;
(−)-2-cyclopropyl-N-((1R,2S or 1S,2R)-2-pyrrolidin-1-yl-cyclopentyl)-4,6-bis-trifluoromethyl-benzamide;
(+)-2-cyclopropyl-N-((1R,2S or 1S,2R)-2-pyrrolidin-1-yl-cyclopentyl)-4,6-bis-trifluoromethyl-benzamide;
2-ethyl-6-methoxy-N-((cis)-2-pyrrolidin-1-yl-cyclopentyl)-4-trifluoromethyl-benzamide;
(+)-2-ethyl-N-(2-pyrrolidin-1-yl-cyclopentyl)-4,6-bis-trifluoromethyl-benzamide; and
(−)-2-Ethyl-N-(2-pyrrolidin-1-yl-cyclopentyl)-4,6-bis-trifluoromethyl-benzamide.

Compounds of formula I are good inhibitors of the glycine transporter 1 (GlyT-1), and that they have a good selectivity to glycine transporter 2 (GlyT-2) inhibitors.

The present invention, thus, provides compounds of formulas IA and IB per se and their pharmaceutically acceptable salts, pharmaceutical compositions containing such compounds, and methods for the preparation of the compounds and compositions of the invention. The invention also provides methods for the treatment of diseases related to activation of NMDA receptors via Glyt-1 inhibition, for example the treatment of illnesses such as psychoses, dysfunction in memory and learning, schizophrenia, dementia and other diseases in which cognitive processes are impaired, such as attention deficit disorders or Alzheimer's disease. with compounds of formula I and their pharmaceutically acceptable salts. The invention further provides methods for the manufacture of compounds of formula I.

The preferred indications of the present invention are schizophrenia, cognitive impairment and Alzheimer's disease.

Furthermore, the invention includes all racemic mixtures, all their corresponding enantiomers and/or optical isomers.

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is linked with an O atom.

The term "cycloalkyl" denotes a saturated or partially saturated ring containing from 3 to 7 carbon atoms, for example cyclopropyl, cyclobutyl, cyclopentyl, cyclopentenyl, cyclohexyl, cyclohexenyl, cycloheptyl or cycloheptenyl. Preferred cycloalkyl rings are cyclopropyl and cyclopentyl.

The term "heterocycloalkyl" denotes a saturated or partially saturated ring containing from 3 to 6 ring atoms, wherein at least one ring atom is a heteroatom selected from N, S and O, and the rest of the ring atoms are carbon, for example piperazinyl, morpholinyl, piperidinyl or tetrahydropyranyl.

The term "halogen" denotes chlorine, iodine, fluorine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present compounds of formula I and their pharmaceutically acceptable salts can be prepared by methods known in the art, for example, by processes described below, which process comprises a) reacting a compound of formula

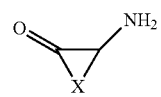

with an acid of formula

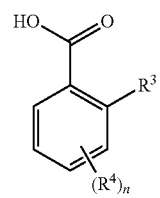

in the presence of an activating agent such as HATU (o-(7-azabenzotriazol-1-yl)-1,1,3,3-tetramethyluronium hexafluorophosphate)

to give a compound of formula

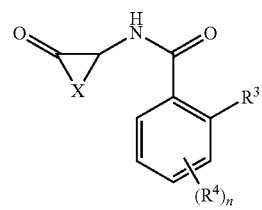

and reductively aminating the obtained compound with an amine of formula $NHR^1R^2$ to give the compound of formula

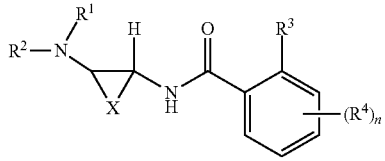

wherein the substituents are as defined above, or
  b) reacting a compound of formula

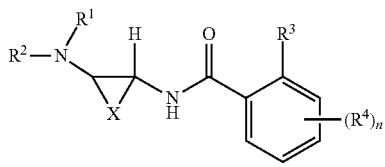

(for $R^1$ and $R^2$ being H)
with a corresponding di-bromo alkyl or heteroalkyl compound to a compound of formula

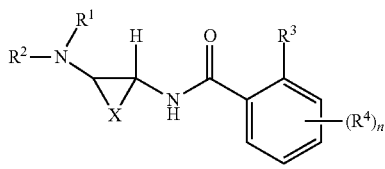

wherein $R^1$ and $R^2$ together with the N-atom to which they are attached form a ring containing —$(CH_2)_3$—, —$(CH_2)_4$—, —$(CH_2)_5$—, —$(CH_2)_2$—O—$(CH_2)_2$—, —$(CH_2)_2$—S—$(CH_2)_2$—, —$(CH_2)_2$—NR—$(CH_2)_2$—, —$(CH_2)_2$—C(O)—$(CH_2)_2$—, —$(CH_2)_2$—CF$_2$—$(CH_2)_2$—, —$CH_2$—CHR—$(CH_2)_2$, —CHR—$(CH_2)_3$, CHR—$(CH_2)_2$—CHR—, or is the ring 2,6-diaza-spirp[3.3]heptane-2-carboxylic acid tert-butyl ester and R is hydroxy, halogen, cycloalkyl, or C(O)O-lower alkyl and the other substituents are as described above, and,
if desired, converting the compounds obtained into pharmaceutically acceptable acid addition salts.

The compounds of formula I can be prepared in accordance with process variant a) or b) and with the following schemes 1-14. The starting material is commercially available or can be prepared in accordance with known methods.
General Synthesis Scheme 1

This scheme leads to compounds of formula I, wherein X is

—$(CH_2)_4$— .

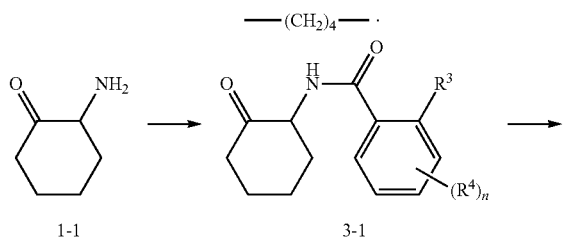

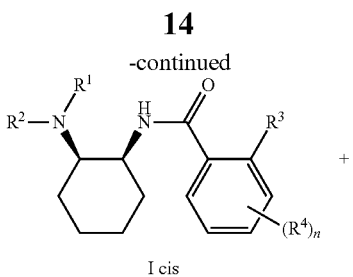

I cis

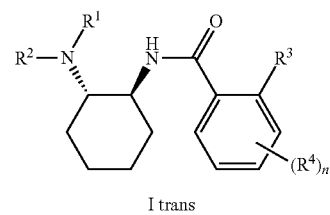

I trans

2-Amino-cyclohexanone 1-1 (CAS 6946-05-0) is coupled with an acid using the coupling agent O-(7-azabenzotriazol-1-yl)-N,N,N',N'-tetramethyluronium hexafluorophosphate (=HATU) in dimethylformamide to obtain amide 3-1. Reductive amination gives a mixture of cis- and trans-compounds of formulas I which can be separated by column chromatography.

Scheme 2

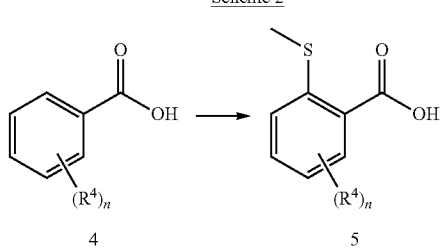

Some acids are prepared according to scheme 2: Acids 4 are deprotonated with sec-butyllithium/N,N,N'N'-tetramethylethylendiamine complex at −70° C. in THF. Quenching with dimethyl disulfide gives ortho-methylsulfanyl benzoic acids 5.

Scheme 3

This scheme leads to compounds of formula I, wherein X is

—$(CH_2)_4$— and $R^1$ and $R^2$ together with the N-atom to which they are attached form a ring containing —$(CH_2)_4$— .

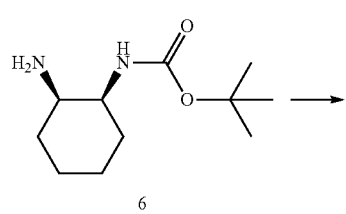

-continued

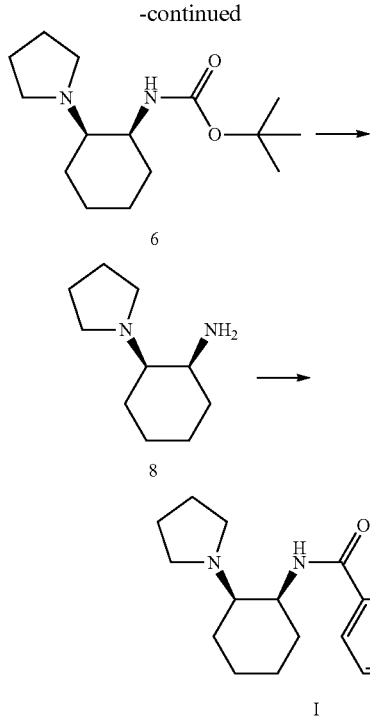

1-N-Boc-1,2-cis-cyclohexyldiamine 6 (CAS 184954-75-4) is reacted with 1,4-dibromobutane to the pyrrolidine 7. The Boc-protecting group is cleaved with HCl in dioxane to yield building block 8 which is coupled with different acids using the coupling agent O-(7-azabenzotriazol-1-yl)-N,N,N',N'-tetramethyluronium hexafluorophosphate (=HATU) in dimethylformamide to obtain amide I.

Scheme 4

This scheme leads to compounds of formula I, wherein X is
—(CH$_2$)$_4$—.

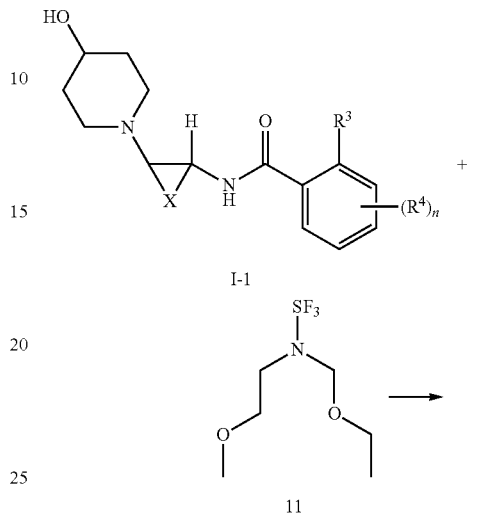

1,2-cis-Cyclohexyldiamine 9 is coupled with different acids using the coupling agent O-(7-azabenzotriazol-1-yl)-N,N,N',N'-tetramethyluronium hexafluorophosphate (=HATU) in dimethylformamide to obtain amide 10. The free amine group in 10 is alkylated with alkylbromides or with aldehydes or ketones using reductive aminations to produce the final compounds I.

Scheme 5

An alcohol I-1 or a ketone I-3 is reacted with bis(2-methoxyethyl)aminosulfur trifluoride (11) to obtain fluorides I-2 or I-4.

Scheme 6

This scheme leads to compounds of formula I, wherein X is

—(CH$_2$)$_4$—.

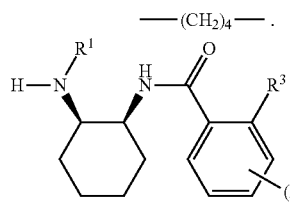

I for R$^2$ = H

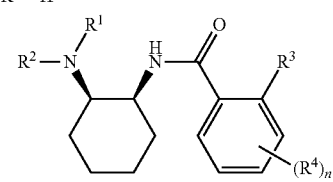

I

Amine is reductively aminated to produce the final compounds I. In case of R$^2$=CH$_3$ a mixture of aqueous formaldehyde in formic acid is used.

Scheme 7

This scheme leads to compounds of formula I, wherein X is

—(CH$_2$)$_3$—.

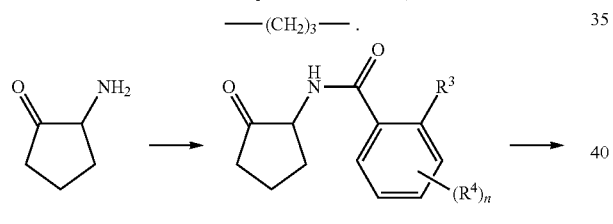

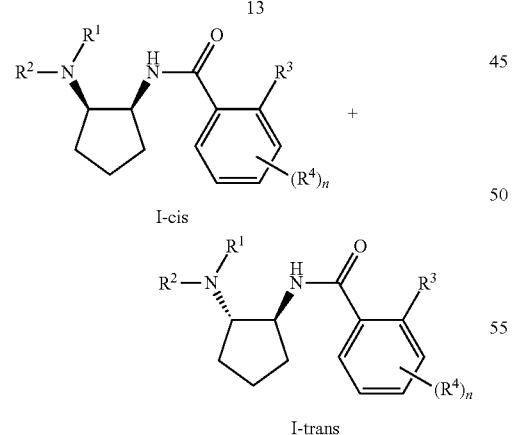

I-trans

2-Amino-cyclopentanone dihydrochloride 12 (CAS 5464-16-4) is coupled with an acid using the coupling agent O-(7-azabenzotriazol-1-yl)-N,N,N',N'-tetramethyluronium hexafluorophosphate (=HATU) in dimethylformamide to obtain amide 13. Reductive amination gives a mixture of cis and trans-compounds of formulas I, which can be separated by column chromatography.

Scheme 8

This scheme leads to compounds of formula I, wherein X is

—(CH$_2$)$_3$—.

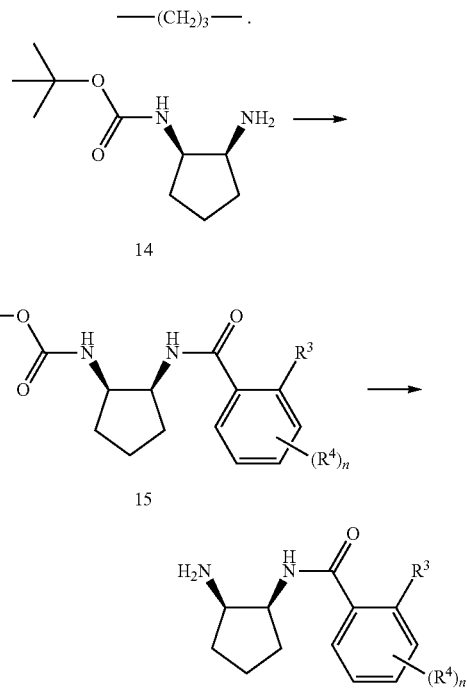

I for R$^1$/R$^2$ = H

[(1RS,2SR)-2-aminocyclopentyl-carbamic acid 1,1-dimethylethyl ester (CAS 365996-19-6) 14 is coupled with different acids using the coupling agent O-(7-azabenzotriazol-1-yl)-N,N,N',N'-tetramethyluronium hexafluorophosphate (=HATU) in dimethylformamide to obtain amide 15. The Boc-protecting group is cleaved with hydrochloric acid in dioxane to yield I for R$^1$/R$^2$ being H.

Scheme 9

This scheme leads to compounds of formula I, wherein X is

—(CH$_2$)$_3$— and R$^1$/R$^2$ form together a pyrrolidine ring.

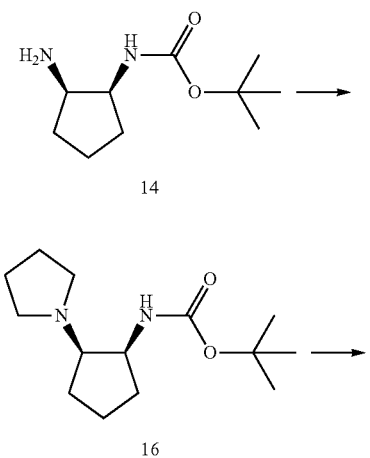

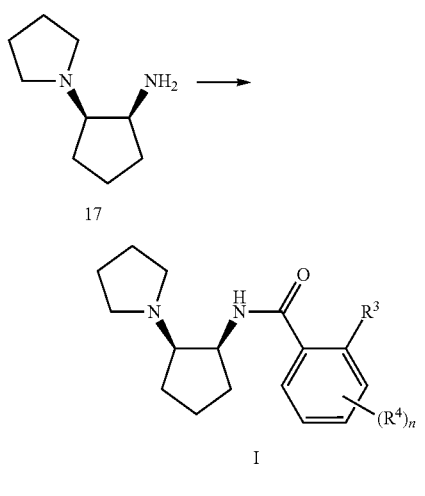

[(1RS,2SR)-2-aminocyclopentyl-carbamic acid 1,1-dimethylethyl ester 14 (CAS 365996-19-6) is reacted with 1,4-dibromobutane to the pyrrolidine 16. The Boc-protecting group is cleaved with HCl in dioxane to yield building block 17 which is coupled with different acids using the coupling agent O-(7-azabenzotriazol-1-yl)-N,N,N',N'-tetramethyluronium hexafluorophosphate (=HATU) in dimethylformamide to obtain amide I.

Scheme 10

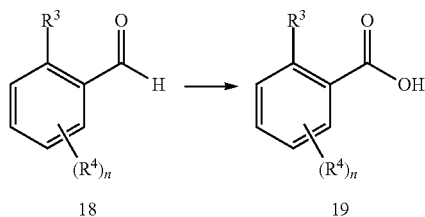

Some acids are prepared according to scheme 10: Aldehyde 18 is oxidized with a mixture of sodium chlorite and sodium dihydrogenphosphate in tert butanol and 2-methyl-2-butene to yield acid 19.

Scheme 11

This scheme leads to compounds of formula I, wherein X is
——(CH$_2$)$_2$—— and R$^1$/R$^2$ form together a pyrrolidine ring.

(2-Oxo-cyclobutyl)-carbamic acid benzyl ester 20 (CAS 406951-43-7) is reacted with pyrrolidine in a reductive amination to yield 21. The protecting group is cleaved with hydrogenation to yield building block 22 which is coupled with different acids using the coupling agent O-(7-azabenzotriazol-1-yl)-N,N,N',N'-tetramethyluronium hexafluorophosphate (=HATU) in dimethylformamide to obtain amide I-5.

Scheme 12

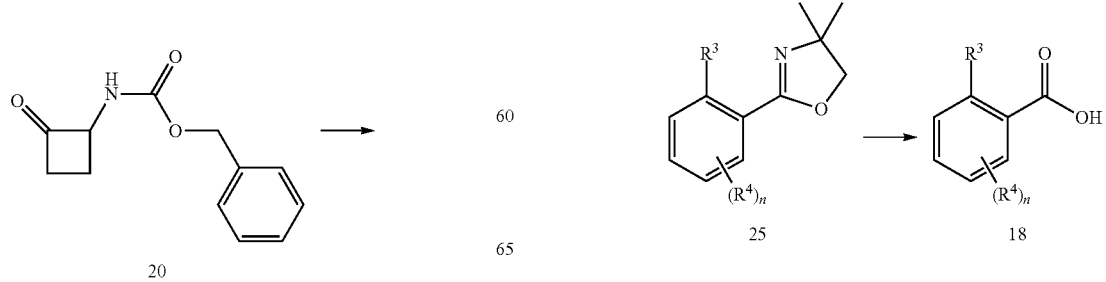

Some acids are prepared according to scheme 12 following methodology described by A. I. Meyers et al. *JOC,* 1978, 43, 1372. Ortho methoxy acid derivative 23 is first converted to the oxazolidinone 24 which is treated with a Grignard reagent $R^3MgX$ to provide intermediate 25 which is then hydrolyzed to acids 18.

Scheme 13

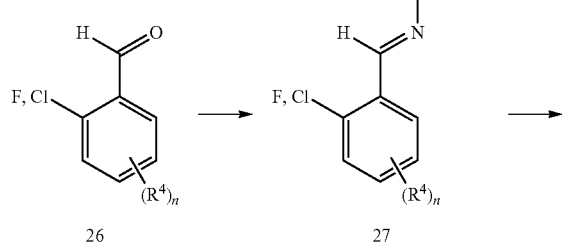

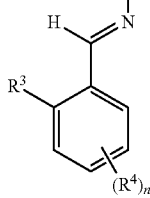

28

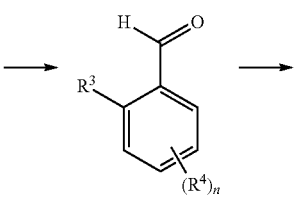

18

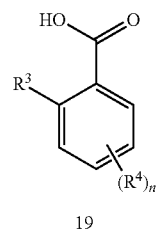

19

Ortho-Fluoro or ortho-chloro benzaldehyde 26 was reacted with butylamine to give imine 27. Addition of a Grignard reagent R'MgBr gave 28. Hydrolysis lead to aldehyde 18 which was oxidized to acid 19.

Scheme 14

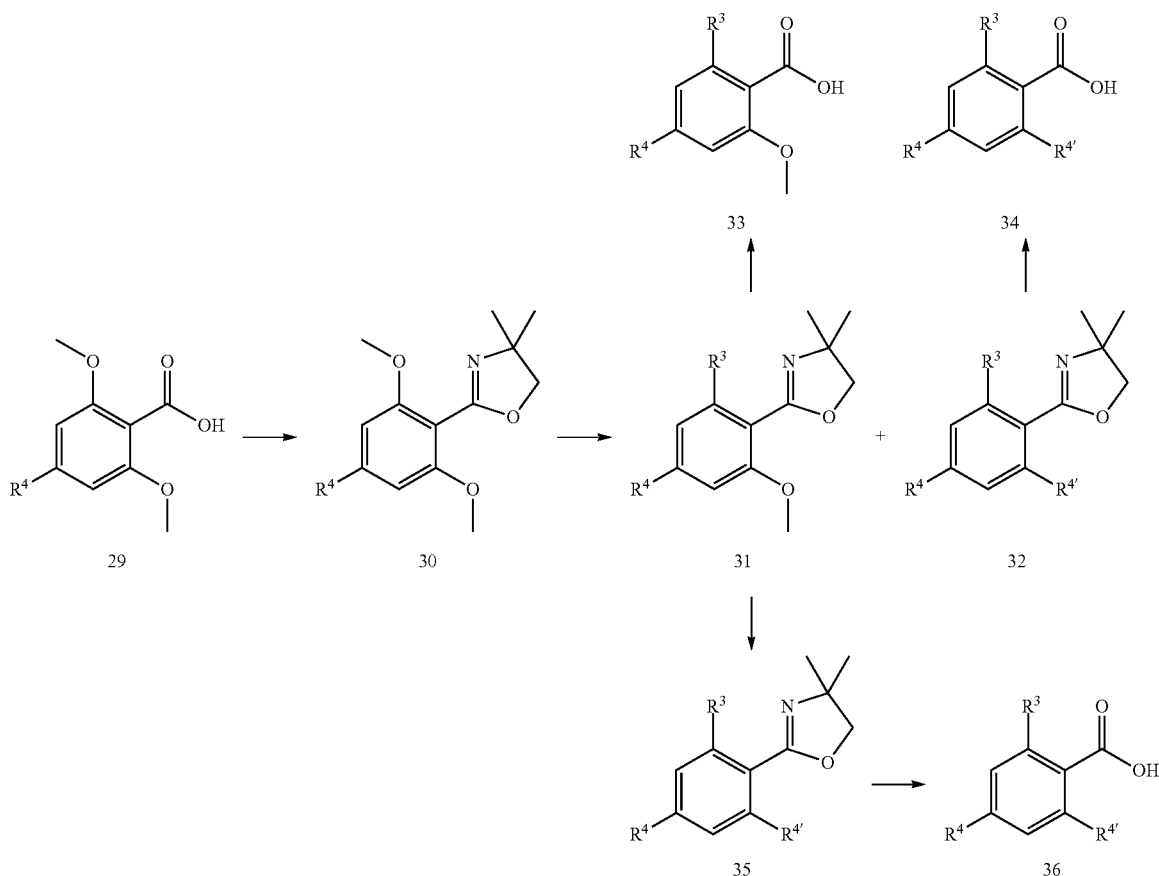

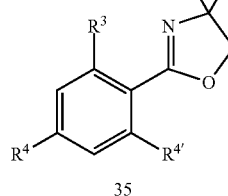

35

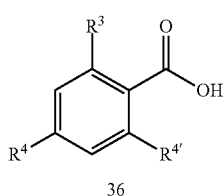

36

The substituents are as described above and R⁴' has the meaning as R⁴ with the exception of methoxy. Some ortho-ortho' substituted acids are prepared according to scheme 14 following methodology as described by A. I. Meyers et al. *JOC*, 1978, 43, 1372. Ortho-ortho' methoxy acid derivative 29 is first converted to the oxazolidinone 30 which is treated with a Grignard reagent R³MgX to provide intermediate 31 (resulting from a mono addition of R³MgX) and intermediate 32 (resulting from a addition of R⁴'MgX) which are then hydrolyzed to respectively acids 33 and 34. Intermediate 31 can also be reacted with a different Grignard reagent R⁴'MgX to provide intermediate 35 which is then hydrolyzed to acid 36.

Racemic mixtures of chiral compound I can be separated using chiral HPLC.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

Experimental Part

Preparation of Intermediates

Intermediate A: 2-Methoxy-6-methylsulfanyl-4-trifluoromethyl-benzoic acid

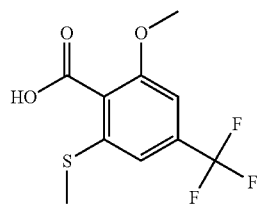

N,N,N'N'-Tetramethylethylendiamine (21 g, 177 mmol) was added drop-wise at −70° C. to a solution of sec-butyl-lithium (110 mL, 1.4 M in cyclohexane, 154 mmol) in 180 mL tetrahydrofuran. 2-Methoxy-4-trifluoromethyl-benzoic acid (13 g, 59 mmol) in 60 mL tetrahydrofuran was added drop-wise at −70° C. over 2 hours. After complete addition stirring was continued at −70° C. for another 2 hours. Dimethyl disulfide (20 g, 207 mmol) was added at −70° C. within 10 min. Stirring was continued at −70° C. for another hour and the reaction was allowed to warm up. The reaction mixture was quenched with 150 mL water and extracted with 200 mL ethyl acetate. The aqueous phase was adjusted to pH1 by addition of 25% HCl and extracted twice with dichloromethane. The combined organic phases were dried on sodium sulfate, filtered and evaporated. The crude product was crystallized with heptane and yielded the title compound as a white solid (1.75 g, 11%), MS: m/e=265.1 [(M−H)⁻].

Intermediate B: 2-Methoxy-6-methylsulfanyl-N-(2-oxo-cyclohexyl)-4-trifluoromethyl-benzamide

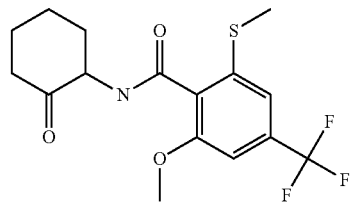

2-Methoxy-6-methylsulfanyl-4-trifluoromethyl-benzoic acid (intermediate A, 400 mg, 1.5 mmol) was dissolved in 10 mL dimethylformamide. N,N-Diisopropyl ethyl amine (505 mg, 3.9 mmol) and O-(7-azabenzotriazol-1-yl)-N,N,N',N'-tetramethyluronium hexafluorophosphate (571 mg, 1.5 mmol) were added. After 5 minutes of stirring at room temperature 2-amino-cyclohexanone (CAS 6946-05-0) (247 mg, 1.6 mmol) was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (heptane/ethyl acetate 1:0→0:1) yielded 2-methoxy-6-methylsulfanyl-N-(2-oxo-cyclohexyl)-4-trifluoromethyl-benzamide as a white foam (370 mg, 68%), MS: m/e=362.2 [(M+H)⁺].

Intermediate C: 2-Methylsulfanyl-4-trifluoromethyl-benzoic acid

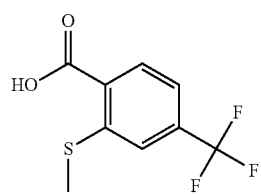

The title compound, white solid, MS: m/e=235.0 [(M−H)⁻], was prepared in accordance with the general method of intermediate A from 4-(trifluoromethyl)benzoic acid and dimethyl disulfide.

Intermediate D: 2-Methylsulfanyl-N-(2-oxo-cyclohexyl)-4-trifluoromethyl-benzamide

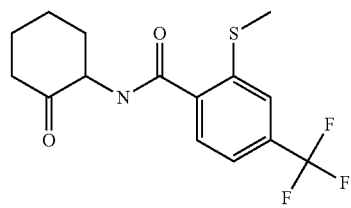

The title compound, off-white solid, MS: m/e=332.1 [(M+H)⁺], was prepared in accordance with the general method of intermediate B from 2-amino-cyclohexanone and 2-methylsulfanyl-4-trifluoromethyl-benzoic acid (intermediate C).

Intermediate E:
cis-(2-Pyrrolidin-1-yl-cyclohexyl)-carbamic acid tert-butyl ester

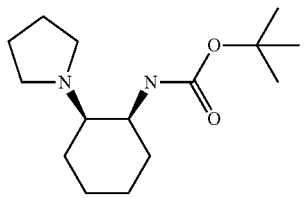

1-N-Boc-1,2-cis-cyclohexyldiamine 5 (CAS 184954-75-4) (1.65 g, 7.7 mmol) was dissolved in 100 mL acetonitrile. Potassium carbonate (5.3 g, 39 mmol) and 1,4-dibromobutane (2.8 g, 13 mmol) were added and the reaction mixture was refluxed overnight. The solvent was evaporated off. The residue was taken up in water and ethyl acetate and was extracted three times with ethyl acetate. The combined organic phases were dried on sodium sulfate, filtered and evaporated. Purification of the residue by flash chromatography on silica gel (dichloromethane/methanol/ammonia 100:0:0→140:10:1) yielded cis-(2-pyrrolidin-1-yl-cyclohexyl)-carbamic acid tert-butyl ester as a yellow liquid (1.82 g, 88%), MS: m/e=269.4 [(M+H)⁺].

Intermediate F:
cis-2-Pyrrolidin-1-yl-cyclohexylamine dihydrochloride

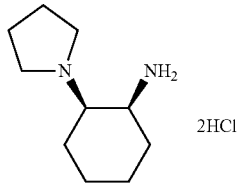

cis-(2-Pyrrolidin-1-yl-cyclohexyl)-carbamic acid tert-butyl ester (1.8 g, 6.7 mmol) was dissolved in dioxane. 4H HCl in dioxane (17 mL, 67 mmol) were added and the reaction mixture was stirred at room temperature overnight. The solvent was evaporated off. The residue was crystallized with ethanol and yielded cis-2-pyrrolidin-1-yl-cyclohexylamine dihydrochloride as a white solid (1.37 g, 85%), MS: m/e=169.2 [(M+H)⁺].

Intermediate G: cis-N-(2-Amino-cyclohexyl)-2-methylsulfanyl-4-trifluoromethyl-benzamide

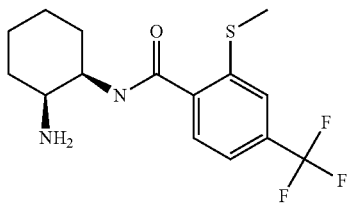

2-Methylsulfanyl-4-trifluoromethyl-benzoic acid (intermediate C, 590 mg, 2.5 mmol) was dissolved in 10 mL dimethylformamide. N,N-Diisopropyl ethyl amine (646 mg, 5 mmol) and O-(7-azabenzotriazol-1-yl)-N,N,N',N'-tetramethyluronium hexafluorophosphate (1.05 g, 2.7 mmol) were added. After 5 minutes of stirring at room temperature cis-1,2-diaminocyclohexane (570 mg, 5 mmol) was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (dichloromethane/methanol/ammonia 100:0:0→140:10:1) yielded cis-N-(2-amino-cyclohexyl)-2-methylsulfanyl-4-trifluoromethyl-benzamide as a light yellow solid (282 mg, 34%), MS: m/e=3331.1 [(M+H)⁺].

Intermediate H: cis-N-(2-Amino-cyclohexyl)-2-methoxy-4,6-bis-trifluoromethyl-benzamide

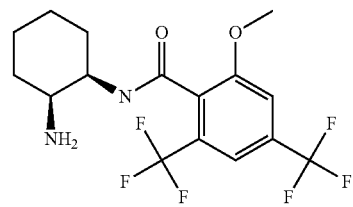

The title compound, yellow foam, MS: m/e=385.1 [(M+H)⁺], was prepared in accordance with the general method of intermediate G from cis-1,2-diaminocyclohexane and 2,4-bis(trifluoromethyl)-6-methoxybenzoic acid.

Intermediate I: cis-N-(2-Amino-cyclohexyl)-2-methoxy-6-methylsulfanyl-4-trifluoromethyl-benzamide

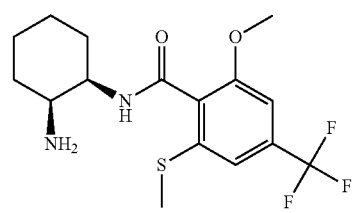

The title compound, yellow foam, MS: m/e=385.1 [(M+H)⁺], was prepared in accordance with the general method of intermediate G from cis-1,2-diaminocyclohexane and 2-methoxy-6-methylsulfanyl-4-trifluoromethyl-benzoic acid (intermediate A).

Intermediate J: cis 2-Methoxy-N-2-(4-oxo-piperidin-1-yl)-cyclohexyl]-4,6-bis-trifluoromethyl-benzamide

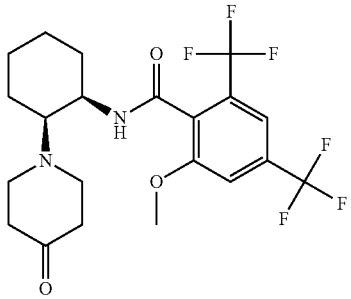

cis-N-(2-Amino-cyclohexyl)-2-methoxy-4,6-bis-trifluoromethyl-benzamide (intermediate H) (400 mg, 1.04 mmol) was dissolved in 27 mL ethanol. Potassium carbonate (86 mg, 0.062 mmol) and 1-ethyl-1-methyl-4-oxo-piperidinium iodide (420 mg, 1.56 mmol) were added. The reaction mixture was refluxed for 2 h. The solvent was evaporated off. The residue was extracted with saturated sodium bicarbonate solution and ethyl acetate. The combined organic phases were dried on sodium sulfate, filtered and evaporated. Purification of the residue by flash chromatography on silica gel (dichloromethane/ethyl acetate 1:0→1:1) yielded cis 2-methoxy-N-2-(4-oxo-piperidin-1-yl)-cyclohexyl]-4,6-bis-trifluoromethyl-benzamide as a light yellow solid (321 mg, 66%), MS: m/e=467.2 [(M+H)+].

Intermediate K:
2-Cyclopropyl-4-trifluoromethyl-benzoic acid

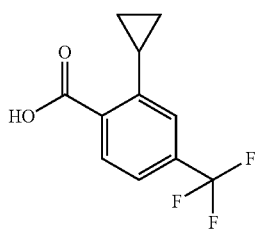

Step 1: 2-Bromo-4-trifluoromethyl-benzoic acid methyl ester

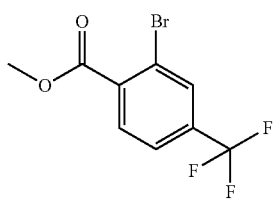

To a solution of 2 g (7.434 mmol) 2-bromo-4-trifluoromethyl-benzoic acid (CAS: 328-89-2) in 20 ml DMF under nitrogen at room temperature, was added 1.13 g (8.177 mmol) potassium carbonate and 557 ul (8.921 mmol) methyl iodide. The mixture was stirred overnight under nitrogen. The mixture was poured into water (300 ml). The aqueous layer was extracted with ethyl acetate (2×80 ml). The combined extracts were dried over sodium sulfate, filtered and concentrated in vacuo. The crude oil was purified on silica gel (eluent: heptane/ethyl acetate 0 to 10%) to provide 1.75 g (83%) of the title compound as an orange oil.

Step 2: 2-Cyclopropyl-4-trifluoromethyl-benzoic acid methyl ester

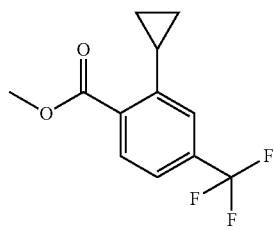

To a solution of 400 mg (1.413 mmol) 2-bromo-4-trifluoromethyl-benzoic acid methyl ester, 146 mg (1.696 mmol) cyclopropyl boronic acid, 1.21 g (4.946 mmol) tri-potassium phosphate monohydrate, 40.9 mg (0.141 mmol) tricyclohexyl phosphine in 6 ml toluene and 0.3 ml water under nitrogen at room temperature, was added 15.9 mg (0.0707 mmol) palladium acetate. The mixture was stirred in a 100° C. oil bath for 4 hours and overnight at room temperature under nitrogen. The mixture was cooled to room temperature. Water was added and the mixture extracted with ethyl acetate. The organic layer was washed once with brine, dried over sodium sulfate, filtered and concentrated in vacuo. The crude compound was purified on silica gel (eluent: heptane/ethyl acetate 0 to 10%) to provide 0.24 g (71%) of the title compound as a yellow oil.

Step 3: 2-Cyclopropyl-4-trifluoromethyl-benzoic acid

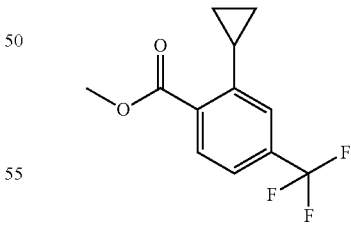

To a suspension of 485 mg (1.986 mmol) 2-cyclopropyl-4-trifluoromethyl-benzoic acid methyl ester in 8 ml ethanol at room temperature, was added 1.99 ml (3.972 mmol) 2N NaOH. The mixture was heated in a 80° C. oil bath for 30 minutes. The solution was cooled to room temperature and the ethanol was evaporated. The residue was diluted with water, acidified with 2N HCl to pH 2 and dichloromethane was added. The aqueous phase was extracted twice with dichloromethane. The combined organic phases were dried over sodium sulfate, filtered and concentrated in vacuo. The crude product was purified on silica gel (eluent: heptane/ethyl acetate 0 to 100%) to provide 0.197 g (27%) of the title compound as a light yellow solid. MS (m/e): 229.0 (M−H).

Intermediate L: cis-N-(2-Amino-cyclohexyl)-2-cyclopropyl-4-trifluoromethyl-benzamide

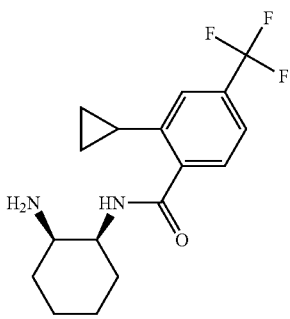

The title compound, yellow solid, MS: m/e=327.2 [(M+H)+], was prepared in accordance with the general method of intermediate G from cis-1,2-diaminocyclohexane and 2-cyclopropyl-4-trifluoromethyl-benzoic acid (intermediate K).

Intermediate M: 2-Methoxy-6-methylsulfanyl-N-(2-oxo-cyclopentyl)-4-trifluoromethyl-benzamide

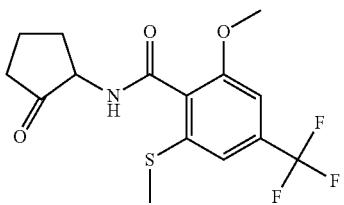

The title compound, yellow solid, MS: m/e=348.2 [(M+H)+], was prepared in accordance with the general method of intermediate B from 2-amino-cyclopentanone dihydrochloride (CAS 5464-16-4) and 2-methylsulfanyl-4-trifluoromethyl-benzoic acid (intermediate C).

Intermediate N: [(1SR,2RS)-2-(2-Methoxy-6-methylsulfanyl-4-trifluoromethyl-benzoylamino)-cyclopentyl]-carbamic acid tert-butyl ester

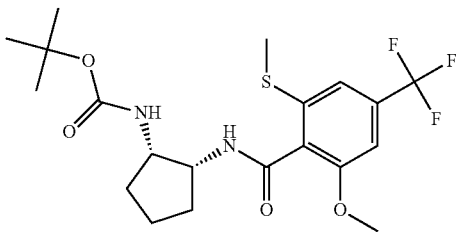

2-Methoxy-6-methylsulfanyl-4-trifluoromethyl-benzoic acid (intermediate A, 1.1 g, 4.1 mmol) was dissolved in 40 mL dimethylformamide. N,N-Diisopropyl ethyl amine (763 mg, 5.9 mmol) and O-(7-azabenzotriazol-1-yl)-N,N,N',N'-tetramethyluronium hexafluorophosphate (1.57 g, 4.1 mmol) were added. After 5 minutes of stirring at room temperature [(1RS,2SR)-2-aminocyclopentyl-carbamic acid 1,1-dimethylethyl ester (CAS 365996-19-6) (993 mg, 5 mmol) was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (heptane ethyl acetate 100:0→1:1) yielded the title compound as a white solid (1.8 g, 100%), MS: m/e=449.2 [(M+H)+].

Intermediate O: N-((1RS,2SR)-2-Amino-cyclopentyl)-2-methoxy-6-methylsulfanyl-4-trifluoromethyl-benzamide

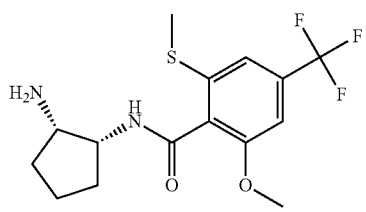

[(1SR,2RS)-2-(2-Methoxy-6-methylsulfanyl-4-trifluoromethyl-benzoylamino)-cyclopentyl]-carbamic acid tert-butyl Ester (intermediate N, 0.2 g, 0.45 mmol) was dissolved in 2 mL methanol. Hydrochloric acid (4M in dioxane, 0.56 mL, 2.2 mmol) was added and the reaction mixture was stirred at room temperature for 4 h. The mixture was poured into 2N sodium carbonate solution and was extracted three times with ethyl acetate. The combined organic phases were dried on sodium sulfate, filtered and evaporated. The crude product was used without any further purification, white solid (147 mg, 94%), MS: m/e=349.2 [(M+H)+].

Intermediate P:
cis-(2-Pyrrolidin-1-yl-cyclopentyl)-carbamic acid tert-butyl ester

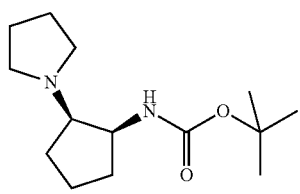

The title compound, brown oil, MS: m/e=255.3 [(M+H)+], was prepared in accordance with the general method of intermediate E from [(1RS,2SR)-2-aminocyclopentyl-carbamic acid 1,1-dimethylethyl ester (CAS 365996-19-6) and 1,4-dibromobutane.

Intermediate Q:
cis-2-Pyrrolidin-1-yl-cyclopentylamine

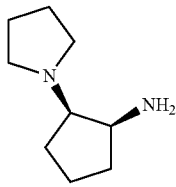

The title compound, white solid, MS: m/e=155.2 [(M+H)+], was prepared in accordance with the general method of intermediate O from cis-(2-Pyrrolidin-1-yl-cyclopentyl)-carbamic acid tert-butyl ester (intermediate P).

Intermediate R: cis-[2-(2-Ethyl-4-trifluoromethyl-benzoylamino)-cyclopentyl]-carbamic acid tert-butyl ester

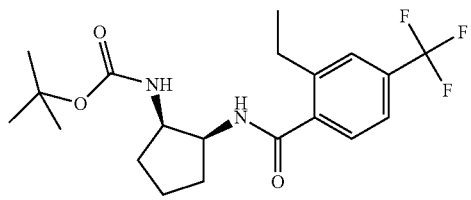

The title compound, light yellow solid, MS: m/e=401.4 [(M+H)+], was prepared in accordance with the general method of intermediate N from [(1RS,2SR)-2-aminocyclopentyl-carbamic acid 1,1-dimethylethyl ester (CAS 365996-19-6) and 2-ethyl-4-(trifluoromethyl)-benzoic acid (CAS 854531-63-8).

Intermediate S: cis-N-(2-Amino-cyclopentyl)-2-ethyl-4-trifluoromethyl-benzamide

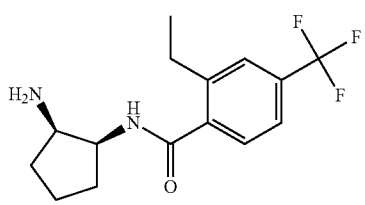

The title compound, white solid, MS: m/e=301.1 [(M+H)+], was prepared in accordance with the general method of intermediate O from cis-[2-(2-ethyl-4-trifluoromethyl-benzoylamino)-cyclopentyl]-carbamic acid tert-butyl ester (intermediate R).

Intermediate T: 2-Cyclopropyl-6-ethyl-benzoic acid

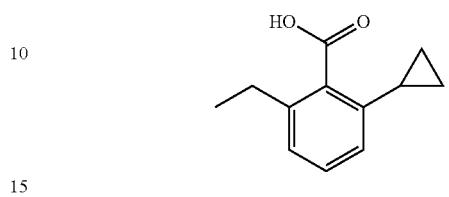

2-Cyclopropyl-6-ethyl-benzaldehyde (CAS 945408-11-7) (500 mg, 2.9 mmol) was dissolved in 3.5 mL tert butanol and 1.7 mL 2-methyl-2-butene. At 0° C. a solution of sodium chlorite (80% purity, 422 mg, 3.8 mmol) and sodium dihydrogenphosphate (452 mg, 3.8 mmol) in 3 mL water was added slowly. The reaction mixture was stirred at room temperature over night. The solvents were evaporated off. The residue was taken up in 1N sodium hydroxide solution and was extracted with tert butyl methylether. The aqueous phase was adjusted at pH 1 with 25% HCl and extracted twice with tert butyl methylether. The combined organic phases were dried on sodium sulfate, filtered and evaporated. The crude product was used without any further purification, white solid (412 mg, 75%), MS: m/e=189.3 [(M−H)−].

Intermediate U:
2-Ethyl-3-methyl-4-trifluoromethyl-benzoic acid

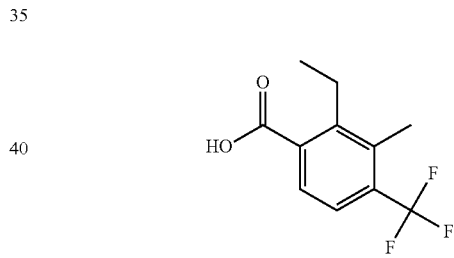

Step 1: 2-(2-Ethyl-3-methyl-4-trifluoromethyl-phenyl)-4,4-dimethyl-4,5-dihydro-oxazole

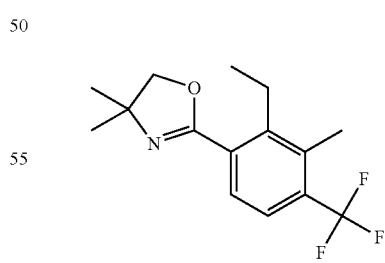

To a cooled solution of 355 mg (1.17 mmol) 2-(2-methoxy-3-methyl-4-trifluoromethyl-phenyl)-4,4-dimethyl-4,5-dihydro-oxazole in 4 ml THF were added at <10° C. drop-wise over 20 min 2.35 ml (4.7 mmol) 2-Methylmagnesium chloride solution in THF. The resulting brown solution was stirred at ambient temperature for 1 h, then quenched with saturated aqueous NH4Cl solution (cooling with ice bath) and extracted three times with tert-butyl methyl ether. The combined organic phases were washed three times with brine, dried over Na$_2$SO$_4$, filtered and evaporated. 2-(2-Ethyl-3-methyl-4-trifluoromethyl-phenyl)-4,4-dimethyl-4,5-dihydro-oxazole was obtained as yellow oil: MS (ISP): 286.1 ((M+H)$^+$).

Step 2: 2-(2-Ethyl-3-methyl-4-trifluoromethyl-phenyl)-3,4,4-trimethyl-4,5-dihydro-oxazol-3-ium iodide

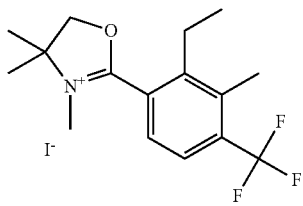

Prepared from 2-(2-ethyl-3-methyl-4-trifluoromethyl-phenyl)-4,4-dimethyl-4,5-dihydro-oxazole and methyl iodide in analogy to intermediate V step 3. 2-(2-Ethyl-3-methyl-4-trifluoromethyl-phenyl)-3,4,4-trimethyl-4,5-dihydro-oxazol-3-ium iodide was obtained as colourless solid: MS (ISP): 300.1 (M$^+$).

Step 3: 2-Ethyl-3-methyl-4-trifluoromethyl-benzoic acid

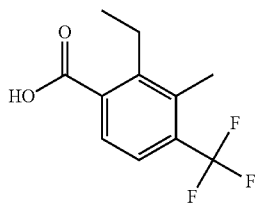

Prepared from 2-(2-ethyl-3-methyl-4-trifluoromethyl-phenyl)-3,4,4-trimethyl-4,5-dihydro-oxazol-3-ium iodide in analogy to intermediate V step 4. Ethyl-3-methyl-4-trifluoromethyl-benzoic acid was obtained as yellow solid: MS (ISN): 231.06 ((M–H)$^-$).

Intermediate V:
2-Methoxy-3-methyl-4-trifluoromethyl-benzoic acid

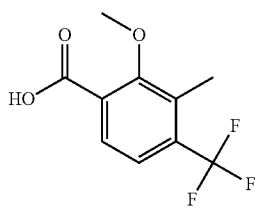

Step 1: 2-(2-Methoxy-4-trifluoromethyl-phenyl)-4,4-dimethyl-4,5-dihydro-oxazole

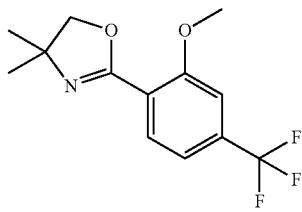

To a solution of 24.98 g (113 mmol) 4-(trifluoromethyl)-2-methoxy-benzoic acid in 220 ml toluene were added 82 ml (1.13 mol) thionyl chloride and 5 drops dimethylformamide. The mixture was heated to 80° C. for 3 h. Then the reaction mixture was concentrated at 50° C./10 mbar. The remaining acid chloride, 27.9 g of a light yellow liquid, was dissolved in 160 ml dichloromethane, cooled to 0° C. and a solution of 20.34 g (228 mmol) 2-amino-2-methyl-propan-1-ol in 60 ml dichloromethane added. The mixture was allowed to stir at ambient temperature for 16 h. The off-white suspension was diluted with water, the aqueous phase evaporated and the organic phase extracted 3 times with ethyl acetate. The combined organic layers were dried over Na$_2$SO$_4$, filtered and concentrated. The crude product, 33.2 g N-(2-hydroxy-1,1-dimethyl-ethyl)-2-methoxy-4-trifluoro-methyl-benzamide, a light yellow oil was dissolved in 220 ml dichloromethane and cooled to 0° C. Then 24.7 ml (340 mmol) thionyl chloride was added drop-wise and the resulting light yellow solution stirred at ambient temperature for 16 h. Then the pH was adjusted to 10 by addition of saturated aqueous Na$_2$CO$_3$ solution. The aqueous layer was separated and extracted 3 times with tert-butyl methyl ether. The combined organic phases were washed twice with brine, dried over Na$_2$SO$_4$, filtered and concentrated. 2-(2-Methoxy-4-trifluoromethyl-phenyl)-4,4-dimethyl-4,5-dihydro-oxazole was obtained as light yellow oil which was used without further purification: MS (ISP): 274.1 ((M+H)$^+$).

Step 2: 2-(2-Methoxy-3-methyl-4-trifluoromethyl-phenyl)-4,4-dimethyl-4,5-dihydro-oxazole

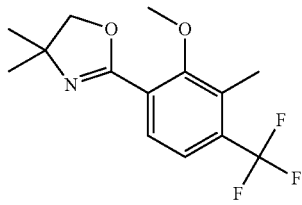

To a solution of 5.465 g (20 mmol) 2-(2-methoxy-4-trifluoromethyl-phenyl)-4,4-dimethyl-4,5-dihydro-oxazole in 60 ml dry THF were added at <–60° C. 11.0 ml (22 mmol) lithium diisopropylamide solution 2M in THF/heptanes/ethylbenzene and the mixture stirred for 1.5 h at <–60° C. To the resulting dark brown solution were added 2.5 ml (40 mmol) iodomethane drop wise over 10 min (exothermal, Ti <–48° C.). The resulting light brown solution was stirred at <–50° C. for 2.5 h then quenched with sat. aq. NH$_4$Cl solution and extracted three times with tert-butyl methyl ether. The combined organic phases were washed 3× with brine, dried over Na₂SO₄, filtered and evaporated: 7.002 g yellow solid: which was purified by flash-chromatography on silica gel with heptane and 5 to 10% AcOEt over 25 min and heptane/AcOEt 90:10 for 20 min. 2-(2-Methoxy-3-methyl-4-trifluoromethyl-phenyl)-4,4-dimethyl-4,5-dihydro-oxazole was obtained as light yellow oil: MS (ISP): 288.12 ((M+H)⁺).

Step 3: 2-(2-Methoxy-3-methyl-4-trifluoromethyl-phenyl)-3,4,4-trimethyl-4,5-dihydro-oxazol-3-ium iodide

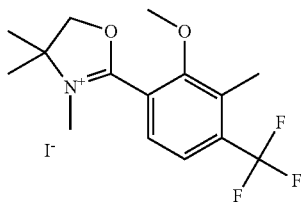

To a solution of 447 mg (1.6 mmol) 2-(2-methoxy-3-methyl-4-trifluoromethyl-phenyl)-4,4-dimethyl-4,5-dihydro-oxazole in 4 ml nitromethane was added 0.78 ml (12 mmol) methyl iodide and the mixture heated in a sealed tube to 60° C. for 18 h. The brown solution was diluted with tert-butyl methyl ether, the suspension filtered and the precipitate washed with tert-butyl methyl ether and dried. 2-(2-Methoxy-3-methyl-4-trifluoromethyl-phenyl)-3,4,4-trimethyl-4,5-dihydro-oxazol-3-ium iodide was obtained as off-white powder: MS (ISP): 302.1 (M⁺).

Step 4:
2-Methoxy-3-methyl-4-trifluoromethyl-benzoic acid

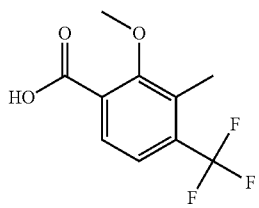

A solution of 515 mg (1.2 mmol) 2-(2-methoxy-3-methyl-4-trifluoromethyl-phenyl)-3,4,4-trimethyl-4,5-dihydro-oxazol-3-ium iodide in 5 ml methanol and 5 ml 20% NaOH was heated to 70° C. for 17 h. The yellow solution was cooled to rt, methanol was distilled off, the residue acidified with conc. HCl to pH 1 and extracted three times with tert-butyl methyl ether. The combined organic phases were washed twice with brine, dried over Na₂SO₄, filtered and evaporated: 2-Methoxy-3-methyl-4-trifluoromethyl-benzoic acid was obtained as yellow solid: MS (ISN): 233.04 ((M–H)⁻).

Intermediate W:
2-Bromo-6-methoxy-4-trifluoromethyl-benzoic acid

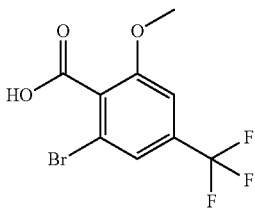

To −75° C. cooled THF (70 ml) was added dropwise 36 ml (50.0 mmol) of a 1.4 M sec-BuLi solution in cyclohexane within 5 minutes keeping the temperature below −70° C. 7.5 ml (50.0 mmol) TMEDA were added dropwise at temperature below −70° C. within 5 minutes. A solution of 5.0 g (22.71 mmol) 2-methoxy-4-(trifluoromethyl)benzoic acid (commercial) in THF (25 ml) was added dropwise at over a period of 20 minutes. The dark green solution was stirred at −75° C. for 2 hours. A solution of 29.6 g (90.84 mmol) 1,2-dibromotetrachloroethane in THF (30 ml) was added dropwise. The off-white suspension was stirred at −75° C. for 1 hour and then allowed to warm to room temperature. The yellow solution was quenched by dropwise addition of 60 ml water under ice bath cooling. The mixture was diluted with ethyl acetate (70 ml) and water (30 ml). The aqueous layer was extracted with ethyl acetate (50 ml), acidified with HCl 25% and extracted with ethyl acetate (3×50 ml). The extracts were combined, dried over sodium sulfate, filtered and concentrated in vacuo. The crude product was stirred in heptane, filtered and dried. The solid was recrystallized from heptane (7 ml) and ethyl acetate (2 ml) to provide 815 mg (12%) of the title compound as a white solid. MS (m/e): 298.9 (M–H).

Intermediate X:
2,6-Dichloro-4-trifluoromethyl-benzaldehyde

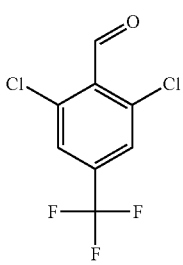

A solution of 4-bromo-3,5-dichlorobenzotrifluoride (1 g, 3.4 mmol) in 1.2 mL tetrahydrofurane was slowly added to isopropylmagnesium bromide (15% in THF, 3.3 g, 3.4 mmol) at max. −10° C. After complete addition the reaction mixture was stirred for 30 min at −10° C. Dimethylformamide (0.275 g, 3.7 mmol) was added and the mixture was slowly warmed up. The mixture was quenched with saturated ammonium chloride solution and extracted three times with ethyl acetate. The combined organic phases were dried on sodium sulfate, filtered and evaporated. The crude product was used without any further purification, brown oil (741 mg, 89%).

Intermediate Y: 2,6-Dichloro-4-trifluoromethyl-benzoic acid

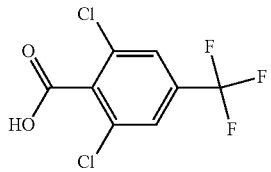

The title compound, light yellow solid, MS: m/e=257.3 [(M−H)⁻], was prepared in accordance with the general method of intermediate W from 2,6-dichloro-4-trifluoromethyl-benzaldehyde.

Intermediate Z: 2-Methylsulfanyl-6-trifluoromethyl-benzoic acid

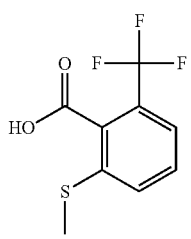

The title compound, white solid, MS: m/e=235.0 [(M−H)⁻], was prepared in accordance with the general method of intermediate A from 2-(trifluoromethyl)benzoic acid and dimethyl disulfide.

Intermediate AA: (2-Pyrrolidin-1-yl-cyclobutyl)-carbamic acid benzyl ester (mixture of diastereomers)

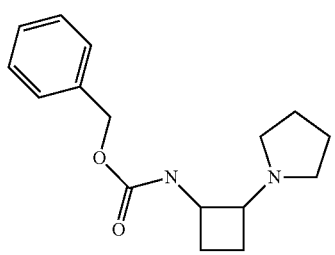

The title compound, colorless oil, MS: m/e=275.1 [(M+H)⁺], were prepared in accordance with the general method of example 1 and 2 from (2-oxo-cyclobutyl)-carbamic acid benzyl ester (CAS 406951-43-7) and pyrrolidine. The 2 diastereomers were not separated.

Intermediate AB: 2-Pyrrolidin-1-yl-cyclobutylamine hydrochloride (mixture of diastereomers)

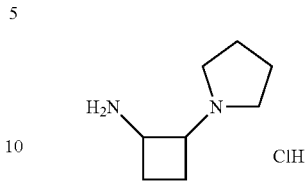

(2-Pyrrolidin-1-yl-cyclobutyl)-carbamic acid benzyl ester (intermediate AA, 475 mg, 1.7 mmol) was dissolved in 25 mL methanol and 4N HCl in dioxane (870 mL, 3.4 mmol) and palladium on charcoal (10%, 184 mg, 0.17 mmol) were added. The reaction mixture was hydrogenated at room temperature with a H₂-balloon over night. The palladium on charcoal was filtered off and the solvent was evaporated. The crude product was used without any further purification, light yellow semisolid (525 mg, 99%). The 2 diastereomers were not separated.

Intermediate AC: N-((1SR,2RS)-2-Amino-cyclopropyl)-2-methoxy-6-methylsulfanyl-4-trifluoromethyl-benzamide

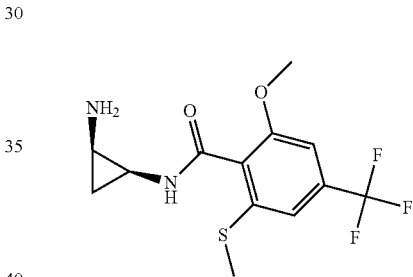

The title compound, light yellow foam, MS: m/e=319.1 [(M−H)⁻], was prepared in accordance with the general method of intermediate G from cis-1,2-diaminocyclopropane (CAS 45347-36-2) and 2,4-bis(trifluoromethyl)-6-methoxy-benzoic acid.

Intermediate AD: ((1RS,2SR)-2-Cyclopentylamino-cyclopentyl)-carbamic acid tert-butyl ester

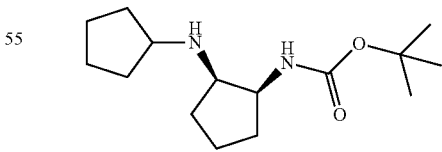

To a solution of [(1RS,2SR)-2-aminocyclopentyl-carbamic acid 1,1-dimethylethyl ester (CAS 365996-19-6) (500 mg, 2.497 mmol) in 10 ml methanol was added acetic acid (0.714 ml, 12.49 mmol) and cyclopentanone (0.665 ml, 7.491 mmol). The mixture was heated in a 50° C. oil bath for 1.5 hour. The solution was cooled to room temperature and sodium cyanoborohydride (370 mg, 5.0 mmol) was added portionwise. The mixture was heated in a 50° C. oil bath for 2.5 hours. The solution was cooled in an ice bath and quenched by dropwise addition of 6 ml 2N NaOH. The methanol was removed in vacuo. The aqueous layer was diluted with water and extracted 3 times with ethyl acetate. The combined extracts were dried over $Na_2SO_4$, filtered and concentrated in vacuo. The crude oil was purified on silica gel (eluent: heptane/ethyl acetate 0 to 100%) to provide 0.39 g (58%) of the title compound as a light brown solid. MS (m/e): 269.3 (M+H).

Intermediate AE:
(1RS,2SR)-N-Cyclopentyl-cyclopentane-1,2-diamine

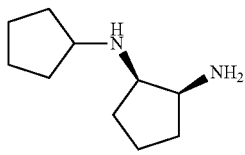

The title compound, grey solid, MS: m/e=169.3 [(M+H)$^+$], was prepared in accordance with the general method of intermediate O from ((1RS,2SR)-2-cyclopentylamino-cyclopentyl)-carbamic acid tert-butyl (intermediate AD).

Intermediate AF:
2-Isopropoxy-4-trifluoromethyl-benzoic acid

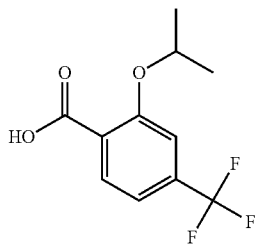

To a solution of p-(trifluoromethyl)salicylic acid (CAS 345-28-8) (500 mg, 2.271 mmol), 2-propanol (0.209 ml, 2.725 mmol) and triphenylphosphine (706.2 mg, 2.612 mmol) in 6.5 ml tetrahydrofurane under nitrogen at 0° C., was added dropwise a solution of di-tert-butyl azodicarboxylate (575.2 mg, 2.498 mmol) in 1 ml tetrahydrofurane. The reaction mixture was allowed to warm to room temperature and stirred for 1.5 hours. 8 ml 2N NaOH (15.9 mmol) was added and the reaction mixture was heated in an 80° C. oil bath for 5 hours. The reaction mixture was allowed to cool to room temperature and extracted twice with 5 ml ether. The aqueous layer was acidified under ice bath cooling with a 5N HCl solution to pH 1. The resulting precipitate was filtered and dried in vacuo to provide 444 mg (79%) of the title compound as a white solid. MS (m/e): 247.0 (M+H+).

Intermediate AG: 2-(2-Methoxy-4-trifluoromethyl-phenyl)-4,4-dimethyl-4,5-dihydro-oxazole

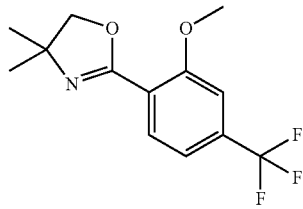

To a solution of 2-amino-2-methyl-1-propanol (9.94 ml, 100.6 mmol) in 100 ml dichloromethane under nitrogen at 0° C., was added dropwise a solution of 2-methoxy-4-trifluoromethyl-benzoyl chloride (12 g, 50.29 mmol) in 30 ml dichloromethane. The temperature rose to 7° C. The mixture was stirred at room temperature for 45 minutes. The mixture was poured onto 200 ml water. The organic layer was separated and the aqueous layer was reextracted twice with dichloromethane. The combined organic layers were washed with brine, dried over $Na_2SO_4$, filtered and concentrated in vacuo to provide 15.34 g of an orange oil. A solution of this intermediate in 150 ml dichloromethane was cooled to 10° C. Thionylchloride (11.2 ml, 154.5 mmol) was added dropwise. The temperature rose to 15° C. The mixture was stirred at room temperature for 45 minutes. The solution was added dropwise to 350 ml of a cooled 2M $Na_2CO_3$ solution. The emulsion was diluted with 200 ml water and filtered, to remove the white solid. The organic layer was separated and the aqueous layer was reextracted twice with dichloromethane. The combined extracts were dried over $Na_2SO_4$, filtered and concentrated in vacuo to provide 13.16 g (93.5%) of the title compound as a light yellow oil. MS (m/e): 274.2 (M+H$^+$).

Intermediate AH:
2-Isopropyl-4-trifluoromethyl-benzoic acid

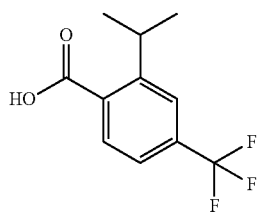

Step 1. Preparation of 2-(2-isopropyl-4-trifluoromethyl-phenyl)-4,4-dimethyl-4,5-dihydro oxazole

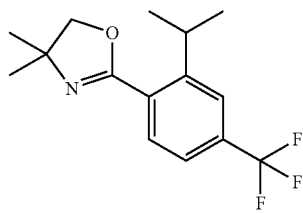

To a cooled (0° C.) solution of 2-(2-methoxy-4-trifluoromethyl-phenyl)-4,4-dimethyl-4,5-dihydro-oxazole (intermediate AG) (1.0 g, 3.66 mmol) in 6.0 ml THF, was added dropwise a 1M ispropylmagnesium bromide solution in THF (11.0 ml, 10.98 mmol) maintaining the temperature below 5° C. The mixture was allowed to warm to room temperature and stirred for 1 hour. The mixture was cooled in an ice bath and quenched dropwise with 25 ml saturated $NH_4Cl$ solution. Ethyl acetate was added. The organic layer was separated and the aqueous layer was reextracted once with ethyl acetate. The combined extracts were dried over $Na_2SO_4$, filtered and concentrated in vacuo. The crude oil was purified on silica gel (eluent: heptane/ethyl acetate 0 to 20%) to provide 0.95 g (91%) of the title compound as a light yellow oil. MS (m/e): 286.1 (M+H).

Step 2. Preparation of 2-(2-isopropyl-4-trifluoromethyl-phenyl)-3,4,4-trimethyl-4,5-dihydro-oxazol-3-ium iodide

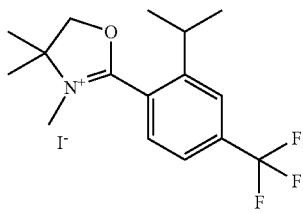

To a solution of 2-(2-isopropyl-4-trifluoromethyl-phenyl)-4,4-dimethyl-4,5-dihydro oxazole (step 1) (950 mg, 3.33 mmol) in 8.0 ml acetone was added) iodomethane (2.1 ml, 33.3 mmol). The mixture was heated in a 55° C. oil bath for 48 hours. The solvent was removed in vacuo. The solid was stirred in ether, filtered and dried to provide 1.27 g (89%) of the title compound as light yellow solid. MS (m/e): 300.4 (M).

Step 3. Preparation of 2-Isopropyl-4-trifluoromethyl-benzoic acid

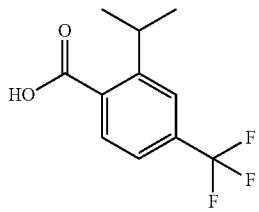

To a solution of 2-(2-isopropyl-4-trifluoromethyl-phenyl)-3,4,4-trimethyl-4,5-dihydro-oxazol-3-ium iodide (step 2) (1.26 g, 2.949 mmol) in 12 ml methanol were added 5N NaOH solution (11.8 ml, 58.98 mmol). The mixture was stirred in a 75° C. oil bath for 3 hours. The solution was cooled in an ice bath and acidified to pH 1 with a 5N HCl solution. The methanol was removed in vacuo. The suspension was stirred in an ice bath. The solid was filtered, washed with water and dried in vacuo to provide 618 mg (90%) of the title compound as a white solid. MS (m/e): 231.1 (M−H).

Intermediate AI:
5-trifluoromethyl-biphenyl-2-carboxylic acid

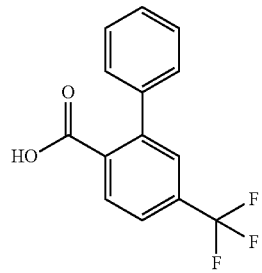

A mixture of 2-iodo-4-trifluoromethyl-benzoic acid (CAS: 54507-44-7) (300 mg, 0.949 mmol) phenylboronic acid (239 mg, 1.898 mmol), sodium carbonate (302 mg, 2.847 mmol) and palladium (II) acetate (10.7 mg, 0.0475 mmol) in 4.5 ml water was stirred at room temperature for 48 hours. The mixture was filtered and the filtrate was acidified with HCl 37%. The mixture was stirred at room temperature for 30 minutes. The solid was filtered, washed with water and dried in vacuo to provide 225 mg (89%) of the title compound as a brown solid. MS (m/e): 264.9 (M+H$^+$).

Intermediate AJ:
2,6-Dimethoxy-4-trifluoromethyl-benzoic acid

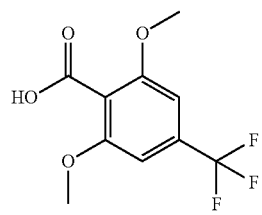

To a solution of sodium hydroxide (5.66 g, 141.4 mmol) in 33 ml water and 33 ml ethanol at room temperature under nitrogen, was added 2,6-dimethoxy-4-trifluoromethyl-benzonitrile (CAS: 51271-36-4) (3.27 g, 14.14 mmol). The reaction mixture was heated in a 90° C. oil bath for 37 hours. The reaction mixture was cooled to room temperature and 130 ml water was added. The product was collected by filtration and dried to provide 3.05 g of an off-white solid. To a solution of nitrosylsulfuric acid (15.6 g, 110.2 mmol) in 9.5 ml water at 0° C. under nitrogen, was added dropwise a suspension of the previously obtained material in 19 ml dichloromethane. The reaction mixture was stirred at 0° C. for 4.5 h. The reaction mixture was poured over ice and extracted with dichloromethane. The combined organic layers were dried over $Na_2SO_4$, filtered and dried to provide 1.51 g of product. The aqueous phase was filtered and the white solid was dried to provide 1.36 g of product. Both batches were mixed to provide 2.87 g (93.7%) of the title compound as a white solid. MS (m/e): 249.1 (M−H).

Intermediate AK: Butyl-[1-(2-fluoro-4,6-bis-trifluoromethyl-phenyl)-methylidene]-amine

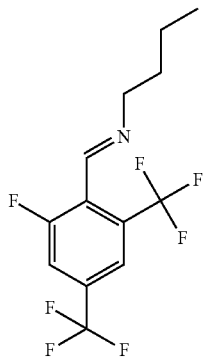

2-Fluoro-4,6-bis(trifluoromethyl)benzaldehyde (10 g, 38 mmol) was dissolved in 30 mL toluene. p-Toluenesulfonic acid (140 mg, 0.74 mmol) and N-butylamine (2.94 g, 40 mmol) were added. The reaction mixture was refluxed overnight. The mixture was extracted with 2N sodium carbonate solution and ethyl acetate. The combined organic phases were dried on sodium sulfate, filtered and evaporated. The crude material, orange oil (12 g, >100%) was used without further purification.

Intermediate AL: Butyl-[1-(2-cyclopropyl-4,6-bis-trifluoromethyl-phenyl)-methylidene]-amine

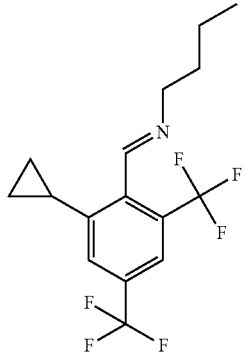

Cyclopropylbromide (3.84 g, 32 mmol) was added to magnesium (771 mg, 32 mmol) in 20 mL diethylether and refluxed for 10 min. Manganese(II) chloride (160 mg, 1.27 mmol) and butyl-[1-(2-fluoro-4,6-bis-trifluoromethyl-phenyl)-methylidene]-amine (intermediate AK, 4 g, 13 mmol) was added. The reaction mixture was refluxed for 2 h. The reaction mixture was quenched with 8 mL water and filtered through dicalite. The organic phase was separated and dried on sodium sulfate, filtered and evaporated. The crude material, brown oil (3.54 g, 82%) was used without further purification.

Intermediate AM: 2-Cyclopropyl-4,6-bis-trifluoromethyl-benzaldehyde

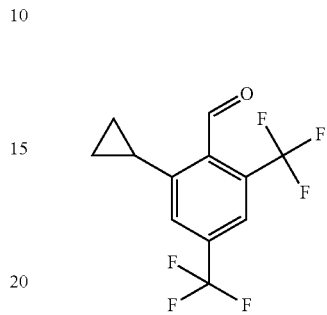

Crude butyl-[1-(2-cyclopropyl-4,6-bis-trifluoromethyl-phenyl)-methylidene]-amine (intermediate AL, 3.54 g, 10.5 mmol) was dissolved in 8 mL water. Hydrochloric acid (25%, 0.49 mL) was added and the mixture was refluxed for 2 h. The mixture was extracted three times with ethyl acetate. The combined organic phases were dried on sodium sulfate, filtered and evaporated. The crude material, brown oil (1.01 g, 34%) was used without further purification.

Intermediate AN: 2-Cyclopropyl-4,6-bis-trifluoromethyl-benzoic acid

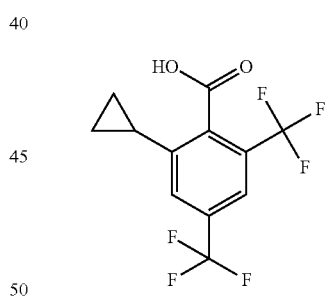

Crude 2-cyclopropyl-4,6-bis-trifluoromethyl-benzaldehyde (intermediate AM, 1.01 g, 3.58 mmol) was dissolved in 8.5 mL tert-butylalcohol and 4.5 mL 2-methyl-2-butene. At 0° C. a solution of sodium chlorite (340 mg, 3.76 mmol) and sodium dihydrogenphosphat (451 mg, 3.76 mmol) in 3 mL water was added. The reaction mixture was stirred at room temperature overnight. The solvents were evaporated off. The residue was taken up in 1N NaOH and extracted twice with tert-butyl methyl ether. The aqueous phase was adjusted to pH 2 by addition of 25% HCl and extracted twice with tert-butyl methyl ether. The combined organic phases were dried on sodium sulfate, filtered and evaporated. The crude material, off-white solid (1.01 g, 54%) was used without further purification.

Intermediate AO:
2-Ethyl-4,6-bis-trifluoromethyl-benzoic acid

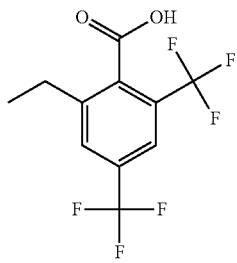

The title compound, white solid, MS: m/e=285.2 [(M−H)⁻], was prepared in accordance with the general method of intermediate A from 2,4-bis(trifluoromethyl)benzoic acid and iodomethane.

Intermediate AP:
2-Cyclobutyl-4-trifluoromethyl-benzoic acid

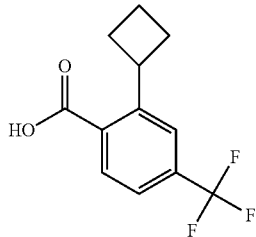

The title compound, white solid, MS: m/e=243.0 [(M−H)⁻], was prepared in accordance with the general method of intermediate K from 2-iodo-4-trifluoromethyl-benzoic acid methyl Ester and cyclobutylzincbromide followed by saponification with sodium hydroxide.

Intermediate AQ:
2,6-Dimethyl-4-trifluoromethyl-benzoic acid

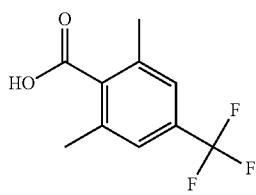

Step 1. Preparation of 2,6-Dimethoxy-4-trifluoromethyl-benzoyl chloride

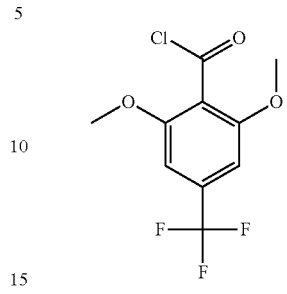

To a suspension of 14.47 g (57.84 mmol) 2,6-dimethoxy-4-trifluoromethyl-benzoic acid (intermediate AJ) in 160 ml toluene containing four drops DMF under nitrogen at room temperature, was added 42 ml (578.4 mmol) thionyl chloride. The mixture was heated in an 85° C. oil bath for 3 hours. The solvent was removed in vacuo to provide 15.37 g (yield: 98.9%) of the title compound as an off-white solid.

Step 2. Preparation of N-(2-Hydroxy-1,1-dimethyl-ethyl)-2,6-dimethoxy-4-trifluoromethyl-benzamide

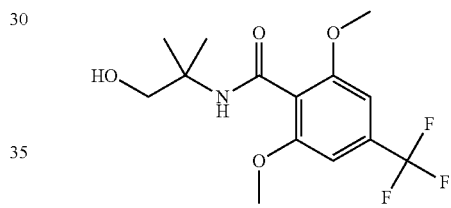

To a solution of 3.7 ml (37.22 mmol) 2-amino-2-methyl-1-propanol in 42 ml dichloromethane under nitrogen at 0° C., was added dropwise a solution of 5 g (18.61 mmol) 2,6-dimethoxy-4-trifluoromethyl-benzoyl chloride in 12 ml dichloromethane. The temperature rose to 7° C. The mixture was stirred at room temperature for 4 hours. The mixture was poured onto 75 ml water. The organic layer was separated and the aqueous layer was extracted twice with dichloromethane. The combined organic layers were washed with brine, dried over sodium sulfate, filtered and concentrated in vacuo to provide 5.66 g (yield: 94.6%) of the title compound as a yellow solid. MS (m/e): 322.2 (M+H⁺).

Step 3. Preparation of 2-(2,6-Dimethoxy-4-trifluoromethyl-phenyl)-4,4-dimethyl-4,5-dihydro-oxazole

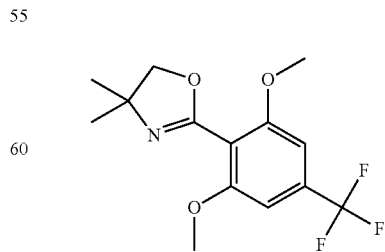

A solution of 5.66 g (17.62 mmol) N-(2-hydroxy-1,1-dimethyl-ethyl)-2,6-dimethoxy-4-trifluoromethyl-benzamide in 60 ml dichloromethane was cooled to 10° C. 3.8 ml (52.85 mmol) thionylchloride was added drop-wise. The temperature rose to 15° C. The mixture was stirred at room temperature for 1 hour. The solution was added drop-wise to 130 ml of a cooled 2M sodium carbonate solution. The emulsion was diluted with water and filtered, to remove the white solid. The organic layer was separated and the aqueous layer was extracted twice with dichloromethane. The combined extracts were dried over sodium sulfate, filtered and concentrated in vacuo. The crude light yellow solid (5.27 g) was purified with flash column chromatography on silica (70 g) eluting with a gradient formed from n-heptane and ethyl acetate (0 to 50%) to provide 4.8 g (yield: 89.8%) of the title compound as a white solid. MS (m/e): 304.2 (M+H$^+$).

Step 4. Preparation of 2-(2,6-Dimethyl-4-trifluoromethyl-phenyl)-4,4-dimethyl-4,5-dihydro-oxazole (compound A)

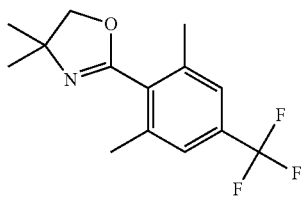

And 2-(2-Methoxy-6-methyl-4-trifluoromethyl-phenyl)-4,4-dimethyl-4,5-dihydro-oxazole (compound B)

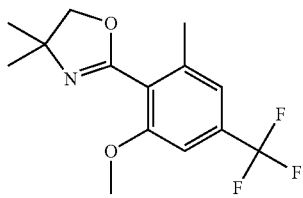

To a 0° C. solution of 1.5 g (4.946 mmol) 2-(2,6-dimethoxy-4-trifluoromethyl-phenyl)-4,4-dimethyl-4,5-dihydro-oxazole in 9 ml tetrahydrofuran over mol-sieve, was added dropwise 9.89 ml (29.68 mmol) of a 3M methylmagnesium bromide solution in diethyl ether maintaining the temperature below 5° C. The mixture was allowed to warm to room temperature and was then heated in a 70° C. oil bath for 24 hours. The mixture was cooled in an ice bath and quenched with 60 ml of a saturated ammonium solution. Ethyl acetate was added. The organic layer was separated and the aqueous layer was extracted once with ethyl acetate. The combined extracts were dried over sodium sulfate, filtered and concentrated in vacuo. The crude orange oil (1.38 g) was purified with flash column chromatography on silica eluting with a gradient formed from n-heptane and ethyl acetate (0 to 35%) to provide 419 mg (yield: 31.2%) of 2-(2,6-dimethyl-4-trifluoromethyl-phenyl)-4,4-dimethyl-4,5-dihydro-oxazole (compound A) as a white solid. MS (m/e): 272.2 (M+H$^+$) and 532 mg (yield: 37.4%) of 2-(2-Methoxy-6-methyl-4-trifluoromethyl-phenyl)-4,4-dimethyl-4,5-dihydro-oxazole (compound B) as a colorless oil. MS (m/e): 288.1 (M+H$^+$)

Step 5. Preparation of 2,6-Dimethyl-4-trifluoromethyl-benzoic acid 2-methyl-2-nitro-propyl ester

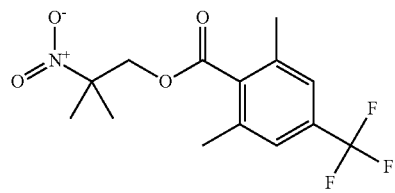

To a solution of 415 mg (1.530 mmol) 2-(2,6-dimethyl-4-trifluoromethyl-phenyl)-4,4-dimethyl-4,5-dihydro-oxazole in 17 ml acetonitrile was added 15.3 ml (0.0061 mmol) of an 0.4 mM aqueous Na$_2$-EDTA solution at room temperature. 1.4 ml (15.30 mmol) 1,1,1-trifluoroacetone was added at once with a pre-cooled syringe. A mixture of 3.86 g (45.90 mmol) sodiumbicarbonate and 9.41 g (15.30 mmol) oxone was added portion-wise over a period of 15 minutes. The mixture was stirred for 30 minutes. The reaction mixture was diluted with 90 ml water. The aqueous layer was extracted 3 times with dichloromethane. The combined extracts were dried over sodium sulfate, filtered and concentrated in vacuo to provide 477 mg (y: 97.7%) of the title compound as a colorless oil.

Step 6. Preparation of 2,6-Dimethyl-4-trifluoromethyl-benzoic acid

To a solution of 475 mg (1.488 mmol) 2,6-dimethyl-4-trifluoromethyl-benzoic acid 2-methyl-2-nitro-propyl ester in 4.7 ml dioxane was added 3 ml (14.88 mmol) of a 5M aqueous NaOH solution. The mixture was heated in a 100° C. oil bath for 24 hours. The dioxane was removed in vacuo. The residue was diluted with water and extracted twice with ethyl acetate. The aqueous layer was acidified with HCl 5N and extracted 3 times with dichloromethane. The combined dichloromethane extracts were dried over sodium sulfate, filtered and concentrated in vacuo to provide 301 mg (y: 92.7%) of the title compound as a light yellow solid. MS (m/e): 217.1 (M−H).

Intermediate AR: 2-Ethyl-6-methoxy-4-trifluoromethyl-benzoic acid

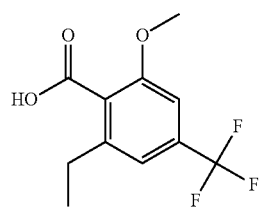

The title compound, light yellow solid, MS: m/e=247.0 (M−H), was prepared according to the procedure described for intermediate AQ from 2-(2,6-dimethoxy-4-trifluoromethyl-phenyl)-4,4-dimethyl-4,5-dihydro-oxazole using ethylmagnesium bromide as a Grignard reagent.

Intermediate AS:
2-Cyclopropyl-6-methoxy-4-trifluoromethyl-benzoic acid

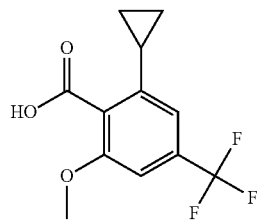

The title compound, off-white solid, MS: m/e=258.9 (M–H), was prepared according to the procedure described for intermediate AQ from 2-(2,6-dimethoxy-4-trifluoromethyl-phenyl)-4,4-dimethyl-4,5-dihydro-oxazole using cyclopropylmagnesium bromide as a Grignard reagent.

Intermediate AT: 2-Difluoromethoxy-6-methoxy-4-trifluoromethyl-benzoic acid

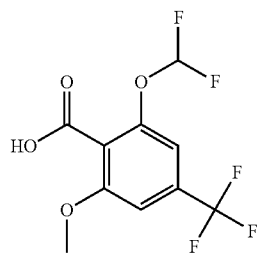

Step 1. Preparation of 2-Benzyloxy-6-methoxy-4-trifluoromethyl-benzonitrile

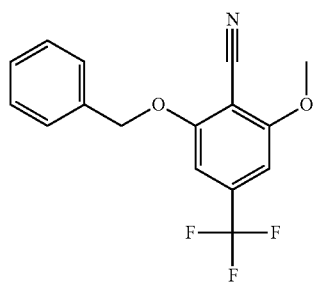

To a solution of 200 mg (0.813 mmol) 2-methoxy-6-nitro-4-trifluoromethyl-benzonitrile in 2 ml dioxane under argon at 0° C., was added 425.3 ul (4.065 mmol) benzyl alcohol, followed by a dropwise addition of a solution of 82.2 mg (1.260 mmol) potassium hydroxide in 600 ul water. The mixture was stirred at 0° C. for 30 minutes and then at room temperature overnight. The reaction mixture was poured into ice water. The resulting suspension was filtered and dried in vacuo to provide 196 mg (y: 78.5%) of the title compound as a white solid.

Step 2. Preparation of 2-benzyloxy-6-methoxy-4-trifluoromethyl-benzamide

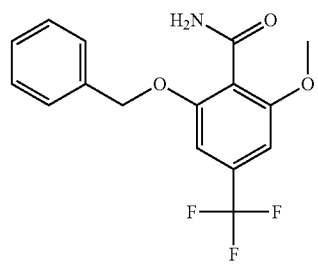

To a solution of 254 mg (6.350 mmol) sodium hydroxide in 2 ml water and 2 ml ethanol at room temperature under nitrogen, was added 195 mg (0.635 mmol) 2-benzyloxy-6-methoxy-4-trifluoromethyl-benzonitrile. The reaction mixture was heated in a 90° C. oil bath overnight. The reaction mixture was cooled to room temperature and 7 ml water was added. The product was collect by filtration and dried to provide 192 mg (y: 93%) of the title compound as a white solid. MS (m/e): 326.3 (MH+).

Step 3. Preparation of 2-benzyloxy-6-methoxy-4-trifluoromethyl-benzoic acid

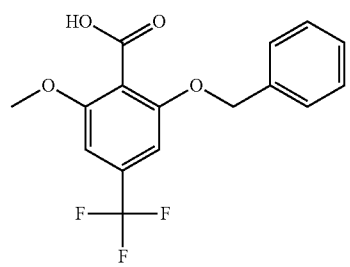

To a solution of 1.81 g (12.81 mmol) nitrosylsulfuric acid in 1.5 ml water at 0° C. under nitrogene, was added dropwise a suspension of 463 mg (1.423 mmol) 2-benzyloxy-6-methoxy-4-trifluoromethyl-benzamide in 2.9 ml dichloromethane. The reaction mixture was stirred at 0° C. for 4 hours. The reaction mixture was poured over ice and extracted with dichloromethane. The combined organic layers were dried over sodium sulfate, filtered and evaporated. The crude solid was purified with flash column chromatography on silica (20 g) eluting with a gradient formed from n-heptane and ethyl acetate (0%=>100% in 15 minutes) to provide 431 mg (y: 64.9% yield) of the title compound as a white solid. MS (m/e): 325.1 (M−H)

Step 4. Preparation of 2-benzyloxy-6-methoxy-4-trifluoromethyl-benzoic acid methyl ester

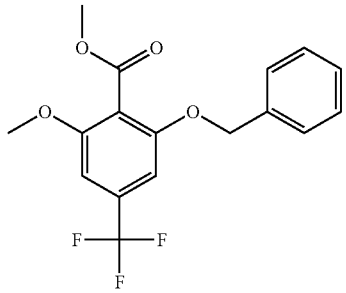

To a solution of 380 mg (1.165 mmol) 2-benzyloxy-6-methoxy-4-trifluoromethyl-benzoic acid in 3.8 ml N,N-dimethylformamide under nitrogen at room temperature, was added 177.1 mg (1.281 mmol) potassium carbonate and 87.2 ul (1.398 mmol) methyliodide. The mixture was stirred under nitrogen for 3 days. The mixture was poured into water. The aqueous layer was extracted once with ethyl acetate. The organic layer was washed once with water, dried over sodium sulfate, filtered and concentrated in vacuo. The crude light yellow oil (410 mg) was purified with flash column chromatography on silica (10 g) eluting with a gradient formed from n-heptane and ethyl acetate (0%=>10% in 15 minutes) to provide 352 mg (y: 88.8%) of the title compound as a colorless oil, which crystallized on standing. MS (m/e): 341.2 (MH+).

Step 5. Preparation of 2-hydroxy-6-methoxy-4-trifluoromethyl-benzoic acid methyl ester

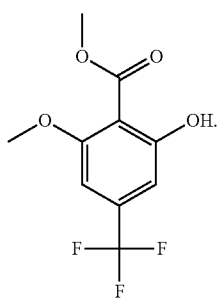

To a solution of 60 mg (0.176 mmol) 2-benzyloxy-6-methoxy-4-trifluoromethyl-benzoic acid methyl ester in 1 ml ethanol under nitrogen at room temperature, was added 8 mg (0.0071 mmol) Pd/C 10%. The mixture was stirred at room temperature under an hydrogen atmosphere for 4 hours. The catalyst was filtered, washed with dichloromethane and the filtrate was concentrated in vacuo to provide 38 mg (y: 86.1%) of the title compound as a white solid. MS (m/e): 249.0 (M−H).

Step 6. Preparation of 2-difluoromethoxy-6-methoxy-4-trifluoromethyl-benzoic acid methyl ester

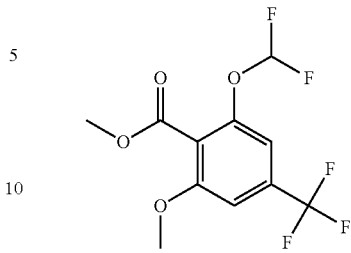

To a solution of 35 mg (0.140 mmol) 2-hydroxy-6-methoxy-4-trifluoromethyl-benzoic acid methyl ester in 350 ul N,N-dimethylformamide under nitrogen at room temperature, was added 29 mg (0.210 mmol) potassium carbonate, followed dropwise by 18.1 ul (0.168 mmol) methyl chlorodifluoroacetate. The reaction mixture was heated in a 65° C. oil bath for 22 hours. Water and ethyl acetate were added. Both phases were separated and the organic layer was washed 3 times with water. The organic layer was dried over sodium sulfate, filtered and concentrated in vacuo. The crude brown oil (49 mg) was purified with flash column chromatography on silica (10 g) eluting with a gradient formed from n-heptane and ethyl acetate (0%=>10% in 15 minutes) to provide 16 mg (y: 38.1%) of the title compound as a light yellow oil.

Step 7. Preparation of 2-Difluoromethoxy-6-methoxy-4-trifluoromethyl-benzoic acid To a solution of 85 mg (0.283 mmol) 2-difluoromethoxy-6-methoxy-4-trifluoromethyl-benzoic acid in 1.6 ml dioxane over mol-sieve at room temperature, was added a solution of 20.75 mg (0.849 mmol) LiOH in 0.8 ml water. The mixture was stirred at room temperature for 4 hours. The solvents were removed in vacuo. The residue was dissolved in water and extracted with diethyl ether. The aqueous layer was acidified with HCl 5M until pH 1 and extracted 3 times with ethyl acetate. The combined organic phases were dried over sodium sulfate, filtered and concentrated in vacuo to provide 12.5 mg (y: 15.4%) of the title compound as an oil. MS (m/e): 284.9 (M−H)

SYNTHESIS OF THE EXAMPLES

Examples 1 and 2 cis-2-Methoxy-6-methylsulfanyl-N-2-pyrrolidin-1-yl-cyclohexyl)-4-trifluoromethyl-benzamide and trans-2-methoxy-6-methylsulfanyl-N-2-pyrrolidin-1-yl-cyclohexyl)-4-trifluoromethyl-benzamide

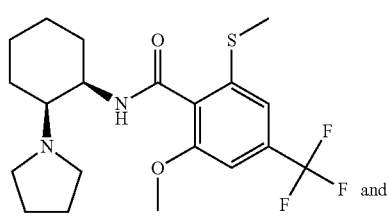

and

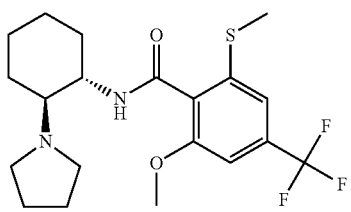

2-Methoxy-6-methylsulfanyl-N-(2-oxo-cyclohexyl)-4-trifluoromethyl-benzamide (intermediate B, 380 mg, 1.05 mmol) was dissolved in 10 mL tetrahydrofurane. Acetic acid (145 mg, 2.4 mmol) and pyrrolidine (97 mg, 1.4 mmol) were added and the reaction mixture was stirred 1 h at room temperature. Sodium triacetoxyborohydride (290 mg, 1.4 mmol) was added and stirring was continued at room temperature overnight. The mixture was extracted with 2N sodium carbonate solution and ethyl acetate. The combined organic phases were dried on sodium sulfate, filtered and evaporated. Purification of the residue by flash chromatography on silica gel (dichloromethane/methanol/ammonia 100:0:0→140:10:1) yielded cis-2-methoxy-6-methylsulfanyl-N-2-pyrrolidin-1-yl-cyclohexyl)-4-trifluoromethyl-benzamide as a light yellow solid (125 mg, 28%), MS: m/e=417.3 [(M+H)$^+$] and trans-2-methoxy-6-methylsulfanyl-N-2-pyrrolidin-1-yl-cyclohexyl)-4-trifluoromethyl-benzamide as a light yellow solid (28 mg, 6%), MS: m/e=417.3 [(M+H)$^+$].

Examples 3 and 4 cis-2-Methylsulfanyl-N-(2-pyrrolidin-1-yl-cyclohexyl)-4-trifluoromethyl-benzamide and trans-2-Methylsulfanyl-N-(2-pyrrolidin-1-yl-cyclohexyl)-4-trifluoromethyl-benzamide

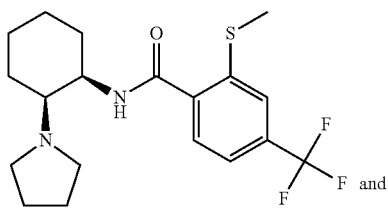

and

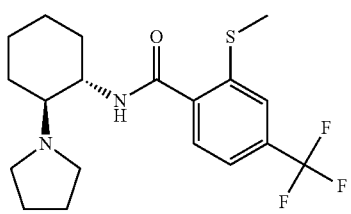

cis-2-Methylsulfanyl-N-(2-pyrrolidin-1-yl-cyclohexyl)-4-trifluoromethyl-benzamide, colorless oil, MS: m/e=387.2 [(M+H)$^+$], and trans-2-methylsulfanyl-N-(2-pyrrolidin-1-yl-cyclohexyl)-4-trifluoromethyl-benzamide, white solid, MS: m/e=387.2 [(M+H)$^+$], were prepared in accordance with the general method of example 1 and 2 from 2-methylsulfanyl-N-(2-oxo-cyclohexyl)-4-trifluoromethyl-benzamide (intermediate D) and pyrrolidine.

Example 5 cis-2-Methoxy-N-(2-pyrrolidin-1-yl-cyclohexyl)-4,6-bis-trifluoromethyl-benzamide

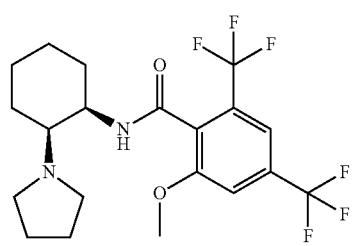

2,4-Bis(trifluoromethyl)-6-methoxy-benzoic acid (200 mg, 0.69 mmol) was dissolved in 5 mL dimethylformamide. N,N-Diisopropyl ethyl amine (359 mg, 2.8 mmol) and O-(7-azabenzotriazol-1-yl)-N,N,N',N'-tetramethyluronium hexafluorophosphate (264 mg, 0.69 mmol) were added. After 5 minutes of stirring at room temperature cis-2-pyrrolidin-1-yl-cyclohexylamine dihydrochloride (intermediate F) (171 mg, 0.71 mmol) was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (dichloromethane/methanol/ammonia 100:0:0→140:10:1) yielded cis-2-methoxy-N-(2-pyrrolidin-1-yl-cyclohexyl)-4,6-bis-trifluoromethyl-benzamide as a white solid (158 mg, 52%), MS: m/e=439.2 [(M+H)$^+$].

Example 6 and 7

(−)-cis-2-Methoxy-6-methylsulfanyl-N-(2-pyrrolidin-1-yl-cyclohexyl)-4-trifluoromethyl-benzamide and (+)-cis-2-Methoxy-6-methylsulfanyl-N-(2-pyrrolidin-1-yl-cyclohexyl)-4-trifluoromethyl-benzamide

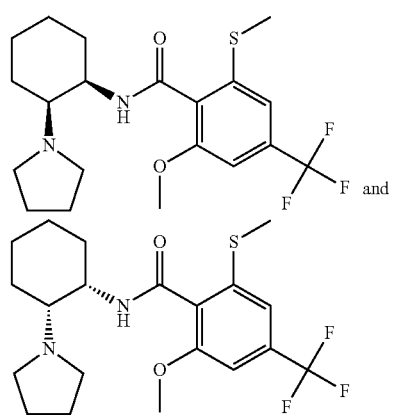

cis-2-Methoxy-6-methylsulfanyl-N-2-pyrrolidin-1-yl-cyclohexyl)-4-trifluoromethyl-benzamide (example 1) was separated on Chiralpak AD with 8% isopropanol in heptane. The first eluting enantiomer was (−)-cis-2-methoxy-6-methylsulfanyl-N-(2-pyrrolidin-1-yl-cyclohexyl)-4-trifluoromethyl-benzamide, the second enantiomer was (+)-cis-2-methoxy-6-methylsulfanyl-N-(2-pyrrolidin-1-yl-cyclohexyl)-4-trifluoromethyl-benzamide. The absolute stereochemistry was not determined.

Example 8 and 9

(−)-cis-2-Methylsulfanyl-N-(2-pyrrolidin-1-yl-cyclohexyl)-4-trifluoromethyl-benzamide and (+)-cis-2-Methylsulfanyl-N-(2-pyrrolidin-1-yl-cyclohexyl)-4-trifluoromethyl-benzamide

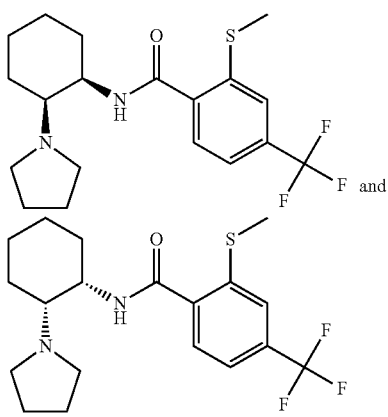

cis-2-Methylsulfanyl-N-(2-pyrrolidin-1-yl-cyclohexyl)-4-trifluoromethyl-benzamide (example 3) was separated on Chiralpak AD with 20% isopropanol in heptane. The first eluting enantiomer was (−)-cis-2-methylsulfanyl-N-(2-pyrrolidin-1-yl-cyclohexyl)-4-trifluoromethyl-benzamide, the second enantiomer was (+)-cis-2-methylsulfanyl-N-(2-pyrrolidin-1-yl-cyclohexyl)-4-trifluoromethyl-benzamide. The absolute configuration was not determined.

Example 10 cis-2-Methylsulfanyl-N-(2-morpholin-4-yl-cyclohexyl)-4-trifluoromethyl-benzamide

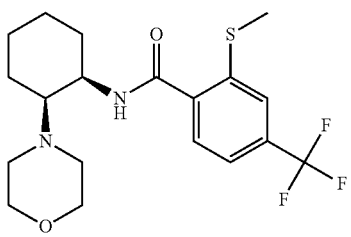

cis-N-(2-Amino-cyclohexyl)-2-methylsulfanyl-4-trifluoromethyl-benzamide (intermediate G) (264 mg, 0.79 mmol) was dissolved in 15 mL acetonitrile. Potassium carbonate (549 mg, 4 mmol) and bis(2-bromoethyl)ether (239 mg, 1 mmol) were added and the reaction mixture was refluxed overnight. The solvent was evaporated off. The residue was taken up in water and ethyl acetate and was extracted three times with ethyl acetate. The combined organic phases were dried on sodium sulfate, filtered and evaporated. Purification of the residue by flash chromatography on silica gel (dichloromethane/methanol/ammonia 100:0:0→140:10:1) yielded cis-2-methylsulfanyl-N-(2-morpholin-4-yl-cyclohexyl)-4-trifluoromethyl-benzamide as a light yellow gum (218 mg, 68%), MS: m/e=403.3 [(M+H)$^+$].

Example 11 cis-N-[2-(Cyclopropylmethyl-amino)-cyclohexyl]-2-methoxy-4,6-bis-trifluoromethyl-benzamide

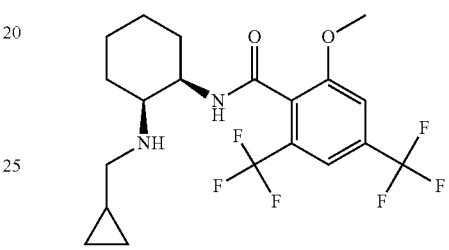

cis-N-(2-Amino-cyclohexyl)-2-methoxy-4,6-bis-trifluoromethyl-benzamide (intermediate H) (200 mg, 0.05 mmol) was dissolved in 10 mL methanol. Acetic acid (0.156 mg, 2.6 mmol) and cyclopropanecarboxaldehyde (73 mg, 1 mmol) were added and the reaction mixture was stirred 1 h at room temperature. Sodium triacetoxyborohydride (221 mg, 1 mmol) was added at stirring was continued at room temperature overnight. The mixture was extracted with 2N sodium carbonate solution and ethyl acetate. The combined organic phases were dried on sodium sulfate, filtered and evaporated. Crystallization with diisopropylether and a small amount of dichloromethane yielded cis-N-[2-(cyclopropylmethyl-amino)-cyclohexyl]-2-methoxy-4,6-bis-trifluoromethyl-benzamide as a white solid (83 mg, 36%), MS: m/e=439.3 [(M+H)$^+$].

Example 12 cis-N-(2-Azetidin-1-yl-cyclohexyl)-2-methoxy-4,6-bis-trifluoromethyl-benzamide

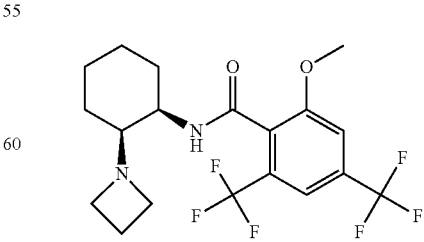

The title compound, light yellow solid, MS: m/e=425.2 [(M+H)$^+$], was prepared in accordance with the general method of example 10 from cis-N-(2-amino-cyclohexyl)-2-methoxy-4,6-bis-trifluoromethyl-benzamide (intermediate H) and 1,3-dibromopropane.

Example 13 cis-2-Methoxy-N-(2-piperidin-1-yl-cyclohexyl)-4,6-bis-trifluoromethyl-benzamide

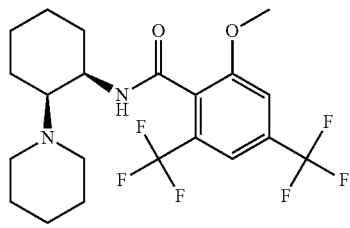

The title compound, white solid, MS: m/e=453.2 [(M+H)$^+$], was prepared in accordance with the general method of example 10 from cis-N-(2-amino-cyclohexyl)-2-methoxy-4,6-bis-trifluoromethyl-benzamide (intermediate H) and 1,5-dibromopentane.

Example 14 and 15

N-[2-(3-Hydroxy-pyrrolidin-1-yl)-cyclohexyl]-2-methoxy-4,6-bis-trifluoromethyl-benzamide (2 diastereomers)

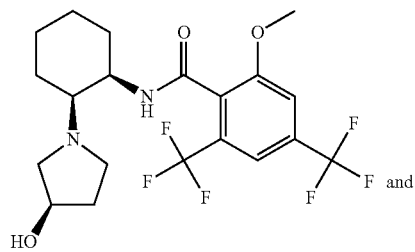

and

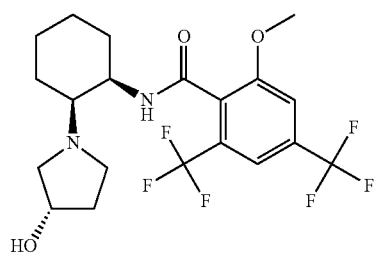

The title compounds, both light yellow solids, MS: m/e=455.3 [(M+H)$^+$], were prepared in accordance with the general method of example 10 from cis-N-(2-amino-cyclohexyl)-2-methoxy-4,6-bis-trifluoromethyl-benzamide (intermediate H) and 1,4-dibromo-2-butanol. The 2 diastereomers could be separated by column chromatography however the relative configuration was not assigned.

Example 16 cis-N-(2-Cyclobutylamino-cyclohexyl)-2-methoxy-4,6-bis-trifluoromethyl-benzamide

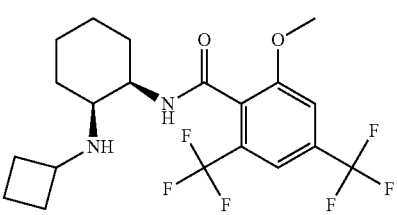

The title compound, off-white solid, MS: m/e=439.2 [(M+H)$^+$], was prepared in accordance with the general method of example 11 from cis-N-(2-amino-cyclohexyl)-2-methoxy-4,6-bis-trifluoromethyl-benzamide (intermediate H) and cyclobutanone.

Example 17

N-[(2-(3-Fluoro-pyrrolidin-1-yl)-cyclohexyl]-2-methoxy-4,6-bis-trifluoromethyl-benzamide (mixture of diastereomers)

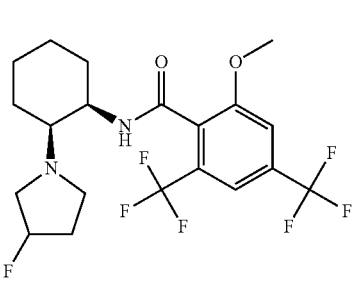

N-[2-(3-Hydroxy-pyrrolidin-1-yl)-cyclohexyl]-2-methoxy-4,6-bis-trifluoromethyl-benzamide (mixture of 2 diastereomers, example 14 and 15) (200 mg, 0.44 mmol) was dissolved in 5 mL dichloromethane. Bis(2-methoxyethyl)aminosulfur trifluoride (205 mg, 0.88 mmol) was added at −78° C. The reaction mixture was slowly warmed up and stirred at room temperature overnight. The reaction mixture was extracted with 1N NaOH and dichloromethane. The combined organic phases were dried on sodium sulfate, filtered and evaporated. Purification of the residue by flash chromatography on silica gel (dichloromethane/methanol 100:0→95:5) yielded N-[(2-(3-fluoro-pyrrolidin-1-yl)-cyclohexyl]-2-methoxy-4,6-bis-trifluoromethyl-benzamide as a mixture of diastereomers which was not separated, white solid (49 mg, 24%), MS: m/e=457.3 [(M+H)+].

Example 18 cis-N-(2-Cyclobutylamino-cyclohexyl)-2-methoxy-6-methylsulfanyl-4-trifluoromethyl-benzamide

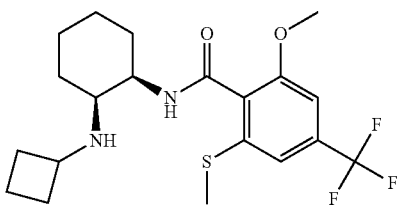

The title compound, colorless amorphous, MS: m/e=417.2 [(M+H)+], was prepared in accordance with the general method of example 11 from cis-N-(2-amino-cyclohexyl)-2-methoxy-6-methylsulfanyl-4-trifluoromethyl-benzamide (intermediate I) and cyclobutanone.

Example 19 cis-2-Ethyl-N-(2-pyrrolidin-1-yl-cyclohexyl)-4-trifluoromethyl-benzamide

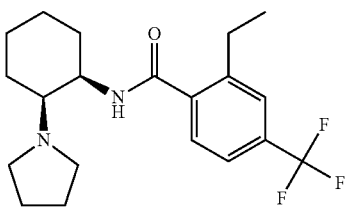

The title compound, white solid, MS: m/e=369.2 [(M+H)+], was prepared in accordance with the general method of example 5 from cis-2-pyrrolidin-1-yl-cyclohexylamine dihydrochloride (intermediate F) and 2-ethyl-4-(trifluoromethyl)-benzoic acid (CAS 854531-63-8).

Example 20 cis-N-[2-(4-Hydroxy-piperidin-1-yl)-cyclohexyl]-2-methoxy-4,6-bis-trifluoromethyl-benzamide

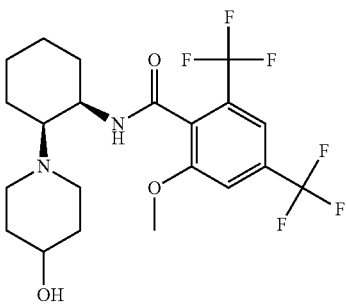

cis 2-Methoxy-N-2-(4-oxo-piperidin-1-yl)-cyclohexyl]-4,6-bis-trifluoromethyl-benzamide (intermediate J) (108 mg, 0.23 mmol) was dissolved in 5 mL methanol. Sodium borohydride (16 mg, 0.42 mmol) was added and the reaction mixture was stirred at 50° C. for 2 h. The reaction mixture was extracted with saturated sodium bicarbonate solution and dichloromethane. The combined organic phases were dried on sodium sulfate, filtered and evaporated. The crude product was pure cis-N-[2-(4-hydroxy-piperidin-1-yl)-cyclohexyl]-2-methoxy-4,6-bis-trifluoromethyl-benzamide, yellow foam (101 mg, 93%), MS: m/e=469.3 [(M+H)+].

Example 21

N-[(1RS,2SR)-2-(4,4-Difluoro-piperidin-1-yl)-cyclohexyl]-2-methoxy-4,6-bis-trifluoromethyl-benzamide

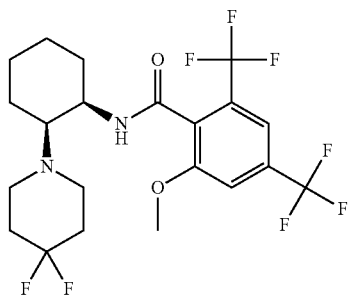

The title compound, white solid, MS: m/e=489.3 [(M+H)+], was prepared in accordance with the general method of example 17 from cis 2-methoxy-N-2-(4-oxo-piperidin-1-yl)-cyclohexyl]-4,6-bis-trifluoromethyl-benzamide (intermediate J) and bis(2-methoxyethyl)aminosulfur trifluoride.

Example 22

N-((1RS,2SR)-2-Cyclopentylamino-cyclohexyl)-2-methoxy-4,6-bis-trifluoromethyl-benzamide

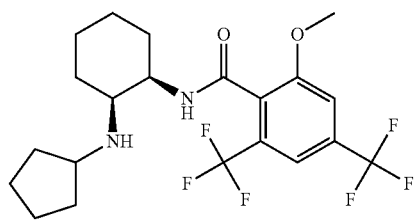

The title compound, off-white foam, MS: m/e=453.2 [(M+H)+], was prepared in accordance with the general method of example 11 from cis-N-(2-amino-cyclohexyl)-2-methoxy-4,6-bis-trifluoromethyl-benzamide (intermediate H) and cyclopentanone.

Example 23

2-Methoxy-N-[(1RS,2SR)-2-(tetrahydro-pyran-4-ylamino)-cyclohexyl]-4,6-bis-trifluoromethyl-benzamide

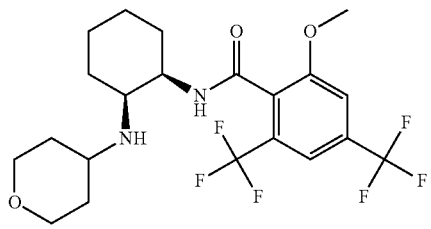

The title compound, off-white foam, MS: m/e=469.3 [(M+H)$^+$], was prepared in accordance with the general method of example 11 from cis-N-(2-amino-cyclohexyl)-2-methoxy-4,6-bis-trifluoromethyl-benzamide (intermediate H) and tetrahydro-4H-pyran-4-one.

Example 24 cis-N-[2-(3-Hydroxy-pyrrolidin-1-yl)-cyclohexyl]-2-methoxy-6-methylsulfanyl-4-trifluoromethyl-benzamide (mixture of 2 diastereomers)

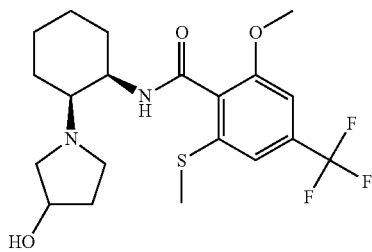

The title compound, light yellow foam, MS: m/e=433.2 [(M+H)$^+$], was prepared in accordance with the general method of example 10 from cis-N-(2-amino-cyclohexyl)-2-methoxy-6-methylsulfanyl-4-trifluoromethyl-benzamide (intermediate I) and 1,4-dibromo-2-butanol. The two diastereomers were not separated.

Example 25 cis-N-[2-(3-Fluoro-pyrrolidin-1-yl)-cyclohexyl]-2-methoxy-6-methylsulfanyl-4-trifluoromethyl-benzamide (mixture of 2 diasteremers)

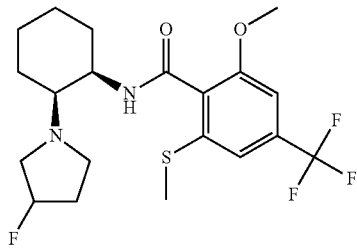

The title compound, light yellow solid, MS: m/e=435.3 [(M+H)$^+$], was prepared in accordance with the general method of example 17 from cis-N-[2-(3-Hydroxy-pyrrolidin-1-yl)-cyclohexyl]-2-methoxy-6-methylsulfanyl-4-trifluoromethyl-benzamide (example 24) and bis(2-methoxyethyl)aminosulfur trifluoride. The two diastereomers were not separated.

Example 26

N-[(1RS,2SR)-2-(Cyclobutyl-methyl-amino)-cyclohexyl]-2-methoxy-4,6-bis-trifluoromethyl-benzamide

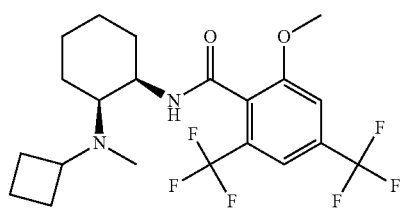

cis-N-(2-Cyclobutylamino-cyclohexyl)-2-methoxy-4,6-bis-trifluoromethyl-benzamide (example 16, 118 mg, 0.27 mmol) was dissolved in 2 mL formic acid. Formaldehyde (36% in water, 0.06 mL, 0.81 mmol) was added and the reaction mixture was stirred at 110° C. over night. The reaction mixture was basified by slow addition of 10 ml 1N sodium carbonate solution. The mixture was extracted three times with ethyl acetate. The combined organic phases were dried on sodium sulfate, filtered and evaporated. Purification of the residue by flash chromatography on silica gel (dichloromethane/methanol/ammonia 100:0:0→110:10:1) yielded the title compound as a white solid (46 mg, 38%), MS: m/e=453.2 [(M+H)$^+$].

Example 27

N-((1RS,2SR)-2-Isopropylamino-cyclohexyl)-2-methoxy-4,6-bis-trifluoromethyl-benzamide

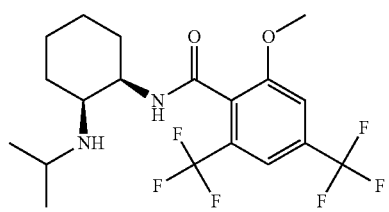

The title compound, off-white foam, MS: m/e=427.2 [(M+H)$^+$], was prepared in accordance with the general method of example 11 from cis-N-(2-amino-cyclohexyl)-2-methoxy-4,6-bis-trifluoromethyl-benzamide (intermediate H) and acetone.

Example 28 cis-2-Methoxy-N-[2-(2-methyl-pyrrolidin-1-yl)-cyclohexyl]-4,6-bis-trifluoromethyl-benzamide (mixture of 2 diastereomers)

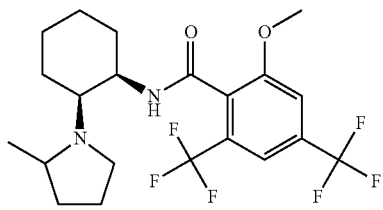

The title compound, MS: m/e=453.2 [(M+H)⁺], was prepared in accordance with the general method of example 10 from cis-N-(2-amino-cyclohexyl)-2-methoxy-4,6-bis-trifluoromethyl-benzamide (intermediate H) and 1,4-dibromopentane. The two diastereomers were not separated.

Example 29

N-((1RS,2SR)-2-Cyclohexylamino-cyclohexyl)-2-methoxy-4,6-bis-trifluoromethyl-benzamide

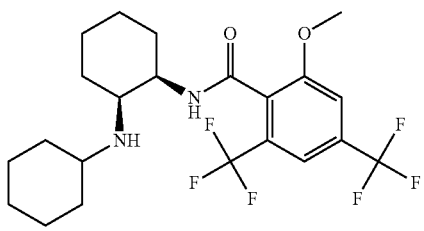

The title compound, light yellow solid, MS: m/e=467.2 [(M+H)⁺], was prepared in accordance with the general method of example 11 from cis-N-(2-amino-cyclohexyl)-2-methoxy-4,6-bis-trifluoromethyl-benzamide (intermediate H) and cyclohexanone.

Example 30 and 31

(+)-cis-N-(2-Cyclobutylamino-cyclohexyl)-2-methoxy-6-methylsulfanyl-4-trifluoromethyl-benzamide and (−)-cis-N-(2-Cyclobutylamino-cyclohexyl)-2-methoxy-6-methylsulfanyl-4-trifluoromethyl-benzamide

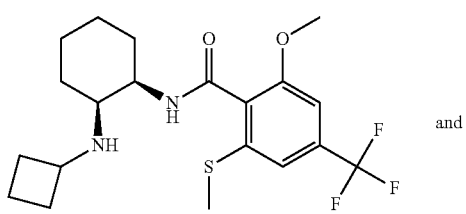
and

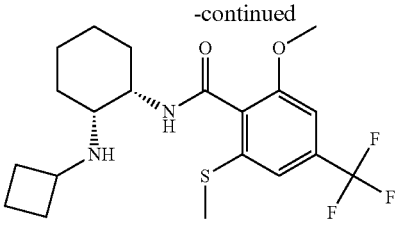

cis-N-(2-Cyclobutylamino-cyclohexyl)-2-methoxy-6-methylsulfanyl-4-trifluoromethyl-benzamide (example 18) was separated on Chiralpak AD with 5% ethanol in heptane. The first eluting enantiomer was (+)-cis-N-(2-cyclobutylamino-cyclohexyl)-2-methoxy-6-methylsulfanyl-4-trifluoromethyl-benzamide, the second enantiomer was (−)-cis-N-(2-cyclobutylamino-cyclohexyl)-2-methoxy-6-methylsulfanyl-4-trifluoromethyl-benzamide. The absolute configuration was not determined.

Example 32

2-Methoxy-N-[(1RS,2SR)-2-(tetrahydro-thiopyran-4-ylamino)-cyclohexyl]-4,6-bis-trifluoromethyl-benzamide

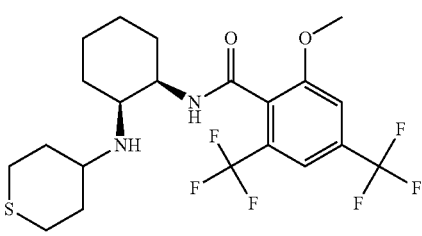

The title compound, white foam, MS: m/e=485.3 [(M+H)⁺], was prepared in accordance with the general method of example 11 from cis-N-(2-amino-cyclohexyl)-2-methoxy-4,6-bis-trifluoromethyl-benzamide (intermediate H) and tetrahydro-4H-thiopyran-4-one.

Example 33 and 34

(−)-cis-N-(2-Cyclopentylamino-cyclohexyl)-2-methoxy-4,6-bis-trifluoromethyl-benzamide and (+)-cis-N-(2-Cyclopentylamino-cyclohexyl)-2-methoxy-4,6-bis-trifluoromethyl-benzamide

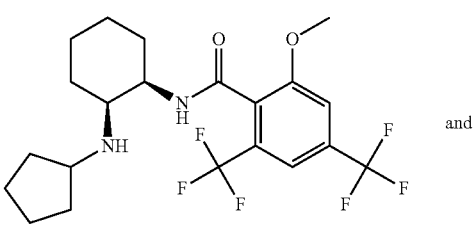
and

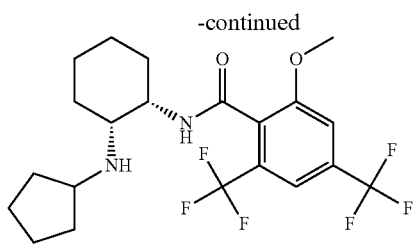

cis-N-(2-Cyclopentylamino-cyclohexyl)-2-methoxy-4,6-bis-trifluoromethyl-benzamide (example 22) was separated on Chiralpak AD with 3% ethanol in heptane. The first eluting enantiomer was (−)-cis-N-(2-cyclopentylamino-cyclohexyl)-2-methoxy-4,6-bis-trifluoromethyl-benzamide, the second enantiomer was (+)-cis-N-(2-cyclopentylamino-cyclohexyl)-2-methoxy-4,6-bis-trifluoromethyl-benzamide. The absolute configuration was not determined.

Example 35

N-[(1RS,2SR)-2-(2,5-Dimethyl-pyrrolidin-1-yl)-cyclohexyl]-2-methoxy-4,6-bis-trifluoromethyl-benzamide (mixture of 3 diastereomers)

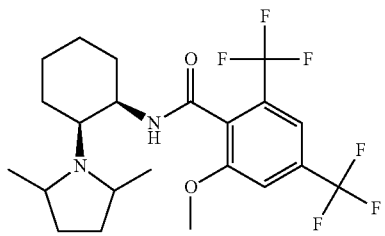

The title compound, MS: m/e=467.3 [(M+H)$^+$], was prepared in accordance with the general method of example 10 from cis-N-(2-amino-cyclohexyl)-2-methoxy-4,6-bis-trifluoromethyl-benzamide (intermediate H) and 2,5-dibromo-hexane. The 3 diastereomers were not separated.

Example 36

N-((1RS,2SR)-2-Pyrrolidin-1-yl-cyclohexyl)-2,4-bis-trifluoromethyl-benzamide

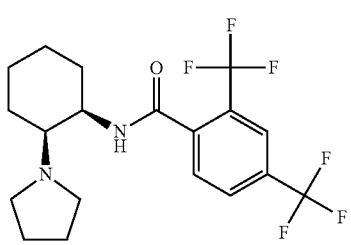

The title compound, white solid, MS: m/e=409.3 [(M+H)$^+$], was prepared in accordance with the general method of example 5 from cis-2-pyrrolidin-1-yl-cyclohexylamine dihydrochloride (intermediate F) and 2,4-bis(trifluoromethyl) benzoic acid.

Example 37

2-Methyl-N-((1RS,2SR)-2-pyrrolidin-1-yl-cyclohexyl)-4-trifluoromethyl-benzamide

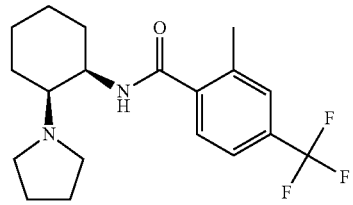

The title compound, white solid, MS: m/e=355.2 [(M+H)$^+$], was prepared in accordance with the general method of example 5 from cis-2-pyrrolidin-1-yl-cyclohexylamine dihydrochloride (intermediate F) and 2-methyl-4-trifluoromethyl-benzoic acid (CAS 23984-82-9).

Example 38

N-((1RS,2SR)-2-Cyclopentylamino-cyclohexyl)-2-methoxy-6-methylsulfanyl-4-trifluoromethyl-benzamide

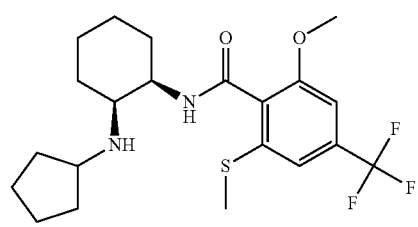

The title compound, light yellow solid, MS: m/e=431.3 [(M+H)$^+$], was prepared in accordance with the general method of example 11 from cis-N-(2-amino-cyclohexyl)-2-methoxy-6-methylsulfanyl-4-trifluoromethyl-benzamide (intermediate I) and cyclopentanone.

Example 39 and 40

(+)-N-(2-Cyclopentylamino-cyclohexyl)-2-methoxy-6-methylsulfanyl-4-trifluoromethyl-benzamide and (+N-(2-Cyclopentylamino-cyclohexyl)-2-methoxy-6-methylsulfanyl-4-trifluoromethyl-benzamide

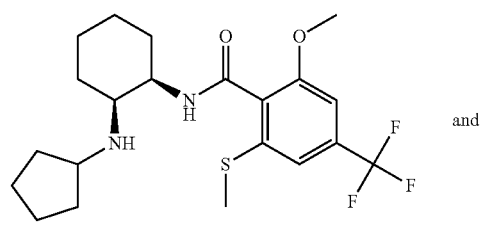

and

-continued

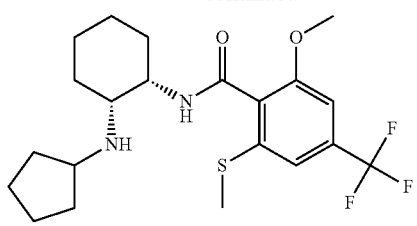

N-((1RS,2SR)-2-Cyclopentylamino-cyclohexyl)-2-methoxy-6-methylsulfanyl-4-trifluoromethyl-benzamide (example 38) was separated on Chiralpak AD with 4% ethanol in heptane. The optical rotation and the absolute configuration of the 2 enantiomers were not determined.

Example 41

N-((1RS,2SR)-2-Benzylamino-cyclohexyl)-2-methoxy-4,6-bis-trifluoromethyl-benzamide

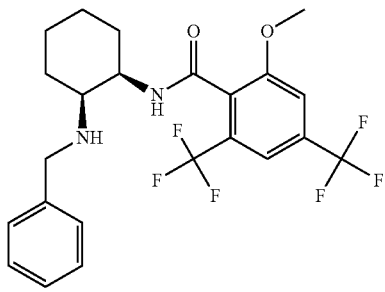

The title compound, colorless gum, MS: m/e=475.3 [(M+H)$^+$], was prepared in accordance with the general method of example 11 from cis-N-(2-amino-cyclohexyl)-2-methoxy-4,6-bis-trifluoromethyl-benzamide (intermediate H) and benzaldehyde.

Example 42 and 43

(−)-cis-2-Ethyl-N-(2-pyrrolidin-1-yl-cyclohexyl)-4-trifluoromethyl-benzamide and (+)-cis-2-Ethyl-N-(2-pyrrolidin-1-yl-cyclohexyl)-4-trifluoromethyl-benzamide

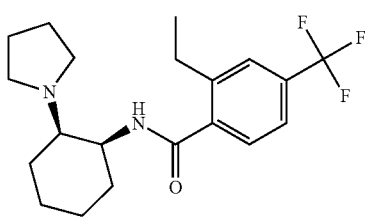 and

-continued

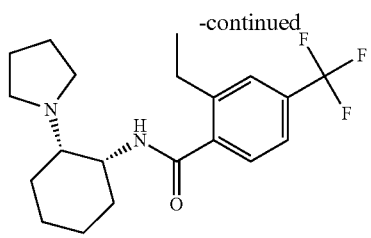

cis-2-Ethyl-N-(2-pyrrolidin-1-yl-cyclohexyl)-4-trifluoromethyl-benzamide (example 19) was separated on Chiralpak AD with 3% isopropanol in heptane. The first eluting enantiomer was (−)-cis-2-ethyl-N-(2-pyrrolidin-1-yl-cyclohexyl)-4-trifluoromethyl-benzamide, the second enantiomer was (+)-cis-2-ethyl-N-(2-pyrrolidin-1-yl-cyclohexyl)-4-trifluoromethyl-benzamide. The absolute configuration was not determined.

Example 44 cis-4-[2-(2-Methoxy-4,6-bis-trifluoromethyl-benzoylamino)-cyclohexylamino]-piperidine-1-carboxylic acid tert-butyl ester

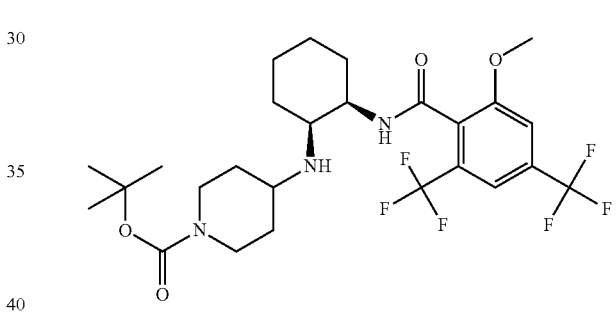

The title compound, colorless oil, MS: m/e=568.1 [(M+H)$^+$], was prepared in accordance with the general method of example 11 from cis-N-(2-amino-cyclohexyl)-2-methoxy-4,6-bis-trifluoromethyl-benzamide (intermediate H) and N-tert-butoxycarbonyl-4-piperidone.

Example 45 cis-2-Cyclopropyl-N-(2-pyrrolidin-1-yl-cyclohexyl)-4-trifluoromethyl-benzamide

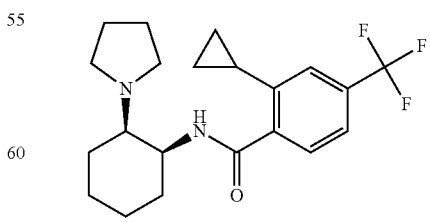

The title compound, white solid, MS: m/e=381.3 [(M+H)$^+$], was prepared in accordance with the general method of example 5 from cis-2-pyrrolidin-1-yl-cyclohexylamine dihydrochloride (intermediate F) and 2-cyclopropyl-4-trifluoromethyl-benzoic acid (intermediate K).

Example 46 cis-N-(2-Cyclopentylamino-cyclohexyl)-2-cyclopropyl-4-trifluoromethyl-benzamide

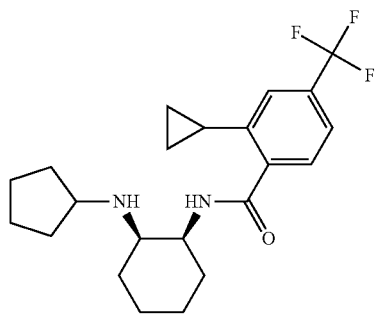

The title compound, yellow solid, MS: m/e=395.3 [(M+H)$^+$], was prepared in accordance with the general method of example 11 from cis-N-(2-amino-cyclohexyl)-2-cyclopropyl-4-trifluoromethyl-benzamide (intermediate L) and cyclopentanone.

Example 47 and 48

(−)-cis-2-Cyclopropyl-N-(2-pyrrolidin-1-yl-cyclohexyl)-4-trifluoromethyl-benzamide and (+)-cis-2-Cyclopropyl-N-(2-pyrrolidin-1-yl-cyclohexyl)-4-trifluoromethyl-benzamide

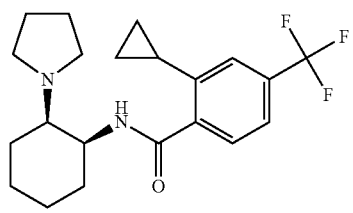

and

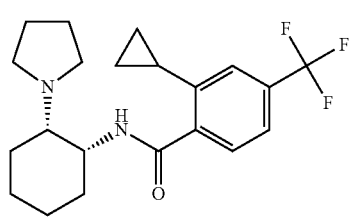

cis-2-Cyclopropyl-N-(2-pyrrolidin-1-yl-cyclohexyl)-4-trifluoromethyl-benzamide (example 45) was separated on Chiralpak AD with 10% ethanol in heptane. The first eluting enantiomer was (−)-cis-2-cyclopropyl-N-(2-pyrrolidin-1-yl-cyclohexyl)-4-trifluoromethyl-benzamide, the second enantiomer was (+)-cis-2-cyclopropyl-N-(2-pyrrolidin-1-yl-cyclohexyl)-4-trifluoromethyl-benzamide. The absolute configuration was not determined.

Example 49

N-[cis-(2-(1-Cyclopropyl-piperidin-4-ylamino)-cyclohexyl]-2-methoxy-4,6-bis-trifluoromethyl-benzamide

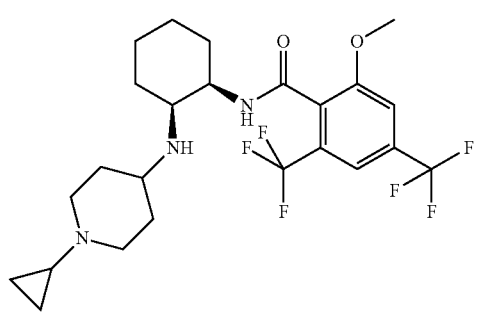

The title compound, light yellow solid, MS: m/e=508.3 [(M+H)$^+$], was prepared in accordance with the general method of example 11 from cis-N-(2-amino-cyclohexyl)-2-methoxy-4,6-bis-trifluoromethyl-benzamide (intermediate H) and 1-cyclopropyl-4-piperidone.

Example 50

N-[cis-2-(1-Acetyl-piperidin-4-ylamino)-cyclohexyl]-2-methoxy-4,6-bis-trifluoromethyl-benzamide

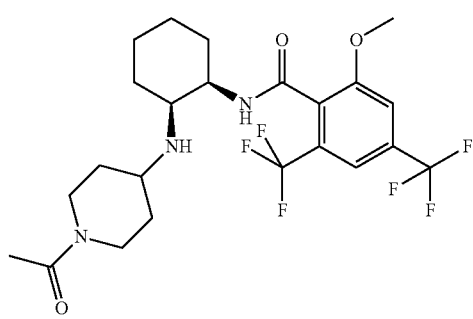

The title compound, light yellow solid, MS: m/e=510.4 [(M+H)$^+$], was prepared in accordance with the general method of example 11 from cis-N-(2-amino-cyclohexyl)-2-methoxy-4,6-bis-trifluoromethyl-benzamide (intermediate H) and 1-acetyl-4-piperidone.

Example 51

2-Methyl-N-((cis-2-pyrrolidin-1-yl-cyclohexyl)-4,6-bis-trifluoromethyl-benzamide

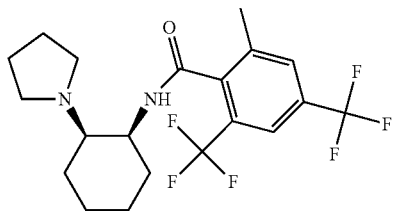

The title compound, white solid, MS: m/e=423.2 [(M+H)$^+$], was prepared in accordance with the general method of example 5 from cis-2-pyrrolidin-1-yl-cyclohexylamine dihydrochloride (intermediate F) and 2-methyl-4,6-bis(trifluoromethyl)benzoic acid (CAS 895580-37-7).

Example 52

2-Methylsulfanyl-N-((cis-2-pyrrolidin-1-yl-cyclohexyl)-4,6-bis-trifluoromethyl-benzamide

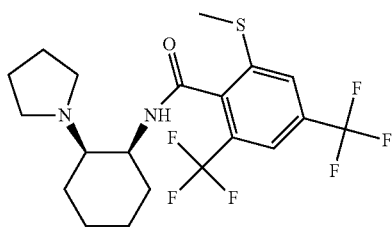

The title compound, white solid, MS: m/e=455.2 [(M+H)$^+$], was prepared in accordance with the general method of example 5 from cis-2-pyrrolidin-1-yl-cyclohexylamine dihydrochloride (intermediate F) and 2-methylthio-4,6-bis(trifluoromethyl)benzoic acid (CAS 896120-49-3).

Example 53 and 54

(−)-N-cis-(2-Cyclopentylamino-cyclohexyl)-2-cyclopropyl-4-trifluoromethyl-benzamide and (+)-N-cis-(2-Cyclopentylamino-cyclohexyl)-2-cyclopropyl-4-trifluoromethyl-benzamide

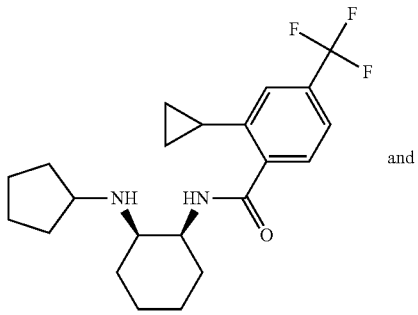

and

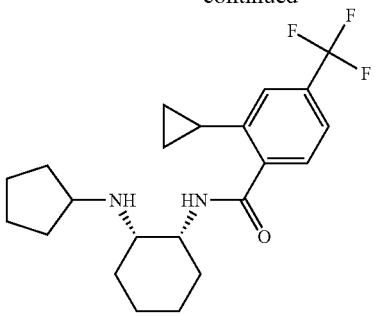

cis-N-(2-Cyclopentylamino-cyclohexyl)-2-cyclopropyl-4-trifluoromethyl-benzamide (example 46) was separated on Chiralpak AD with 2% ethanol in heptane. The first eluting enantiomer was (−)-N-cis-(2-cyclopentylamino-cyclohexyl)-2-cyclopropyl-4-trifluoromethyl-benzamide, the second enantiomer was (−)-N-cis-(2-cyclopentylamino-cyclohexyl)-2-cyclopropyl-4-trifluoromethyl-benzamide. The absolute configuration was not determined.

Example 55

2-Methoxy-6-methylsulfanyl-N-((1RS,2SR)-2-pyrrolidin-1-yl-cyclopentyl)-4-trifluoromethyl-benzamide

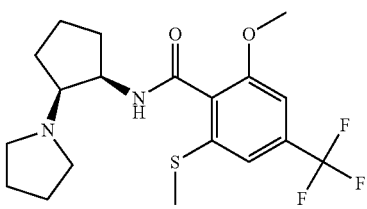

The title compound, brown gum, MS: m/e=403.4 [(M+H, was prepared in accordance with the general method of example 1 and 2 from 2-methoxy-6-methylsulfanyl-N-(2-oxo-cyclopentyl)-4-trifluoromethyl-benzamide (intermediate M) and pyrrolidine. The cis- and trans-isomer could be separated by column chromatography.

Example 56

N-((1RS,2SR)-2-Dimethylamino-cyclopentyl)-2-methoxy-6-methylsulfanyl-4-trifluoromethyl-benzamide

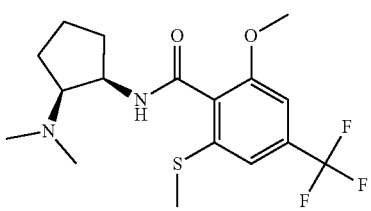

The title compound, brown gum, MS: m/e=377.3 [(M+H, was prepared in accordance with the general method of example 1 and 2 from 2-methoxy-6-methylsulfanyl-N-(2-oxo-cyclopentyl)-4-trifluoromethyl-benzamide (intermediate M) and dimethylamine. The cis- and trans-isomer could be separated by column chromatography.

Example 57

6-[(1SR,2RS)-2-(2-Methoxy-6-methylsulfanyl-4-trifluoromethyl-benzoylamino)-cyclopentyl]-2,6-diaza-spiro[3.3]heptane-2-carboxylic acid tert-butyl ester

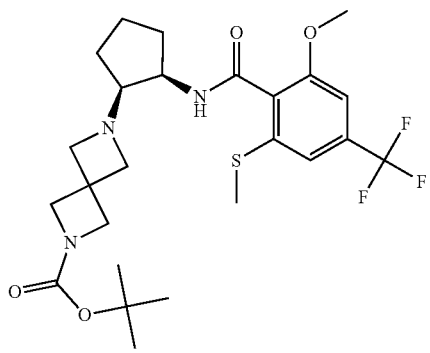

The title compound, brown gum, MS: m/e=530.3 [(M+H, was prepared in accordance with the general method of example 1 and 2 from 2-methoxy-6-methylsulfanyl-N-(2-oxo-cyclopentyl)-4-trifluoromethyl-benzamide (intermediate M) and 2,6-diazaspiro[3.3]heptane-2-carboxylic acid 1,1-dimethylethyl ester ethanedioate (CAS 1041026-71-4). The cis- and trans-isomer could be separated by column chromatography.

Example 58 and 59

(−)-2-Methoxy-6-methylsulfanyl-N-(2-pyrrolidin-1-yl-cyclopentyl)-4-trifluoromethyl-benzamide and (+)-2-Methoxy-6-methylsulfanyl-N-(2-pyrrolidin-1-yl-cyclopentyl)-4-trifluoromethyl-benzamide

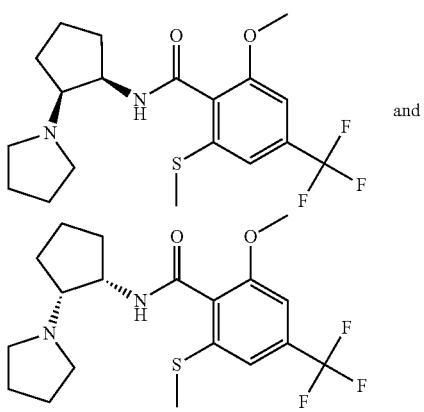

2-Methoxy-6-methylsulfanyl-N-((1RS,2SR)-2-pyrrolidin-1-yl-cyclopentyl)-4-trifluoromethyl-benzamide (example 54) was separated on Chiralpak AD with 2% isopropanol in heptane. The first eluting enantiomer was (−)-2-methoxy-6-methylsulfanyl-N-(2-pyrrolidin-1-yl-cyclopentyl)-4-trifluoromethyl-benzamide, the second enantiomer was (+)-2-methoxy-6-methylsulfanyl-N-(2-pyrrolidin-1-yl-cyclopentyl)-4-trifluoromethyl-benzamide. The absolute configuration was not determined.

Example 60

2-Methoxy-6-methylsulfanyl-N-((1RS,2SR)-2-morpholin-4-yl-cyclopentyl)-4-trifluoromethyl-benzamide

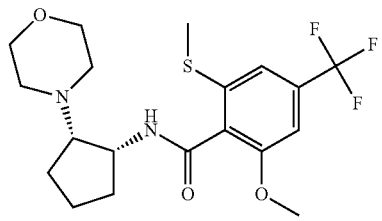

The title compound, white solid, MS: m/e=419.1 [(M+H)$^+$], was prepared in accordance with the general method of example 10 from N-((1RS,2SR)-2-amino-cyclopentyl)-2-methoxy-6-methylsulfanyl-4-trifluoromethyl-benzamide (intermediate O) and bis(2-bromoethyl)ether.

Example 61

N-((1RS,2SR)-2-Cyclobutylamino-cyclopentyl)-2-methoxy-6-methylsulfanyl-4-trifluoromethyl-benzamide

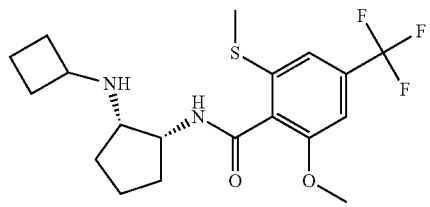

The title compound, white solid, MS: m/e=403.4 [(M+H)$^+$], was prepared in accordance with the general method of example 11 from N-((1RS,2SR)-2-amino-cyclopentyl)-2-methoxy-6-methylsulfanyl-4-trifluoromethyl-benzamide (intermediate O) and cyclobutanone.

Example 62 and 63

(−)-cis-N-(-2-Cyclobutylamino-cyclopentyl)-2-methoxy-6-methylsulfanyl-4-trifluoromethyl-benzamide and (+)-cis-N-(-2-Cyclobutylamino-cyclopentyl)-2-methoxy-6-methylsulfanyl-4-trifluoromethyl-benzamide

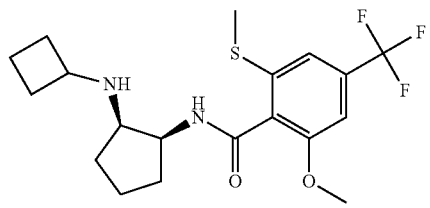

and

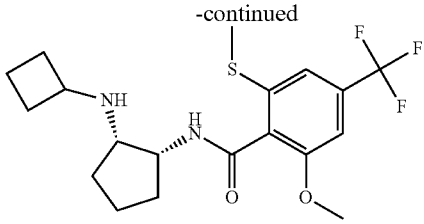

N-((1RS,2SR)-2-Cyclobutylamino-cyclopentyl)-2-methoxy-6-methylsulfanyl-4-trifluoromethyl-benzamide (example 61) was separated on Chiralpak AD with 10% ethanol in heptane. The first eluting enantiomer was (−)-cis-N-(-2-cyclobutylamino-cyclopentyl)-2-methoxy-6-methylsulfanyl-4-trifluoromethyl-benzamide, the second enantiomer was (+)-cis-N-(-2-Cyclobutylamino-cyclopentyl)-2-methoxy-6-methylsulfanyl-4-trifluoromethyl-benzamide. The absolute configuration was not determined.

Example 64

N-[(1RS,2SR)-2-(3-Hydroxy-pyrrolidin-1-yl)-cyclopentyl]-2-methoxy-6-methylsulfanyl-4-trifluoromethyl-benzamide (mixture of 2 diastereomers)

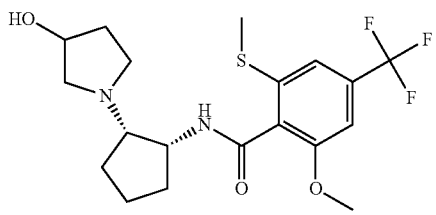

The title compound, colorless gum, MS: m/e=419.2 [(M+H)⁺], was prepared in accordance with the general method of example 10 from N-((1RS,2SR)-2-amino-cyclopentyl)-2-methoxy-6-methylsulfanyl-4-trifluoromethyl-benzamide (intermediate O) and 1,4-dibromo-2-butanol.

Example 65

N-((1RS,2SR)-2-Cyclopentylamino-cyclopentyl)-2-methoxy-6-methylsulfanyl-4-trifluoromethyl-benzamide

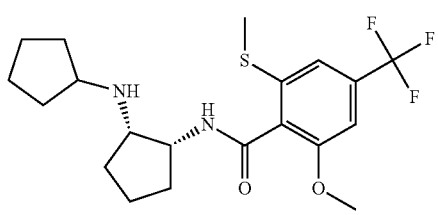

The title compound, off-white solid, MS: m/e=417.3 [(M+H)⁺], was prepared in accordance with the general method of example 11 from N-((1RS,2SR)-2-amino-cyclopentyl)-2-methoxy-6-methylsulfanyl-4-trifluoromethyl-benzamide (intermediate O) and cyclopentanone.

Example 66

2-Methoxy-6-methylsulfanyl-N-[(1RS,2SR)-2-(tetrahydro-pyran-4-ylamino)-cyclopentyl]-4-trifluoromethyl-benzamide

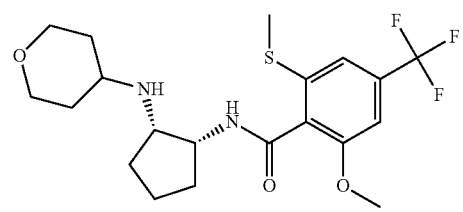

The title compound, white solid, MS: m/e=433.2 [(M+H)⁺], was prepared in accordance with the general method of example 11 from N-((1RS,2SR)-2-amino-cyclopentyl)-2-methoxy-6-methylsulfanyl-4-trifluoromethyl-benzamide (intermediate O) and tetrahydro-4H-pyran-4-one.

Example 67

N-[(1RS,2SR)-2-(3-Fluoro-pyrrolidin-1-yl)-cyclopentyl]-2-methoxy-6-methylsulfanyl-4-trifluoromethyl-benzamide (mixture of 2 diasteremers)

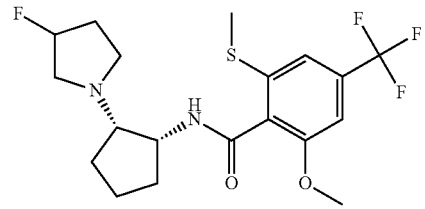

The title compound, light yellow solid, MS: m/e=421.1 [(M+H)⁺], was prepared in accordance with the general method of example 17 from N-[(1RS,2SR)-2-(3-hydroxy-pyrrolidin-1-yl)-cyclopentyl]-2-methoxy-6-methylsulfanyl-4-trifluoromethyl-benzamide (example 63) and bis(2-methoxyethyl)aminosulfur trifluoride. The two diastereomers were not separated.

Example 68 and 69

(−)-N-(2-Cyclopentylamino-cyclopentyl)-2-methoxy-6-methylsulfanyl-4-trifluoromethyl-benzamide and (+)-N-(2-Cyclopentylamino-cyclopentyl)-2-methoxy-6-methylsulfanyl-4-trifluoromethyl-benzamide

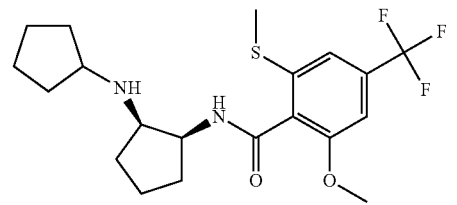

and

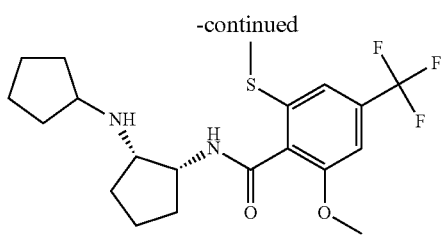

N-((1RS,2SR)-2-Cyclopentylamino-cyclopentyl)-2-methoxy-6-methylsulfanyl-4-trifluoromethyl-benzamide (example 65) was separated on Chiralpak AD with 5% ethanol in heptane. The first eluting enantiomer was (−)-N-(2-cyclopentylamino-cyclopentyl)-2-methoxy-6-methylsulfanyl-4-trifluoromethyl-benzamide, the second enantiomer was (−)-N-(2-cyclopentylamino-cyclopentyl)-2-methoxy-6-methylsulfanyl-4-trifluoromethyl-benzamide. The absolute configuration was not determined.

Example 70 cis-2-Methoxy-N-(2-pyrrolidin-1-yl-cyclopentyl)-4,6-bis-trifluoromethyl-benzamide

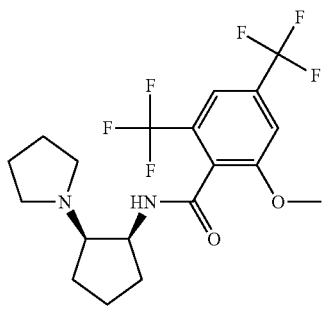

The title compound, white solid, MS: m/e=425.2 [(M+H)$^+$], was prepared in accordance with the general method of example 5 from cis-2-pyrrolidin-1-yl-cyclopentylamine (intermediate Q) and 2-methoxy-4,6-bis(trifluoromethyl)benzoic acid.

Example 71

2-Methoxy-6-methylsulfanyl-N-[(1RS,2SR)-2-(4-oxo-piperidin-1-yl)-cyclopentyl]-4-trifluoromethyl-benzamide

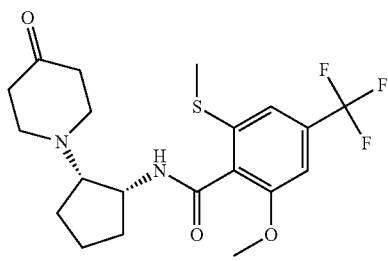

The title compound, yellow gum, MS: m/e=431.3 [(M+H)$^+$], was prepared in accordance with the general method of intermediate J from N-((1RS,2SR)-2-amino-cyclopentyl)-2-methoxy-6-methylsulfanyl-4-trifluoromethyl-benzamide (intermediate O) and 1-ethyl-1-methyl-4-oxo-piperidinium iodide.

Example 72 cis-2-Methyl-N-(2-pyrrolidin-1-yl-cyclopentyl)-4-trifluoromethyl-benzamide

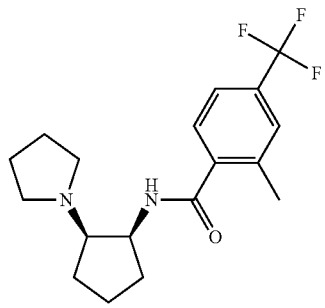

The title compound, yellow gum, MS: m/e=341.3 [(M+H)$^+$], was prepared in accordance with the general method of example 5 from cis-2-pyrrolidin-1-yl-cyclopentylamine (intermediate Q) and 2-methyl-4-trifluoromethyl-benzoic acid (CAS 23984-82-9).

Example 73

N-(cis-2-Pyrrolidin-1-yl-cyclopentyl)-2,4-bis-trifluoromethyl-benzamide

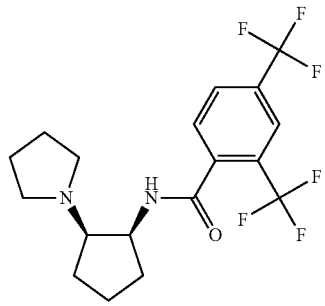

The title compound, yellow solid, MS: m/e=395.2 [(M+H)$^+$], was prepared in accordance with the general method of example 5 from cis-2-pyrrolidin-1-yl-cyclopentylamine (intermediate Q) and 2,4-bis(trifluoromethyl)benzoic acid.

Example 74

N-[(1RS,2SR)-2-(4-Hydroxy-piperidin-1-yl)-cyclopentyl]-2-methoxy-6-methylsulfanyl-4-trifluoromethyl-benzamide

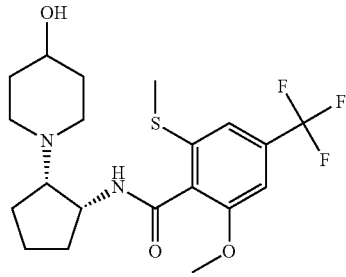

The title compound, white foam, MS: m/e=433.4 [(M+H)+], was prepared in accordance with the general method of example 20 from 2-methoxy-6-methylsulfanyl-N-[(1RS,2SR)-2-(4-oxo-piperidin-1-yl)-cyclopentyl]-4-trifluoromethyl-benzamide (example 70).

Example 75 cis-2,6-Dimethyl-N-(2-pyrrolidin-1-yl-cyclopentyl)-benzamide

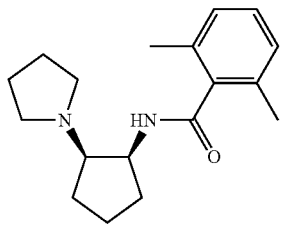

The title compound, white solid, MS: m/e=287.3 [(M+H)+], was prepared in accordance with the general method of example 5 from cis-2-pyrrolidin-1-yl-cyclopentylamine (intermediate Q) and 2,6-dimethyl benzoic acid.

Example 76 cis-2-Methylsulfanyl-N-(2-pyrrolidin-1-yl-cyclopentyl)-4-trifluoromethyl-benzamide

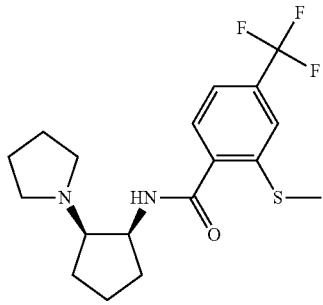

The title compound, light yellow oil, MS: m/e=372.2 [(M+H)+], was prepared in accordance with the general method of example 5 from cis-2-pyrrolidin-1-yl-cyclopentylamine (intermediate Q) and 2-methylsulfanyl-4-trifluoromethyl-benzoic acid (intermediate C).

Example 77 cis-4-Chloro-2-methyl-N-(2-pyrrolidin-1-yl-cyclopentyl)-benzamide

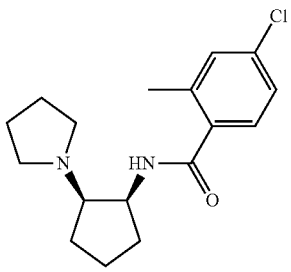

The title compound, light brown viscous oil, MS: m/e=307.2 [(M+H)+], was prepared in accordance with the general method of example 5 from cis-2-pyrrolidin-1-yl-cyclopentylamine (intermediate Q) and 4-chloro-2-methylbenzoic acid.

Example 78 and 79

(−)-N-(2-Pyrrolidin-1-yl-cyclopentyl)-2,4-bis-trifluoromethyl-benzamide and (+)-N-(2-Pyrrolidin-1-yl-cyclopentyl)-2,4-bis-trifluoromethyl-benzamide

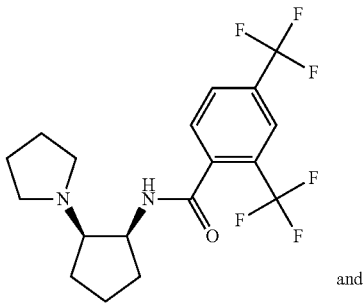

and

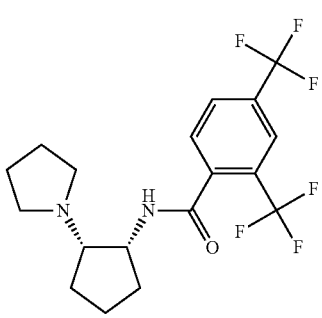

N-(cis-2-Pyrrolidin-1-yl-cyclopentyl)-2,4-bis-trifluoromethyl-benzamide (example 72) was separated on Chiralpak AD with 2% ethanol in heptane. The first eluting enantiomer was (−)-N-(2-pyrrolidin-1-yl-cyclopentyl)-2,4-bis-trifluoromethyl-benzamide, the second enantiomer was (+)-N-(2- pyrrolidin-1-yl-cyclopentyl)-2,4-bis-trifluoromethyl-benzamide. The absolute configuration was not determined.

Example 80 cis-2-Ethyl-N-(2-pyrrolidin-1-yl-cyclopentyl)-4-trifluoromethyl-benzamide

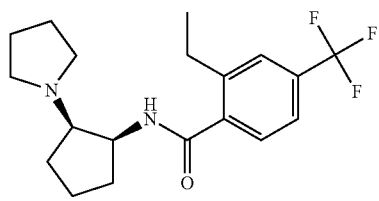

The title compound, white solid, MS: m/e=355.2 [(M+H)⁺], was prepared in accordance with the general method of example 5 from cis-2-pyrrolidin-1-yl-cyclopentylamine (intermediate Q) and 2-ethyl-4-(trifluoromethyl)-benzoic acid (CAS 854531-63-8).

Example 81 cis-2-Methoxy-N-(2-pyrrolidin-1-yl-cyclopentyl)-6-trifluoromethyl-benzamide

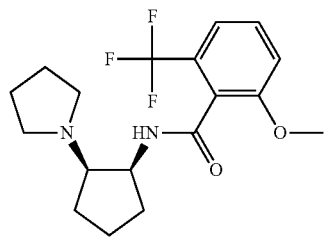

The title compound, off-white solid, MS: m/e=357.2 [(M+H)⁺], was prepared in accordance with the general method of example 5 from cis-2-pyrrolidin-1-yl-cyclopentylamine (intermediate Q) and 2-methoxy-6-trifluoromethylbenzoic acid.

Example 82 and 83

(−)-2,6-Dimethyl-N-(2-pyrrolidin-1-yl-cyclopentyl)-benzamide and (+)-2,6-Dimethyl-N-(2-pyrrolidin-1-yl-cyclopentyl)-benzamide

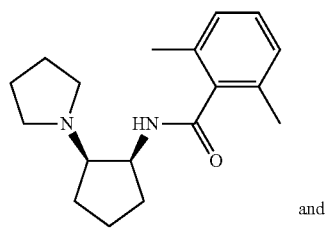

and

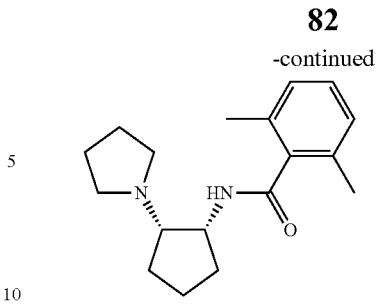

cis-2,6-Dimethyl-N-(2-pyrrolidin-1-yl-cyclopentyl)-benzamide (example 75) was separated on Reprosil Chiral NR with 10% ethanol in heptane. The first eluting enantiomer was (−)-2,6-dimethyl-N-(2-pyrrolidin-1-yl-cyclopentyl)-benzamide, the second enantiomer was (+)-2,6-dimethyl-N-(2-pyrrolidin-1-yl-cyclopentyl)-benzamide. The absolute configuration was not determined.

Example 84 and 85

(+)-2-Methylsulfanyl-N-(2-pyrrolidin-1-yl-cyclopentyl)-4-trifluoromethyl-benzamide and (−)-2-Methylsulfanyl-N-(2-pyrrolidin-1-yl-cyclopentyl)-4-trifluoromethyl-benzamide

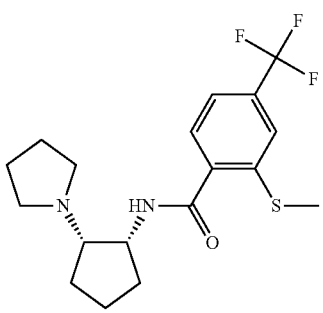

and

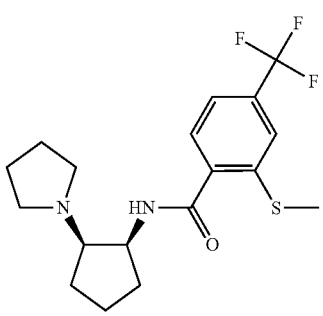

cis-2-Methylsulfanyl-N-(2-pyrrolidin-1-yl-cyclopentyl)-4-trifluoromethyl-benzamide (example 76) was separated on Lux 2 Cellulose with 10% ethanol in heptane. The first eluting enantiomer was (+)-2-methylsulfanyl-N-(2-pyrrolidin-1-yl-cyclopentyl)-4-trifluoromethyl-benzamide, the second enantiomer was (−)-2-methylsulfanyl-N-(2-pyrrolidin-1-yl-cyclopentyl)-4-trifluoromethyl-benzamide. The absolute configuration was not determined.

Example 86 cis-2-Chloro-N-(2-pyrrolidin-1-yl-cyclopentyl)-3-trifluoromethyl-benzamide

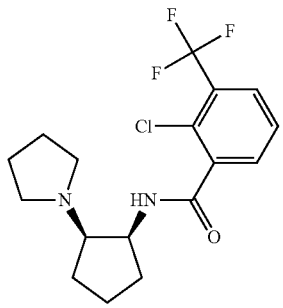

The title compound, yellow solid, MS: m/e=361.3 [(M+H)$^+$], was prepared in accordance with the general method of example 5 from cis-2-pyrrolidin-1-yl-cyclopentylamine (intermediate Q) and 2-chloro-3-trifluoromethylbenzoic acid.

Example 87 cis-2-Methoxy-6-methyl-N-(2-pyrrolidin-1-yl-cyclopentyl)-benzamide

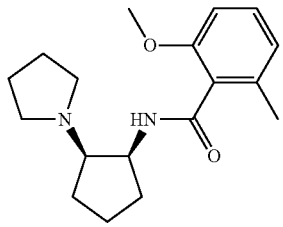

The title compound, white solid, MS: m/e=303.4 [(M+H)$^+$], was prepared in accordance with the general method of example 5 from cis-2-pyrrolidin-1-yl-cyclopentylamine (intermediate Q) and 2-methoxy-6-methylbenzoic acid.

Example 88 cis-4-Chloro-N-(2-pyrrolidin-1-yl-cyclopentyl)-2-trifluoromethyl-benzamide

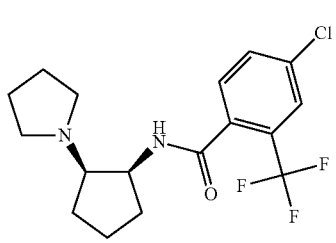

The title compound, yellow oil, MS: m/e=361.3 [(M+H)$^+$], was prepared in accordance with the general method of example 5 from cis-2-pyrrolidin-1-yl-cyclopentylamine (intermediate Q) and 4-chloro-2-(trifluoromethyl)benzoic acid.

Example 89 cis-N-(2-Cyclopentylamino-cyclopentyl)-2-ethyl-4-trifluoromethyl-benzamide

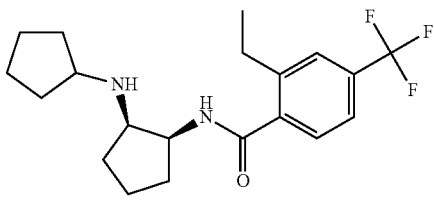

The title compound, white solid, MS: m/e=369.2 [(M+H)$^+$], was prepared in accordance with the general method of example 11 from cis-N-(2-Amino-cyclopentyl)-2-ethyl-4-trifluoromethyl-benzamide (intermediate S) and cyclopentanone.

Example 90

2,4,6-Trimethyl-cis-N-(2-pyrrolidin-1-yl-cyclopentyl)-benzamide

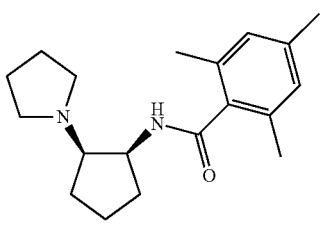

The title compound, white solid, MS: m/e=301.2 [(M+H)$^+$], was prepared in accordance with the general method of example 5 from cis-2-pyrrolidin-1-yl-cyclopentylamine (intermediate Q) and 2,4,6-trimethylbenzoic acid.

Example 91

2-Cyclopropyl-cis-N-(2-pyrrolidin-1-yl-cyclopentyl)-4-trifluoromethyl-benzamide

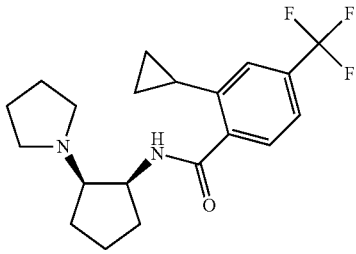

The title compound, white solid, MS: m/e=367.2 [(M+H)⁺], was prepared in accordance with the general method of example 5 from cis-2-pyrrolidin-1-yl-cyclopentylamine (intermediate Q) and 2-cyclopropyl-4-trifluoromethyl-benzoic acid (intermediate K).

Example 92 and 93

(+)-N-(2-Cyclopentylamino-cyclopentyl)-2-ethyl-4-trifluoromethyl-benzamide and (−)-N-(2-Cyclopentylamino-cyclopentyl)-2-ethyl-4-trifluoromethyl-benzamide

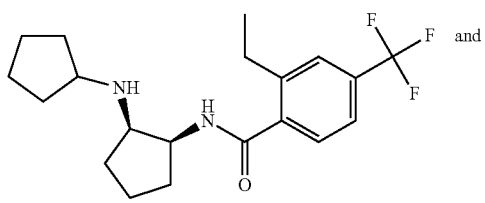

and

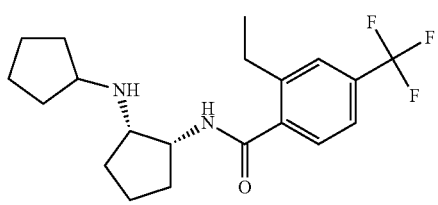

cis-N-(2-Cyclopentylamino-cyclopentyl)-2-ethyl-4-trifluoromethyl-benzamide (example 89) was separated on Chiralpak AD with 4% ethanol in heptane. The first eluting enantiomer was (+)-N-(2-cyclopentylamino-cyclopentyl)-2-ethyl-4-trifluoromethyl-benzamide, the second enantiomer was (−)-N-(2-cyclopentylamino-cyclopentyl)-2-ethyl-4-trifluoromethyl-benzamide. The absolute configuration was not determined.

Example 94 cis-2-Ethyl-6-methyl-N-(2-pyrrolidin-1-yl-cyclopentyl)-benzamide

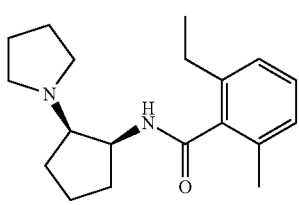

The title compound, white solid, MS: m/e=301.3 [(M+H)⁺], was prepared in accordance with the general method of example 5 from cis-2-pyrrolidin-1-yl-cyclopentylamine (intermediate Q) and 2-ethyl-6-methylbenzoic acid (CAS 106976-50-5).

Example 95 cis-2,6-Diethyl-N-(2-pyrrolidin-1-yl-cyclopentyl)-benzamide

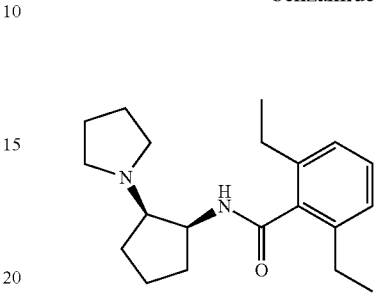

The title compound, white solid, MS: m/e=315.2 [(M+H)⁺], was prepared in accordance with the general method of example 5 from cis-2-pyrrolidin-1-yl-cyclopentylamine (intermediate Q) and 2,6-diethylbenzoic acid.

Example 96 and 97

(−)-2-Cyclopropyl-N-cis-(-2-pyrrolidin-1-yl-cyclopentyl)-4-trifluoromethyl-benzamide and (+)-2-Cyclopropyl-N-cis-(-2-pyrrolidin-1-yl-cyclopentyl)-4-trifluoromethyl-benzamide

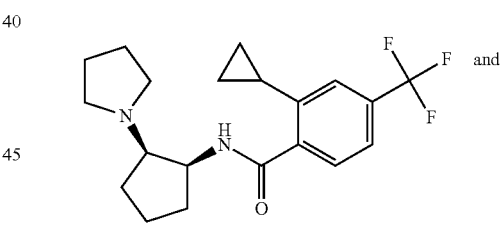

and

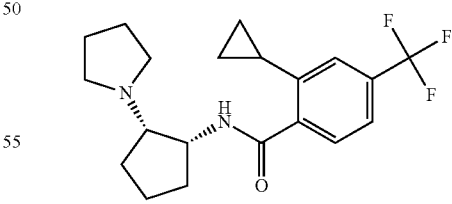

2-Cyclopropyl-cis-N-(2-pyrrolidin-1-yl-cyclopentyl)-4-trifluoromethyl-benzamide (example 91) was separated on Reprosil Chiral NR with 5% ethanol in heptane. The first eluting enantiomer was (−)-2-cyclopropyl-N-cis-(-2-pyrrolidin-1-yl-cyclopentyl)-4-trifluoromethyl-benzamide, the second enantiomer was (+)-2-cyclopropyl-N-cis-(-2-pyrrolidin1-yl-cyclopentyl)-4-trifluoromethyl-benzamide. The absolute configuration was not determined. -

Example 98 cis-2-Cyclopropyl-6-ethyl-N-(2-pyrrolidin-1-yl-cyclopentyl)-benzamide

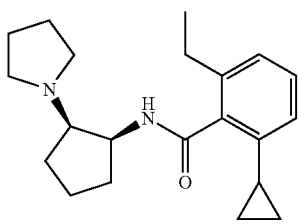

The title compound, white solid, MS: m/e=327.4 [(M+H)$^+$], was prepared in accordance with the general method of example 5 from cis-2-pyrrolidin-1-yl-cyclopentylamine (intermediate Q) and 2-cyclopropyl-6-ethyl-benzoic acid (intermediate T).

Example 99

2-Ethyl-3-methyl-N-cis-(2-pyrrolidin-1-yl-cyclopentyl)-4-trifluoromethyl-benzamide

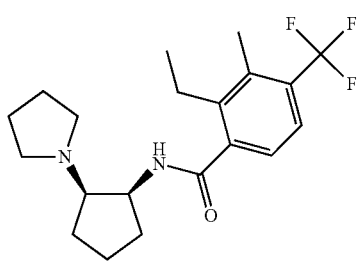

The title compound, light yellow oil, MS: m/e=369.2 [(M+H)$^+$], was prepared in accordance with the general method of example 5 from cis-2-pyrrolidin-1-yl-cyclopentylamine (intermediate Q) and 2-ethyl-3-methyl-4-trifluoromethyl-benzoic acid (intermediate U).

Example 100

2-Methoxy-3-methyl-N-cis-(2-pyrrolidin-1-yl-cyclopentyl)-4-trifluoromethyl-benzamide

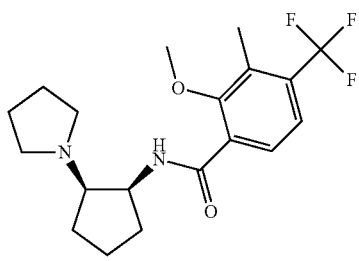

The title compound, colorless oil, MS: m/e=371.2 [(M+H)$^+$], was prepared in accordance with the general method of example 5 from cis-2-pyrrolidin-1-yl-cyclopentylamine (intermediate Q) and 2-methoxy-3-methyl-4-trifluoromethyl-benzoic acid (intermediate V).

Example 101

2-Bromo-6-methoxy-N-cis-(2-pyrrolidin-1-yl-cyclopentyl)-4-trifluoromethyl-benzamide

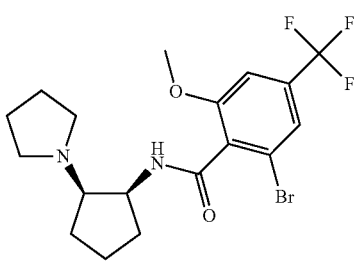

The title compound, yellow oil, MS: m/e=435.2/436.9 [(M+H)$^+$], was prepared in accordance with the general method of example 5 from cis-2-pyrrolidin-1-yl-cyclopentylamine (intermediate Q) and 2-bromo-6-methoxy-4-trifluoromethyl-benzoic acid (intermediate W).

Example 102

N-((1SR,2RS)-2-Cyclopentylamino-cyclopentyl)-2-cyclopropyl-4-trifluoromethyl-benzamide

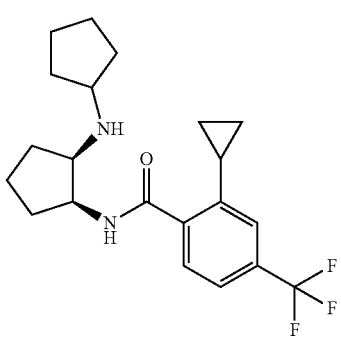

The title compound, brown oil, MS: m/e=381.4 [(M+H)$^+$], was prepared in accordance with the general method of example 5 from (1RS,2SR)-N-cyclopentyl-cyclopentane-1,2-diamine (intermediate AE) and 2-cyclopropyl-4-trifluoromethyl-benzoic acid (intermediate K).

Example 103 cis-2-Methyl-N-(2-pyrrolidin-1-yl-cyclopentyl)-4,6-bis-trifluoromethyl-benzamide

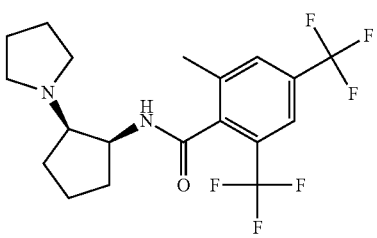

The title compound, white solid, MS: m/e=409.3 [(M+H)+], was prepared in accordance with the general method of example 5 from cis-2-pyrrolidin-1-yl-cyclopentylamine (intermediate Q) and 2-methyl-4,6-bis-trifluoromethyl-benzoic acid (CAS 895580-37-7).

Example 104 cis-2-Methylsulfanyl-N-(2-pyrrolidin-1-yl-cyclopentyl)-4,6-bis-trifluoromethyl-benzamide

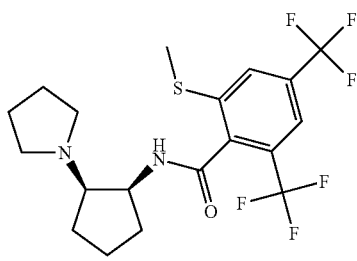

The title compound, white solid, MS: m/e=441.2 [(M+H)+], was prepared in accordance with the general method of example 5 from cis-2-pyrrolidin-1-yl-cyclopentylamine (intermediate Q) and 2-methylsulfanyl-4,6-bis-trifluoromethyl-benzoic acid (CAS 896120-49-3).

Example 105 cis-2-Fluoro-N-(2-pyrrolidin-1-yl-cyclopentyl)-4,6-bis-trifluoromethyl-benzamide

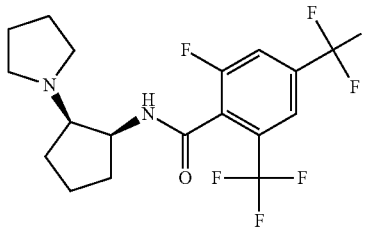

The title compound, white solid, MS: m/e=413.2 [(M+H)+], was prepared in accordance with the general method of example 5 from cis-2-pyrrolidin-1-yl-cyclopentylamine (intermediate Q) and 2-fluoro-4,6-bis-trifluoromethyl-benzoic acid.

Example 106

4-Fluoro-2,6-dimethyl-N-cis-(2-pyrrolidin-1-yl-cyclopentyl)-benzamide

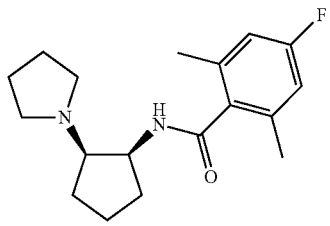

The title compound, white solid, MS: m/e=304.9 [(M+H)+], was prepared in accordance with the general method of example 5 from cis-2-pyrrolidin-1-yl-cyclopentylamine (intermediate Q) and 2,6-dimethyl-4-fluoro-benzoic acid.

Example 107

2-Isopropoxy-N-((1SR,2RS)-2-pyrrolidin-1-yl-cyclopentyl)-4-trifluoromethyl-benzamide

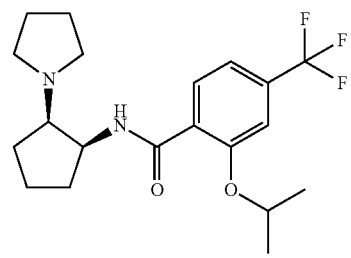

The title compound, light brown oil, MS: m/e=385.2 [(M+H)+], was prepared in accordance with the general method of example 5 from cis-2-pyrrolidin-1-yl-cyclopentylamine (intermediate Q) and 2-isopropoxy-4-trifluoromethyl-benzoic acid (intermediate AF).

Example 108 cis-2,6-Dichloro-N-(2-pyrrolidin-1-yl-cyclopentyl)-4-trifluoromethyl-benzamide

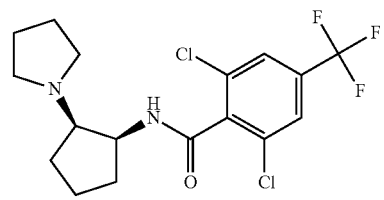

The title compound, white solid, MS: m/e=395.1 [(M+H)+], was prepared in accordance with the general method of example 5 from cis-2-pyrrolidin-1-yl-cyclopentylamine (intermediate Q) and 2,6-dichloro-4-trifluoromethyl-benzoic acid (intermediate Y).

Example 109 and 110

(+)-cis-N-2-Cyclopentylamino-cyclopentyl)-2-cyclopropyl-4-trifluoromethyl-benzamide and (−)-cis-N-2-Cyclopentylamino-cyclopentyl)-2-cyclopropyl-4-trifluoromethyl-benzamide

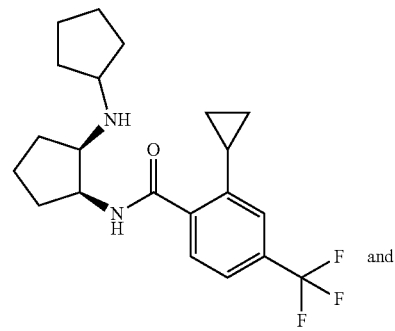

and

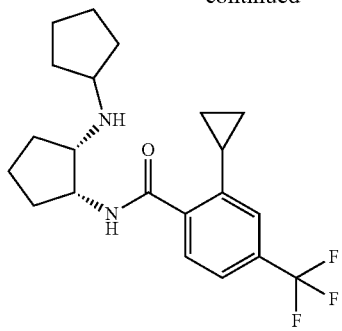

N-((1SR,2RS)-2-Cyclopentylamino-cyclopentyl)-2-cyclopropyl-4-trifluoromethyl-benzamide (example 102) was separated on Chiralpak AD with 4% ethanol in heptane. The first eluting enantiomer was (+)-cis-N-2-cyclopentylamino-cyclopentyl)-2-cyclopropyl-4-trifluoromethyl-benzamide, the second enantiomer was (−)-cis-N-2-cyclopentylamino-cyclopentyl)-2-cyclopropyl-4-trifluoromethyl-benzamide. The absolute configuration was not determined.

Example 111

2-Chloro-N-((1SR,2RS)-2-pyrrolidin-1-yl-cyclopentyl)-4,6-bis-trifluoromethyl-benzamide

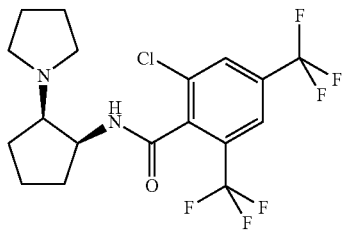

The title compound, white solid, MS: m/e=429.1 [(M+H)$^+$], was prepared in accordance with the general method of example 5 from cis-2-pyrrolidin-1-yl-cyclopentylamine (intermediate Q) and 2-chloro-4,6-bis-trifluoromethyl-benzoic acid Example 112

2-Isopropyl-N-((1SR,2RS)-2-pyrrolidin-1-yl-cyclopentyl)-4-trifluoromethyl-benzamide

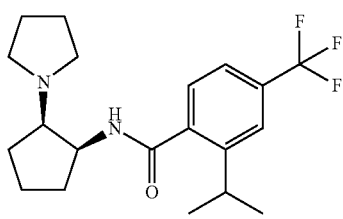

The title compound, orange solid, MS: m/e=369.2 [(M+H)$^+$], was prepared in accordance with the general method of example 5 from cis-2-pyrrolidin-1-yl-cyclopentylamine (intermediate Q) and 2-isopropyl-4-trifluoromethyl-benzoic acid (intermediate AH).

Example 113

5-Trifluoromethyl-biphenyl-2-carboxylic acid ((1SR,2RS)-2-pyrrolidin-1-yl-cyclopentyl)-amide

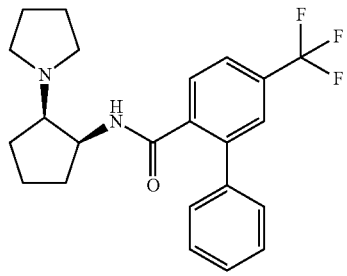

The title compound, off-white oil, MS: m/e=403.3 [(M+H)$^+$], was prepared in accordance with the general method of example 5 from cis-2-pyrrolidin-1-yl-cyclopentylamine (intermediate Q) and 5-trifluoromethyl-biphenyl-2-carboxylic acid (intermediate AI).

Example 114 and 115

(−)-2-Bromo-6-methoxy-N-cis-(2-pyrrolidin-1-yl-cyclopentyl)-4-trifluoromethyl-benzamide and (+)-2-Bromo-6-methoxy-N-cis-(2-pyrrolidin-1-yl-cyclopentyl)-4-trifluoromethyl-benzamide

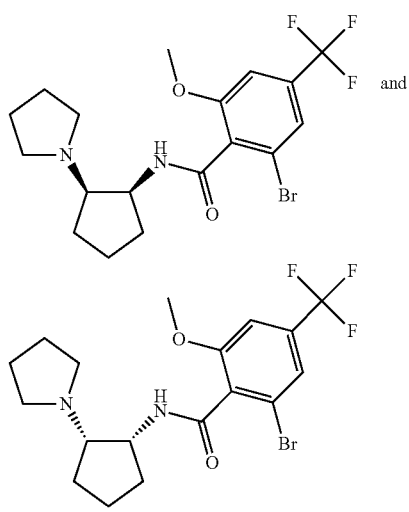

2-Bromo-6-methoxy-N-cis-(2-pyrrolidin-1-yl-cyclopentyl)-4-trifluoromethyl-benzamide (example 101) was separated on Reprosil Chiral NR with 8% ethanol in heptane. The first eluting enantiomer was (−)-2-bromo-6-methoxy-N-cis-(2-pyrrolidin-1-yl-cyclopentyl)-4-trifluoromethyl-benzamide, the second enantiomer was (+)-2-bromo-6-methoxy- N-cis-(2-pyrrolidin-1-yl-cyclopentyl)-4-trifluoromethyl-benzamide. The absolute configuration was not determined.

Example 116

2,6-Dimethoxy-N-((1SR,2RS)-2-pyrrolidin-1-yl-cyclopentyl)-4-trifluoro methyl benzamide

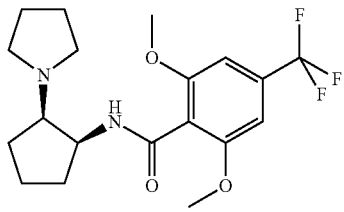

The title compound, yellow oil, MS: m/e=387.2 [(M+H)⁺], was prepared in accordance with the general method of example 5 from cis-2-pyrrolidin-1-yl-cyclopentylamine (intermediate Q) and 2,6-dimethoxy-4-trifluoromethyl-benzoic acid (intermediate AJ).

Example 117 cis-2-Methylsulfanyl-N-(2-pyrrolidin-1-yl-cyclopentyl)-6-trifluoromethyl-benzamide

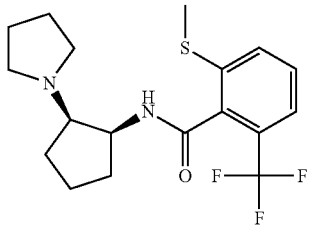

The title compound, white solid, MS: m/e=373.1 [(M+H)⁺], was prepared in accordance with the general method of example 5 from cis-2-pyrrolidin-1-yl-cyclopentylamine (intermediate Q) and 2-methylsulfanyl-6-trifluoromethyl-benzoic acid (intermediate Z).

Example 118 and 119

(+)-cis-2-Methylsulfanyl-N-(2-pyrrolidin-1-yl-cyclopentyl)-4,6-bis-trifluoromethyl-benzamide and (−)-cis-2-Methylsulfanyl-N-(2-pyrrolidin-1-yl-cyclopentyl)-4,6-bis-trifluoromethyl-benzamide

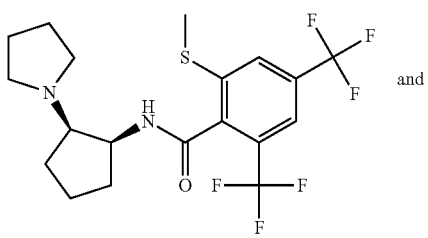
and
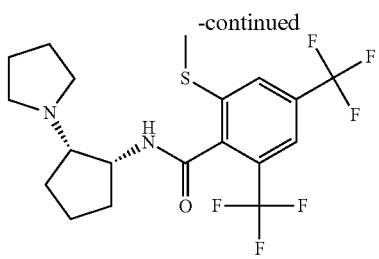

cis-2-Methylsulfanyl-N-(2-pyrrolidin-1-yl-cyclopentyl)-4,6-bis-trifluoromethyl-benzamide (example 104) was separated on Reprosil Chiral NR with 5% isopropanol in heptane. The first eluting enantiomer was (+)-cis-2-methylsulfanyl-N-(2-pyrrolidin-1-yl-cyclopentyl)-4,6-bis-trifluoromethyl-benzamide, the second enantiomer was (−)-cis-2-methylsulfanyl-N-(2-pyrrolidin-1-yl-cyclopentyl)-4,6-bis-trifluoromethyl-benzamide. The absolute configuration was not determined.

Example 120 and 121

(−)-cis-2-Cyclopropyl-6-ethyl-N-(2-pyrrolidin-1-yl-cyclopentyl)-benzamide and (+)-cis-2-Cyclopropyl-6-ethyl-N-(2-pyrrolidin-1-yl-cyclopentyl)-benzamide

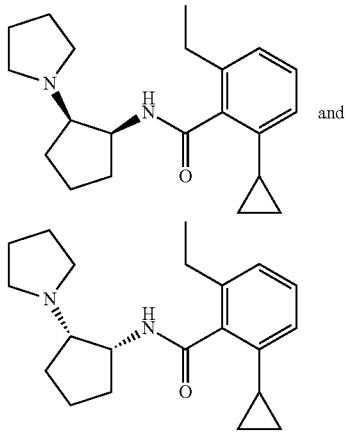

cis-2-Methylsulfanyl-N-(2-pyrrolidin-1-yl-cyclopentyl)-4,6-bis-trifluoromethyl-benzamide (example 104) was separated on Reprosil Chiral NR with 10% ethanol in heptane. The first eluting enantiomer was (−)-cis-2-cyclopropyl-6-ethyl-N-(2-pyrrolidin-1-yl-cyclopentyl)-benzamide, the second enantiomer was (+)-cis-2-cyclopropyl-6-ethyl-N-(2-pyrrolidin-1-yl-cyclopentyl)-benzamide. The absolute configuration was not determined.

Example 122

4-Bromo-2-methyl-N-((cis)-2-pyrrolidin-1-yl-cyclopentyl)-benzamide

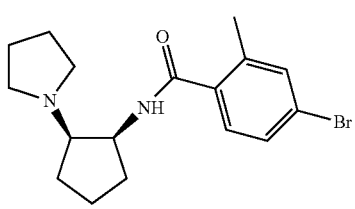

The title compound, white solid, MS: m/e=351.2/353.1 [(M+H)⁺], was prepared in accordance with the general method of example 5 from cis-2-pyrrolidin-1-yl-cyclopentylamine (intermediate Q) and 4-bromo-2-methyl-benzoic acid.

Example 123

2-Methoxy-6-methylsulfanyl-N-((1SR,2RS)-2-pyrrolidin-1-yl-cyclobutyl)-4-trifluoromethyl-benzamide

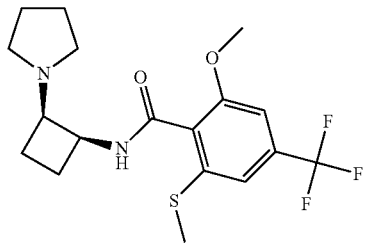

The title compound, off-white foam, MS: m/e=389.2 [(M+H)⁺], was prepared in accordance with the general method of example 5 from 2-pyrrolidin-1-yl-cyclobutylamine hydrochloride (intermediate AB) and 2-methoxy-6-methylsulfanyl-4-trifluoromethyl-benzoic acid (intermediate A). The 2 diastereomers were separated by column chromatography.

Example 124

2-Methoxy-6-methylsulfanyl-N-((1SR,2RS)-2-pyrrolidin-1-yl-cyclopropyl)-4-trifluoromethyl-benzamide

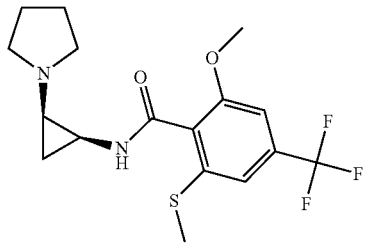

The title compound, light yellow solid, MS: m/e=375.2 [(M+H)⁺], was prepared in accordance with the general method of example 10 from N-((1SR,2RS)-2-amino-cyclopropyl)-2-methoxy-6-methylsulfanyl-4-trifluoromethyl-benzamide (intermediate AC) and 1,4-dibromobutane.

Examples 125 and 126

(+)-cis-2-Fluoro-N-(2-pyrrolidin-1-yl-cyclopentyl)-4,6-bis-trifluoromethyl-benzamide and (−)-cis-2-Fluoro-N-(2-pyrrolidin-1-yl-cyclopentyl)-4,6-bis-trifluoromethyl-benzamide

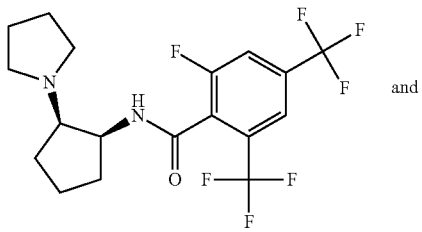

and

-continued

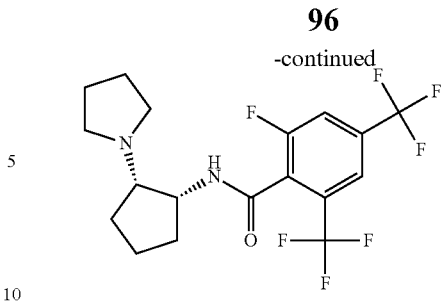

cis-2-Fluoro-N-(2-pyrrolidin-1-yl-cyclopentyl)-4,6-bis-trifluoromethyl-benzamide (example 104) was separated on Reprosil Chiral NR with 3% ethanol in heptane. The first eluting enantiomer was (+)-cis-2-fluoro-N-(2-pyrrolidin-1-yl-cyclopentyl)-4,6-bis-trifluoromethyl-benzamide, the second enantiomer was (−)-cis-2-fluoro-N-(2-pyrrolidin-1-yl-cyclopentyl)-4,6-bis-trifluoromethyl-benzamide. The absolute configuration was not determined.

Example 127

(+)-2-Methylsulfanyl-N-((cis)-2-pyrrolidin-1-yl-cyclohexyl)-4,6-bis-trifluoromethyl-benzamide

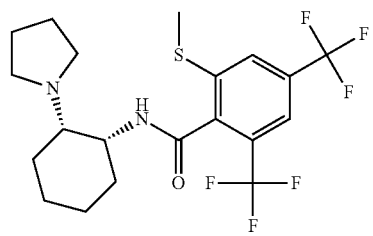

2-Methylsulfanyl-N-((cis)-2-pyrrolidin-1-yl-cyclohexyl)-4,6-bis-trifluoromethyl-benzamide (example 53) was separated on Reprosil Chiral NR with 3% ethanol in heptane. The first eluting enantiomer was (+)-2-methylsulfanyl-N-((cis)-2-pyrrolidin-1-yl-cyclohexyl)-4,6-bis-trifluoromethyl-benzamide, the second enantiomer could not be isolated enantiomerically pure. The absolute configuration was not determined.

Examples 128 and 129

(+)-2,6-Dichloro-N-cis-(2-pyrrolidin-1-yl-cyclopentyl)-4-trifluoromethyl-benzamide and (−)-2,6-Dichloro-N-cis-(2-pyrrolidin-1-yl-cyclopentyl)-4-trifluoromethyl-benzamide

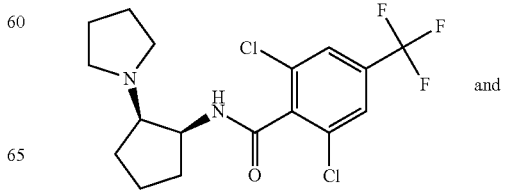

and

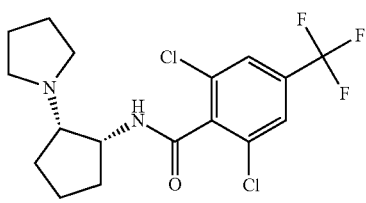

2,6-Dichloro-N-cis-(2-pyrrolidin-1-yl-cyclopentyl)-4-trifluoromethyl-benzamide (example 107) was separated on Chiralpak AD with 2% isopropanol in heptane. The first eluting enantiomer was (+)-2,6-dichloro-N-cis-(2-pyrrolidin-1-yl-cyclopentyl)-4-trifluoromethyl-benzamide, the second enantiomer was (−)-2,6-dichloro-N-cis-(2-pyrrolidin-1-yl-cyclopentyl)-4-trifluoromethyl-benzamide. The absolute configuration was not determined.

Example 130

2-Cyclopropyl-N-((cis)-2-pyrrolidin-1-yl-cyclopentyl)-4,6-bis-trifluoromethyl-benzamide

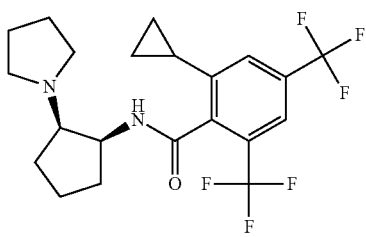

The title compound, off-white solid, MS: m/e=435.3 [(M+H)⁺], was prepared in accordance with the general method of example 5 from cis-2-pyrrolidin-1-yl-cyclopentylamine (intermediate Q) and 2-cyclopropyl-4,6-bis-trifluoromethyl-benzoic acid (intermediate AN).

Example 131

2-Cyclopropyl-6-methoxy-N-((cis)-2-pyrrolidin-1-yl-cyclopentyl)-4 trifluoromethyl-benzamide

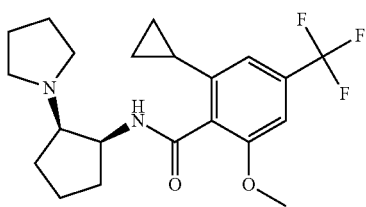

The title compound, light yellow solid, MS: m/e=397.2 [(M+H)⁺], was prepared in accordance with the general method of example 5 from cis-2-pyrrolidin-1-yl-cyclopentylamine (intermediate Q) and 2-cyclopropyl-6-methoxy-4-trifluoromethyl-benzoic acid (intermediate AS).

Example 132

2,6-Dimethyl-N-((cis)-2-pyrrolidin-1-yl-cyclopentyl)-4-trifluoromethyl-benzamide

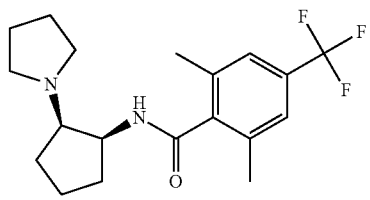

The title compound, light yellow oil, MS: m/e=355.3 [(M+H)⁺], was prepared in accordance with the general method of example 5 from cis-2-pyrrolidin-1-yl-cyclopentylamine (intermediate Q) and 2,6-dimethyl-4-trifluoromethyl-benzoic acid (intermediate AQ).

Example 133

2-Difluoromethoxy-6-methoxy-N-((cis)-2-pyrrolidin-1-yl-cyclopentyl)-4-trifluoromethyl-benzamide

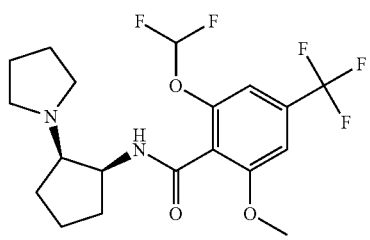

The title compound, light yellow solid, MS: m/e=423.2 [(M+H)⁺], was prepared in accordance with the general method of example 5 from cis-2-pyrrolidin-1-yl-cyclopentylamine (intermediate Q) and 2-difluoromethoxy-6-methoxy-N-((1S,2R)-2-pyrrolidin-1-yl-cyclopentyl)-4-trifluoromethyl-benzamide (intermediate AT).

Example 134

N-((cis)-2-Cyclopentylamino-cyclopentyl)-2-methylsulfanyl-4,6-bis-trifluoromethyl-benzamide

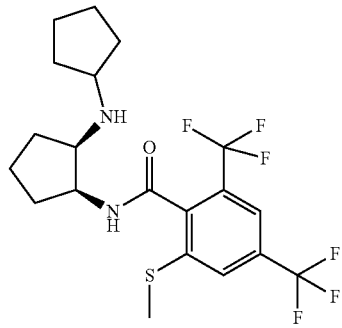

The title compound, light pink solid, MS: m/e=455.3 [(M+H)⁺], was prepared in accordance with the general method of example 5 from (1RS,2SR)-N-Cyclopentyl-cyclopentane-1,2-diamine (intermediate AE) and 2-methylthio-4,6-bis(trifluoromethyl)benzoic acid (CAS 896120-49-3).

Example 135

2-Cyclobutyl-N-((cis)-2-pyrrolidin-1-yl-cyclopentyl)-4-trifluoromethyl-benzamide

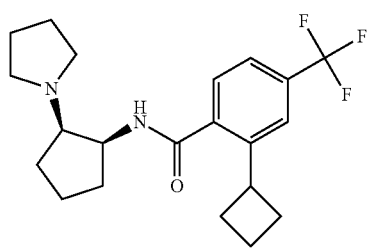

The title compound, light orange solid, MS: m/e=381.4 [(M+H)⁺], was prepared in accordance with the general method of example 5 from cis-2-pyrrolidin-1-yl-cyclopentylamine (intermediate Q) and 2-cyclobutyl-4-trifluoromethyl-benzoic acid (intermediate AP).

Example 136

2-Cyclopropyl-N-((cis)-2-pyrrolidin-1-yl-cyclohexyl)-4,6-bis-trifluoromethyl-benzamide

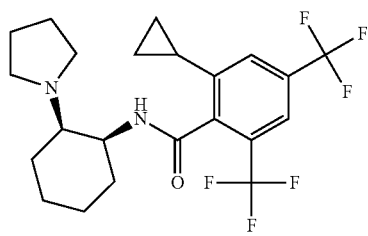

The title compound, white solid, MS: m/e=449.3 [(M+H)⁺], was prepared in accordance with the general method of example 5 from cis-2-pyrrolidin-1-yl-cyclohexylamine dihydrochloride (intermediate F) and 2-cyclopropyl-4,6-bis-trifluoromethyl-benzoic acid (intermediate AN).

Example 137

2-Ethyl-N-((cis)-2-pyrrolidin-1-yl-cyclopentyl)-4,6-bis-trifluoromethyl-benzamide

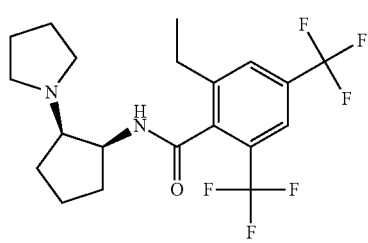

The title compound, white solid, MS: m/e=423.3 [(M+H)⁺], was prepared in accordance with the general method of example 5 from cis-2-pyrrolidin-1-yl-cyclopentylamine (intermediate Q) and 2-ethyl-4,6-bis-trifluoromethyl-benzoic acid (intermediate AO).

Example 138 and 139

(−)-2-Cyclopropyl-N-((1R,2S or 1S,2R)-2-pyrrolidin-1-yl-cyclopentyl)-4,6-bis-trifluoromethyl-benzamide and (+)-2-Cyclopropyl-N-((1R,2S or 1S,2R)-2-pyrrolidin-1-yl-cyclopentyl)-4,6-bis-trifluoromethyl-benzamide

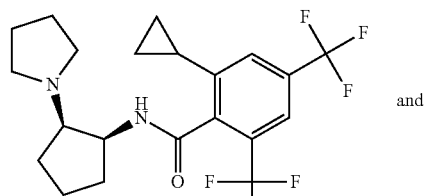

and

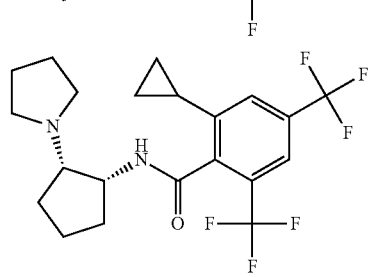

Cis-2-Cyclopropyl-N-(2-pyrrolidin-1-yl-cyclopentyl)-4,6-bis-trifluoromethyl-benzamide (example 104) was separated on Reprosil Chiral NR with 9% ethanol in heptane. The first eluting enantiomer was (−)-2-cyclopropyl-N-((1R,2S or 1S,2R)-2-pyrrolidin-1-yl-cyclopentyl)-4,6-bis-trifluoromethyl-benzamide, the second enantiomer was (+)-2-cyclopropyl-N-((1R,2S or 1S,2R)-2-pyrrolidin-1-yl-cyclopentyl)-4,6-bis-trifluoromethyl-benzamide. The absolute configuration was not determined.

Example 140

2-Ethyl-6-methoxy-N-((cis)-2-pyrrolidin-1-yl-cyclopentyl)-4-trifluoromethyl-benzamide

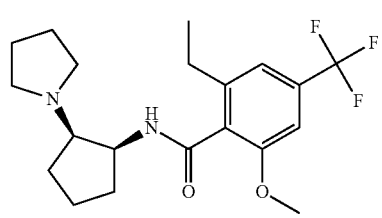

The title compound, light yellow oil, MS: m/e=385.2 [(M+H)⁺], was prepared in accordance with the general method of example 5 from cis-2-pyrrolidin-1-yl-cyclopentylamine (intermediate Q) and 2-ethyl-6-methoxy-4-trifluoromethyl-benzoic acid (intermediate AR).

Example 141 and 142

(+)-2-Ethyl-N-(2-pyrrolidin-1-yl-cyclopentyl)-4,6-bis-trifluoromethyl-benzamide and (−)-2-Ethyl-N-(2-pyrrolidin-1-yl-cyclopentyl)-4,6-bis-trifluoromethyl-benzamide

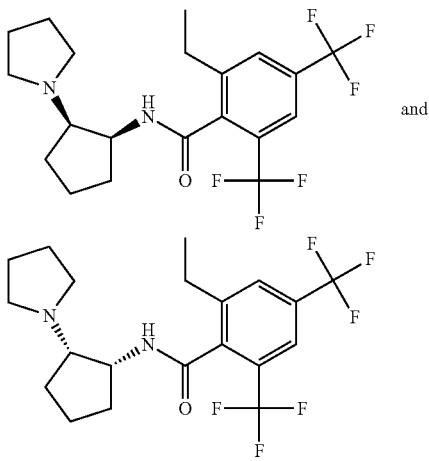

Cis-2-Ethyl-N-(2-pyrrolidin-1-yl-cyclopentyl)-4,6-bis-trifluoromethyl-benzamide (example 136) was separated on Reprosil Chiral NR with 9% ethanol in heptane. The first eluting enantiomer was (+)-2-ethyl-N-(2-pyrrolidin-1-yl-cyclopentyl)-4,6-bis-trifluoromethyl-benzamide, the second enantiomer was (−)-2-ethyl-N-(2-pyrrolidin-1-yl-cyclopentyl)-4,6-bis-trifluoromethyl-benzamide. The absolute configuration was not determined.

The compounds of formula I and their pharmaceutically usable addition salts possess valuable pharmacological properties. Specifically, Compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies).

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.
Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds described in examples 1-60 have an $IC_{50}$ data <1.0 μM. The $IC_{50}$ data (<0.1 μM) for representative compounds 1-141 is provided in table 1.

| Example | $IC_{50}$ data (μM) |
|---|---|
| 1 | 0.05672 |
| 3 | 0.0998 |
| 6 | 0.05035 |
| 7 | 0.04955 |
| 8 | 0.092 |
| 18 | 0.0814 |
| 19 | 0.0979 |
| 22 | 0.0894 |
| 28 | 0.0921 |
| 39 | 0.0248 |
| 45 | 0.0507 |
| 46 | 0.0573 |
| 47 | 0.0227 |
| 48 | 0.0869 |
| 52 | 0.0379 |
| 53 | 0.0367 |
| 54 | 0.0799 |
| 55 | 0.0846 |
| 58 | 0.0276 |
| 59 | 0.0611 |
| 61 | 0.0659 |
| 62 | 0.0316 |
| 65 | 0.0564 |
| 68 | 0.0194 |
| 78 | 0.0754 |
| 80 | 0.0896 |
| 84 | 0.089 |
| 85 | 0.0604 |
| 89 | 0.0794 |
| 91 | 0.0453 |
| 92 | 0.0954 |
| 94 | 0.0984 |
| 96 | 0.0428 |
| 97 | 0.0824 |
| 98 | 0.0801 |
| 101 | 0.0948 |
| 102 | 0.0351 |
| 103 | 0.0249 |
| 104 | 0.0189 |
| 105 | 0.0751 |
| 108 | 0.0882 |
| 109 | 0.0253 |
| 110 | 0.0543 |
| 114 | 0.0668 |
| 115 | 0.0714 |
| 118 | 0.06 |
| 119 | 0.0654 |
| 120 | 0.0552 |
| 121 | 0.0361 |
| 126 | 0.074 |
| 127 | 0.065 |
| 128 | 0.0691 |
| 129 | 0.0645 |
| 130 | 0.0354 |
| 131 | 0.0199 |
| 132 | 0.0365 |
| 133 | 0.0908 |
| 134 | 0.0957 |
| 136 | 0.0479 |

-continued

| Example | IC$_{50}$ data (μM) |
|---|---|
| 137 | 0.0462 |
| 138 | 0.0679 |
| 139 | 0.0325 |
| 140 | 0.0554 |
| 141 | 0.0435 |
| 142 | 0.068 |

The present invention also provides pharmaceutical compositions containing compounds of the invention, for example, compounds of formula IA or formula IB or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula IA-1

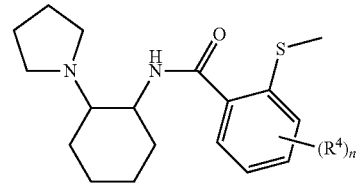

IA-1 wherein
$R^4$ is $CF_3$, lower alkoxy, lower alkyl, or halogen and
n is 1 or 2;
  or a pharmaceutically acceptable acid addition salt, a racemic mixture, enantiomer or optical isomer thereof.
2. The compound of claim 1, selected from the group consisting of
  cis-2-methoxy-6-methylsulfanyl-N-2-pyrrolidin-1-yl-cyclohexyl)-4-trifluoromethyl-benzamide;
  cis-2-methylsulfanyl-N-(2-pyrrolidin-1-yl-cyclohexyl)-4-trifluoromethyl-benzamide;
  (−)-cis-2-methoxy-6-methylsulfanyl-N-(2-pyrrolidin-1-yl-cyclohexyl)-4-trifluoromethyl-benzamide;

(+)-cis-2-methoxy-6-methylsulfanyl-N-(2-pyrrolidin-1-yl-cyclohexyl)-4-trifluoromethyl-benzamide;
(−)-cis-2-methylsulfanyl-N-(2-pyrrolidin-1-yl-cyclohexyl)-4-trifluoromethyl-benzamide;
2-methylsulfanyl-N-((cis-2-pyrrolidin-1-yl-cyclohexyl)-4,6-bis-trifluoromethyl-benzamide; and
(+)-2-methylsulfanyl-N-((cis)-2-pyrrolidin-1-yl-cyclohexyl)-4,6-bis-trifluoromethyl-benzamide.

3. A compound of formula IB-1

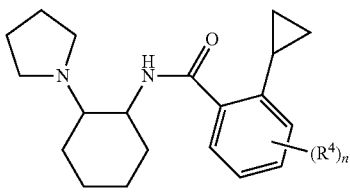

IB-1 wherein
$R^4$ is $CF_3$, lower alkoxy, lower alkyl, or halogen and
n is 1 or 2;
or a pharmaceutically acceptable acid addition salt, a racemic mixture, enantiomer or optical isomer thereof.

4. The compound of claim 3 selected from the group consisting of
cis-2-cyclopropyl-N-(2-pyrrolidin-1-yl-cyclohexyl)-4-trifluoromethyl-benzamide;
(−)-cis-2-cyclopropyl-N-(2-pyrrolidin-1-yl-cyclohexyl)-4-trifluoromethyl-benzamide;
(+)-cis-2-cyclopropyl-N-(2-pyrrolidin-1-yl-cyclohexyl)-4-trifluoromethyl-benzamide; and
2-cyclopropyl-N-((cis)-2-pyrrolidin-1-yl-cyclohexyl)-4,6-bis-trifluoromethyl-benzamide.

5. A pharmaceutical composition comprising a therapeutically effective amount of a compound of formula IA-1

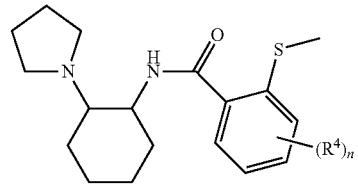

IA-1 wherein
$R^4$ is $CF_3$, lower alkoxy, lower alkyl, or halogen and
n is 1 or 2;
or a pharmaceutically acceptable acid addition salt, a racemic mixture, enantiomer or optical isomer thereof and a pharmaceutically acceptable carrier.

6. A pharmaceutical composition comprising a therapeutically effective amount of a compound of formula IB-1

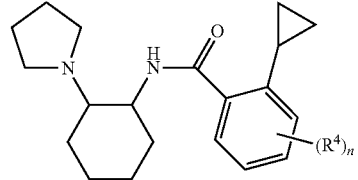

IB-1 wherein
$R^4$ is $CF_3$, lower alkoxy, lower alkyl, or halogen and
n is 1 or 2;
or a pharmaceutically acceptable acid addition salt, a racemic mixture, enantiomer or optical isomer thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,080,541 B2 | Page 1 of 1 |
| APPLICATION NO. | : 12/859305 | |
| DATED | : December 20, 2011 | |
| INVENTOR(S) | : Kolczewski et al. | |

It is certified that error appears in the above-identified patent and that said Letters Patent is hereby corrected as shown below:

TITLE PAGE Item 73:

-The Assignee information reads "Hoffman-La Roche Inc., Nutley, NJ (US)". The Assignee information should read -- Hoffmann-La Roche Inc., Nutley, NJ (US) --.

Signed and Sealed this
Twenty-first Day of February, 2012

David J. Kappos
*Director of the United States Patent and Trademark Office*